(12) United States Patent
Multani et al.

(10) Patent No.: US 9,944,949 B2
(45) Date of Patent: Apr. 17, 2018

(54) COMPOSITIONS AND METHODS CONFERRING RESISTANCE OF MAIZE TO CORN ROOTWORM 1

(71) Applicants: Pioneer Hi-Bred International, Inc., Johnston, IA (US); Purdue Research Foundation, West Lafayette, IN (US)

(72) Inventors: Dilbag S. Multani, Urbandale, IA (US); Gurmukh S. Johal, West Lafayette, IN (US); Bala K. P. Venkata, West Lafayette, IN (US)

(73) Assignees: PURDUE RESEARCH FOUNDATION, West Lafayette, IN (US); PIONEER HI-BRED INTERNATIONAL, Johnston, IA (US)

( * ) Notice: Subject to any disclaimer, the term of this patent is extended or adjusted under 35 U.S.C. 154(b) by 82 days.

(21) Appl. No.: 14/430,002

(22) PCT Filed: Sep. 20, 2013

(86) PCT No.: PCT/US2013/061026
§ 371 (c)(1),
(2) Date: Mar. 20, 2015

(87) PCT Pub. No.: WO2014/047505
PCT Pub. Date: Mar. 27, 2014

(65) Prior Publication Data
US 2015/0275228 A1    Oct. 1, 2015

Related U.S. Application Data

(60) Provisional application No. 61/781,057, filed on Mar. 14, 2013, provisional application No. 61/703,396, filed on Sep. 20, 2012.

(51) Int. Cl.
| | | |
|---|---|---|
| *C12N 15/82* | (2006.01) | |
| *A01H 1/04* | (2006.01) | |
| *A01H 5/10* | (2018.01) | |
| *C07K 14/415* | (2006.01) | |
| *C12Q 1/68* | (2018.01) | |

(52) U.S. Cl.
CPC ........... *C12N 15/8286* (2013.01); *A01H 1/04* (2013.01); *A01H 5/10* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2006/0150283 A1   7/2006  Alexandrov et al.
2008/0313777 A1*  12/2008  Dhugga ............... C07K 14/415
                                                              800/287
2011/0239329 A1   9/2011  Dhugga et al.
2012/0017338 A1   1/2012  Wu et al.
2012/0210462 A1   8/2012  Bermudez et al.

FOREIGN PATENT DOCUMENTS

WO   WO-2010/075143 A1   7/2010
WO   WO-2011/044254 A1   4/2011

OTHER PUBLICATIONS

Welner et al, 2016, NAC transcription factors: from structure to function in stress-associated networks. IN: Plant Transcription Factors, Gonzalez, ed. Elsevier, London, p. 199-212.*
Kjaersgaard et al (2011, J. Biol. Chem 286:35418-35429).*
Guo et al, 2004, Proc. Natl. Acad. Sci. USA 101: 9205-9210.*
Barros-Rios et al (2011, Phytochem. 72:365-371).*
Christensen et al (1992, Plant Mol. Biol. 18:675-689).*
Purdue University, 2009, https://extension.entm.purdue.edu/fieldcropsipm/insects/corn-rootworms.php.*
International Search Report and Written Opinion of the International Searching Authority dated Dec. 24, 2013 for international application PCT/US13/61026, filed on Sep. 20, 2013, and published as WO 2014/047505 on Mar. 27, 2014 (Applicant—Pioneer Hi-Bred Int'l, Inc. // Inventor—Multani, et al.) (14 pages).
International Preliminary Report on Patentability dated Mar. 24, 2015 for international application PCT/US13/61026, filed on Sep. 20, 2013, and published as WO 2014/047505 on Mar. 27, 2014 (Applicant—Pioneer Hi-Bred Int'l, Inc. // Inventor—Multani, et al.) (2 pages).
Dhillon B, Moose SP; and Johal GS. (2007). crw1—A novel maize mutant exceptionally susceptible to Western Corn Rootworm. Maize Genetics Conference Abstracts. Mar. 22-25, St. Charles, Illinois, available at http://www.maizegdb.org/data_center/reference?id=1079616 (2 pages).
Zhong, et al., "Transcriptional Activation of Secondary Wall Biosynthesis by Rice and Maize NAC and MYB Transcription Factors", Plant Cell Physiol. 52(10): 1856-1871 (2011).
UniProt G3M8D2 (2011) retrieved from http://www.uniprot.org/uniprot/G3M8D2 (5 pages).
UniProt Q9SNM6 (2000) retrieved from http://www.uniprot.org/uniprot/Q9SNM6 (7 pages).
UniProt C5YM23 (2009) retrieved from http://www.uniprot.org/uniprot/C5YM23 (6 pages).
UniProt Q5NKS7 (2005) retrieved from http://www.uniprot.org/uniprot/Q5NKS7 (6 pages).
UniProt I1MKD6 (2012) retrieved from http://www.uniprot.org/uniprot/I1MKD6.txt?version=3 (1 page).
UniProt I1KHQ4 (2012) retrieved from http://www.uniprot.org/uniprot/I1KHQ4 (6 pages).
UniProt Q84WP6 (2006) retrieved from http://www.uniprot.org/uniprot/Q84WP6 (9 pages).

(Continued)

*Primary Examiner* — Anne Kubelik
(74) *Attorney, Agent, or Firm* — Ballard Spahr LLP

(57) ABSTRACT

Methods and compositions for increasing a plant's resistance to an insect pest such as the corn rootworm are provided. Methods are provided for overexpression of Crw1, or variants thereof, in a host plant or plant cell to increase resistance to an insect pest in a plant such as maize. Moreover, methods are provided for identifying variants of Crw1 that when incorporated into a plant via transgenic or traditional breeding means increase resistance to an insect pest in a plant such as maize.

4 Claims, 28 Drawing Sheets

(56) References Cited

OTHER PUBLICATIONS

UniProt Q9LPI7 (2008) retreived from http://www.uniprot.org/uniprot/Q9LPI7 (9 pages).
UniProt Q9M274 (2006) retrieved from http://www.uniprot.org/uniprot/Q9M274 (9 pages).
UniProt B4FPS5 (2008) retrieved from http://www.uniprot.org/uniprot/B4FPS5 (7 pages).
UniProt Q5NKQ3 (2005) retrieved from http://www.uniprot.org/uniprot/Q5NKQ3 (6 pages).
UniProt F6HU82 (2011) retrieved from http://www.uniprot.org/uniprot/F6HU82 (6 pages).
UniProt G4V2G0 (2011) retrieved from http://www.uniprot.org/uniprot/G4V2G0 (5 pages).
UniProt D9ZJ90 (2010) retrieved from http://www.uniprot.org/uniprot/D9ZJ90 (5 pages).
UniProt F2DV83 (2011) retrieved from http://www.uniprot.org/uniprot/F2DV83 (5 pages).
Barros-Rios et al., "Cell wall composition as a maize defense mechanism against corn borers" (2011), Phytochem. 72:365-371.
Non Final Rejection dated Feb. 15, 2017 by the USPTO for U.S. Appl. No. 14/430,017, filed Mar. 20, 2015 and published as US 2015-0240257 A1 on Aug. 27, 2015 (Applicant-E.I. Dupont De Nemours and Company) (15 pages).
MBS Genetics, LLC. 2011 Genetic Handbook (136 pages).
Ooka et al., Comprehensive Analysis of NAC Family Genes in *Oryza sativa* and *Arabidopsis thaliana*. DNA Res. 2003; 10:239-47.
Venkata et al., crw1—A Novel Maize Mutant Highly Susceptible to Foliar Damage by the Western Corn Rootworm Beetle. PLos One. 2013; 8(8):e71296 (11 pages).
Zukoff et al., Western Corn Rootworm Larval Movement in SmartStax Seed Blend Scenarios. J Econ Entomol. 2012; 105(4):1248-60.

\* cited by examiner

FIG. 6A

```
            1.........11.........21.........31.........41.........51.........60
ZmCIwl-WT   ATGAGCAGCTCGGTGAACGGGCAGTCGGTGCTGGTGCCCGGGTTCCGGTTCCACCCCACG
ZmCIwl-Ac   ATGAGCAGCTCGGTGAACGGGCAGTCGGTGCTGGTGCCCGGGTTCCGGTTCCACCCCACG
            ************************************************************

61........71........81........91........101........111........120
ZmCIwl-WT   GAGGAGGAGCTGCTCAACTACTA_____CTTCCGCAAGAAGTGGCCTCCCAGGAGA
ZmCIwl-Ac   GAGGAGGAGCTGCTCAACTACTA[TTCTACTA]CTTCCGCAAGAAGTGGCCTCCCAGGAGA
            ***********************          ***************************

121........131........141........151........161........171........180
ZmCIwl-WT   TCGACCTCGACGTCATCCGCGACCTCGACCTCAACAAGAGCTGAGCTGAGCCAGGACATCCAAG
ZmCIwl-Ac   TCGACCTCGACGTCATCCGCGACCTCGACCTCAACAAGAGCTGAGCTGAGCCAGGACATCCAAG
            ****************************************************************

181........191........201........211........221........231........240
ZmCIwl-WT   AGAAATGCAAGATCGGAGATCGGAGTCGGGTGGGTGGGTCCCCAGAACGACTACTTCTTCAGCCACAAGGACA
ZmCIwl-Ac   AGAAATGCAAGATCGGAGATCGGAGTCGGGTGGGTGGGTCCCCAGAACGACTACTTCTTCAGCCACAAGGACA
            ****************************************************************

241........251........261........271........281........291........300
ZmCIwl-WT   AGAAGTACCGACGGGAGAGGGACGCCAACAAGCGGCCACCAAGCGGCCGCCGGGGTTCTGGGAAGCCA
ZmCIwl-Ac   AGAAGTACCGACGGGAGAGGGACGCCAACAAGCGGCCACCAAGCGGCCGCCGGGGTTCTGGGAAGCCA
            ****************************************************************

301........311........321........331........341........351........360
ZmCIwl-WT   CCGGCCGGACAAGGCCATCTACAACGCGGTCAAGGCCGTCAAGGCAGGCCATGGCCATGGCCAAGACGCTCG
ZmCIwl-Ac   CCGGCCGGACAAGGCCATCTACAACGCGGTCAAGGCCGTCAAGGCAGGCCATGGCCATGGCCAAGACGCTCG
            ****************************************************************

361........371........381........391........401........411........420
ZmCIwl-WT   TCTTCTACAAGGACGCCGCGCCGCCCAGGAAGTCCGACTGGGATCATGCAGTCACCGAGTACC
ZmCIwl-Ac   TCTTCTACAAGGACGCCGCGCCGCCCAGGAAGTCCGACTGGGATCATGCAGTCACCGAGTACC
            ****************************************************************
```

FIG. 6B

```
             421.........431.........441.........451.........461.........471.........480
ZmCrw1-WT    GCCTCGACGACCGGCTGCTGCTGCTGCTGGATCCGGTGATGCCATGGCCAAGGAGG
ZmCrw1-Ac    GCCTCGACGACCGGCTGCTGCTGCTGCTGGATCCGGTGATGCCATGGCCAAGGAGG
             ************************************************************

481.........491.........501.........511.........521.........531.........540
ZmCrw1-WT    ACGGCAGCCGCCACGGCTGCTCCTACGCCGCGTCGTCCGGACGGCGGCAGGAGGACG
ZmCrw1-Ac    ACGGCAGCCGCCACGGCTGCTCCTACGCCGCGTCGTCCGGACGGCGGCAGGAGGACG
             ************************************************************

541.........551.........561.........571.........581.........591.........600
ZmCrw1-WT    GCTGGGTGGTGTGCAGGGTGTTCAAGAAGAAGCACCACCAAGGAGTCAGGTGGGGGCG
ZmCrw1-Ac    GCTGGGTGGTGTGCAGGGTGTTCAAGAAGAAGCACCACCAAGGAGTCAGGTGGGGGCG
             ************************************************************

601.........611.........621.........631.........641.........651.........660
ZmCrw1-WT    GGGCAACAAGCACGGCAGCAGTAACAGCAGCGAGCATGGGCACGGCAGCGCCAAGGCAT
ZmCrw1-Ac    GGGCAACAAGCACGGCAGCAGTAACAGCAGCGAGCATGGGCACGGCAGCGCCAAGGCAT
             ************************************************************

661.........671.........681.........691.........701.........711.........720
ZmCrw1-WT    CGGCTGCGGCTGCGGCTGCCTGGGCGCGGGCACCAGCAGCACCATGGAGGCTGCAGTACTCCT
ZmCrw1-Ac    CGGCTGCGGCTGCGGCTGCCTGGGCGCGGGCACCAGCAGCACCATGGAGGCTGCAGTACTCCT
             ************************************************************

721.........731.........741.........751.........761.........771.........780
ZmCrw1-WT    CCAGGCGACGGAGGCGCTGGACCAGATGCAGTACATGGGCAGGTCGTGCAAGCAGGAGC
ZmCrw1-Ac    CCAGGCGACGGAGGCGCTGGACCAGATGCAGTACATGGGCAGGTCGTGCAAGCAGGAGC
             ************************************************************

781.........791.........801.........811.........821.........831.........840
ZmCrw1-WT    ACGAGCTGGTCGTCCGCCGGCGCCGGGACGGGCGCGGTCCAGGTACTCC
ZmCrw1-Ac    ACGAGCTGGTCGTCCGCCGGCGCCGGGACGGGCGCGGTCCAGGTACTCC
             ************************************************************
```

FIG. 6C

```
                    841.......851.......861.......871.......881.......891......900
ZmCrwl-WT   GGCCCATCGAGACCGTTCTGGGCCGGCCACGCGTTCATGAAGCTTCCCGGCGTCGAGAGCC
Zmcrwl-Ac   GGCCCATCGAGACCGTTCTGGGCCGGCCACGCGTTCATGAAGCTTCCCGGCGTCGAGAGCC
            ************************************************************

901.......911.......921.......931.......941.......951......960
ZmCrwl-WT   CGTCCGGCGGCCGCGGTCCGCATCGCTGACCTGACACAGCCGGCAGCACGACGAGCTCACCGCG
Zmcrwl-Ac   CGTCCGGCGGCCGCGGTCCGCATCGCTGACCTGACACAGCCGGCAGCACGACGAGCTCACCGCG
            ************************************************************

961.......971.......981.......991.......1001......1011.....1020
ZmCrwl-WT   CCGCCCGGAACGGGAICACGGACTGGGCCATGATGGACCGGCCGTTGTGGCGTCGCACCTGA
Zmcrwl-Ac   CCGCCCGGAACGGGAATCACGGACTGGGCCATGATGGACCGGCCGTGTGGCGTCGCACCTGA
            ************************************************************

1021......1031......1041......1051......1061......1071......1080
ZmCrwl-WT   ACGGGCAGCAGGCGGCCGCCGCCGGGGACCAGCAGCTCGGACCGGGTGCGGCTTCGACGCGG
Zmcrwl-Ac   ACGGGCAGCAGGCGGCCGCCGCCGGGGACCAGCAGCTCGGACCGGGTGCGGCTTCGACGCGG
            ************************************************************

1081......1091......1101......1111......1121......1131......1140
ZmCrwl-WT   ACGGCGGCGCGGAAGACGGGAGCGGGAGCGGCCTCGGCCTTCACTCGGCCGCGGCCAGCCGGC
Zmcrwl-Ac   ACGGCGGCGCGGAAGACGGGAGCGGGAGCGGCCTCGGCCTTCACTCGGCCGCGGCCAGCCGGC
            ************************************************************

1141......1151......1161......1171......1181......1191......1200
ZmCrwl-WT   TGCTCGGCTCCGGCCGGCGGCCGGCACGGACGACGACGACCTGGAGCTTCACGGGGTCGT
Zmcrwl-Ac   TGCTCGGCTCCGGCCGGCGGCCGGCACGGACGACGACGACCTGTGGAGCTTCACGCGGTCGT
            ************************************************************

1201......1211......1221......1231......1241......1251......1260
ZmCrwl-WT   CGGTTTCGTCGATCAGCGGCCGCGCGGCCAGGAGGCTCCAGGAGGGCCCACCAGCCAGCGTCAC
Zmcrwl-Ac   CGGTTTCGTCGATCAGCGGCCGCGCGGCCAGGAGGCTCCAGGAGGGCCCACCAGCCAGCGTCAC
            ************************************************************

1261 1265
ZmCrwl-WT   TGTAG
Zmcrwl-Ac   TGTAG
            *****
```

FIG. 7A

```
              1..........11..........21..........31..........41..........51........60
ZmCrw1-WT     ATGAGCATCTCGGTGAACGGAGCAGTCGTGCGTGCCGGGGTTCCGCTTCCAGCCCCACG
ZmCrw1-CO109  ATGAGCATCTCGGTGAACGGAGCAGTCGTGCGTGCCGGGGTTCCGCTTCCAGCCCCACG
              ************************************************************

61.........71..........81..........91.........101.........111.......120
ZmCrw1-WT     GAGGAGGAGCAGCTGCTCAACTACTACCTCCGCAAGAAGTGGCCTCCCAGGAGATCGACCTC
ZmCrw1-CO109  GAGGAGGAGCAGCTGCTCAACTACTACCTCCGCAAGAAGTGGCCTCCCAGGAGATCGACCTC
              ************************************************************

121........131.........141.........151.........161.........171.......180
ZmCrw1-WT     GACGTCATCCGGCAGTCGGAGACGTCGACCTCAACAGCTCGAGCCATGGACAATCCAAGAATGC
ZmCrw1-CO109  GACGTCATCCGGCAGTCGGAGACGTCGACCTCAACAGCTCGAGCCATGGACAATCCAAGAATGC
              ************************************************************

181........191.........201.........211.........221.........231.......240
ZmCrw1-WT     AAGATCGGTCGGGTCCCAGAACGACTACTCTTCAGCCACAAGGACAAGAAGAAGTAC
ZmCrw1-CO109  AAGATCGGTCGGGTCCCAGAACGACTACTCTTCAGCCACAAGGACAAGAAGAAGTAC
              ************************************************************

241........251.........261.........271.........281.........291.......300
ZmCrw1-WT     CCGACGGGAACGCCCACCAACCGCGTCGTCACGGCCGCCGGGTTCTGGAAGCCACGGGCCGC
ZmCrw1-CO109  CCGACGGGAACGCCCACCAACCGCGTCGTCACGGCCGCCGGGTTCTGGAAGCCACGGGCCGC
              ************************************************************

301........311.........321.........331.........341.........351.......360
ZmCrw1-WT     GACAAGGCCATCTACAACGCCGTCAAGGCATGGCATGGCAAGGCAGACGCTCGTCTTCTAC
ZmCrw1-CO109  GACAAGGCCATCTACAACGCCGTCAAGGCATGGCATGGCAAGGCAGACGCTCGTCTTCTAC
              ************************************************************

361........371.........381.........391.........401.........411.......420
ZmCrw1-WT     AAGGGAC-GCGCGGACGCCGAGAAGTCCGACTGGAATCACGAGTACCGCTGA
ZmCrw1-CO109  AAGGGCCCGGACGCCGAGAAGTCCGACTGGAATCACGAGTACCGCTGA
              ************************************************************
```

FIG. 7B

```
                 421.......431.......441.......451.......461.......471.......480
ZmCrw1-WT        CGACCCCGCTGCTGCTGCTGCCGGTGATCCGGTGATGCCGGTCCTGATCCGTGCTGATCCG
Zmcrw1-CO109     CGACCCCGCTGCTGCTGCTGCCGGTGATCCGGTGATGCCGGTCCTGATCCGTGCTGATCCG
                 ************************************************************

481.......491.......501.......511.......521.......531.......540
ZmCrw1-WT        CGCCACCGGCTGCTGCTGCCGCCGCGGCTGCTGCCGCCGCGGCTGCTGCCGCCGCGGCTGCT
Zmcrw1-CO109     CGCCACCGGCTGCTGCTGCCGCCGCGGCTGCTGCCGCCGCGGCTGCTGCCGCCGCGGCTGCT
                 ************************************************************

541.......551.......561.......571.......581.......591.......600
ZmCrw1-WT        GGTGTGCAGGGTGTTCAAGAAGAAGCACCACCAAGGAGTCAGGTGGGGGCGGGGGGCAA
Zmcrw1-CO109     GGTGTGCAGGGTGTTCAAGAAGAAGCACCACCAAGGAGTCAGGTGGGGGCGGGGGGCAA
                 ************************************************************

601.......611.......621.......631.......641.......651.......660
ZmCrw1-WT        CAAGCACGGCAGCAGCAGTAACAGCGAGCAGCAGCAGCACGGCCGGAGCCGCAAGGCATGGCTGC
Zmcrw1-CO109     CAAGCACGGCAGCAGCAGTAACAGCGAGCAGCAGCAGCACGGCCGGAGCCGCAAGGCATGGCTGC
                 ************************************************************

661.......671.......681.......691.......701.......711.......720
ZmCrw1-WT        GGCTGCCGGCTGCGGGCGCACCAGCACCATGGAGGCCTGCAGTACTGCAGTACTCCTCCAGCGA
Zmcrw1-CO109     GGCTGCCGGCTGCGGGCGCACCAGCACCATGGAGGCCTGCAGTACTGCAGTACTCCTCCAGCGA
                 ************************************************************

721.......731.......741.......751.......761.......771.......780
ZmCrw1-WT        CGAGACGCTGGACCAGATCCTGCAGTACATGGGCAGGTCGTGCAAGCAGGAGCACGAGCT
Zmcrw1-CO109     CGAGACGCTGGACCAGATCCTGCAGTACATGGGCAGGTCGTGCAAGCAGGAGCACGAGCT
                 ************************************************************

781.......791.......801.......811.......821.......831.......840
ZmCrw1-WT        GGTGTCGCCGGCGCCGGCGCCGGGACGGGCGGGTCCAGTTACTTCCGGCCCAT
Zmcrw1-CO109     GGTGTCGCCGGCGCCGGCGCCGGGACGGGCGGGTCCAGTTACTTCCGGCCCAT
                 ************************************************************
```

FIG. 7C

```
ZmCrw1-WT    841.......851.......861.......871.......881.......891......900
             CGAGACCGTTCTGGGCGGGCACGCGTTCATGATGAGCTTCCCGGCTCCGAGAGCCCGTCCGC
ZmCrw1-CO109 CGAGACCGTTCTGGGCGGGCACGCGTTCATGAAGACTTCCCGGCTCCGAGAGCCCGTCCGC
             ************************************************************

ZmCrw1-WT    901.......911.......921.......931.......941.......951......960
             GGCCCGGTCCGCATCGGTGACACAGCGGGGCGGCCAGCGAGCTCTACCGGCGGCCGCCGG
ZmCrw1-CO109 GGCCCGGTCCGCATCGGTGACACAGCGGGGCGGCCAGCGAGCTCTACCGGCGGCCGCCGG
             ************************************************************

ZmCrw1-WT    961.......971.......981.......991.......1001......1011.....1020
             GAACGGGATCACGGACTGGGCCATGATGGACCGGCGTGGCGTCGCAACTGAACGGGCA
ZmCrw1-CO109 GAACGGGATCACGGACTGGGCCATGATGGACCGGCGTGGCGTCGCAACTGAACGGGCA
             ************************************************************

ZmCrw1-WT    1021......1031......1041......1051......1061......1071.....1080
             GCAGGCGCGCCGCGCGGGACAGTCGGCGGCGACGCCTGCGGCTCGACGCGGACGCCGG
ZmCrw1-CO109 GCAGGCGCGCCGCGCGGGACAGTCGGCGGCGACGCCTGCGGCTCGACGCGGACGCCGG
             ************************************************************

ZmCrw1-WT    1081......1091......1101......1111......1121......1131.....1140
             CGTCCGCGGCGGAGAGCGGACGCGGACGCCGGCCTCGCCTTCTACTCGCGCCAGCGGCTGCTCGG
ZmCrw1-CO109 CGTCCGCGGCGGAGAGCGGACGCGGACGCCGGCCTCGCCTTCTACTCGCGCCAGCGGCTGCTCGG
             ************************************************************

ZmCrw1-WT    1141......1151......1161......1171......1181......1191.....1200
             CTCCGGCGGCGGCGGCGGCGCCGGCAGCAGCGACGACCTTGTGGAGCTTCAACGGGTTCGTCGGTTTC
ZmCrw1-CO109 CTCCGGCGGCGGCGGCGGCGCCGGCAGCAGCGACGACCTTGTGGAGCTTCAACGGGTTCGTCGGTTTC
             ************************************************************

ZmCrw1-WT    1201......1211......1221......1231......1241......1251.....1258
             GTCAACGGCGGCGGCGGCGGCCACGGAGCGGTCAGCGAGCGGTCAGCCACGTGTCACTGTAG
ZmCrw1-CO109 GTCAACGGCGGCGGCGGCGGCCACGGAGCGGTCAGCGAGCGGTCAGCCACGTGTCACTGTAG
             ************************************************************
```

```
WT     GCCGGGACGGGCGGCGGCGTCCAGGTACCTCCGGCCCATCGAGACCGTTCTGGGCGGGCA 848
NC316  GCCGGGACGGGCGGCGGCGTCCAGGTACCTCCGGCCCATCGAGACCGTTCTGGGCGGGCA 900
       ************************************************************

WT     CGCGTTCATGAAGCTGCCCCGCGCTCGAGAGCCCGTCCGCGGCCGCGGCCGCATCGCTGAC 908
NC316  CGCGTTCATGAAGCTGCCCCGCGCTCGAGAGCCCGTCCGCGGCCGCGGCCGCATCGCTGAC 960
       ************************************************************

WT     ACAGCCGGCGCAGCACGACGAGCTCTACCGCGCCCCCGGGAACGGGATCACGGACTGGGC 968
NC316  ACAGCCGGCGCAGCACGACGAGCTCTACCGCGCCCCCGGGAACGGGATCACGGACTGGGC 1020
       ************************************************************

WT     CATGATGGACCGGCTGGTGCGTCGCACCTGAAACGGCAGCAGGCCCCGCGCCCGCGGCGGA 1028
NC316  CATGATGGACCGGCTGGTGCGTCGCACCTGAAACGGCAGCAGGCCCCGCGCCCGCGGCGGA 1080
       ************************************************************

WT     CCAGCTCGGCGCGGCGGCTTGCGGCTTCGACGCGGAGCGCCGCCGAAGACGCCGACGCCGG 1088
NC316  CCAGCTCGGCGCGGCGGCTTGCGGCTTCGACGCGGAGCGCCGCCGAAGACGCCGACGCCGG 1140
       ************************************************************

WT     CCTCGCCTTCTACTCCGCCGCCGCCGGCTCCGGCTGCTCGGCTCCGGCGGCGCCGCGGCAG 1148
NC316  CCTCGCCTTCTACTCCGCCGCCGCCGGCTCCGGCTGCTCGGCTCCGGCGGCGCCGCGGCAG 1200
       ************************************************************

WT     CGACGACGACCTGTGGAGCTTCACGCGGTCGTCGGTTTCGTCAACGGCGGCGGCGGCGGC 1208
NC316  CGACGACGACCTGTGGAGCTTCACGCGGTCGTCGGTTTCGTCAACGGCGGCGGCGGCGGC 1260
       ************************************************************

WT     CACGTCCACGGAGCGGCTCAGCCACGTCACTGTAG 1245
NC316  CACGTCCACGGAGCGGCTCAGCCACGTCACTGTAG 1297
       ***********************************
```

FIG. 9B

```
                 70        80        90       100       110       120
                 |         |         |         |         |         |
DIQE.C.IG..PQN.WY..SHKDKKYPTGTRNRAT..GFWKATGRCK.I.........G Consensus #1 (SEQIDNO33)
DIQEKCKIGST=QNDWYFFSHKDKKYPTGTRNRATAAGFWKATGRCKAIYSX--XRRIG Majority (SEQIDNO34)

55  DIQEKCKIGSF=QNDWYFFSHKDKKYPTGTRNRATAAGFWKATGRCKAIYNA---VKRIG Zm  (SEQIDNO3)
55  DIQEKCKIGSF=QNDWYFFSHKDKKYPTGTRNRATAAGFWKATGRCKAIYNA---VHRIG Os  (SEQIDNO10)
55  DIQEKCRIGSF=QNDWYFFSHKDKKYPTGTRNRATAAGFWKATGRCKAIYSS---SNRIG Os  (SEQIDNO11)
55  DIQEKCKIGSF=QNDWYFFSHKDKKYPTGTRNRATAAGFWKATGRCKAIYNA---VKRIG Sb  (SEQIDNO12)
55  DIQEKCKIGSF=QNDWYFFSHKDKKYPTGTRNRATAAGFWKATGRCKAIYAS--GARRIG Sb  (SEQIDNO13)
59  DIQEKCKIGTF=QNDWYFFSHKDKKYPTGTRNRATAAGFWKATGRCKVIYSN---GKRIG Gm  (SEQIDNO14)
59  DIQEKCKIGTF=QNDWYFFSHKDKKYPTGTRNRATAAGFWKATGRCKVIYSN---GKRIG Gm  (SEQIDNO15)
60  DIQEMCKIGTF=QNDWYFFSHKDKKYPTGTRNRATAAGFWKATGRCKIIYSN---GRRIG At  (SEQIDNO16)
60  DIQEECRIGSF=QNDWYFFSHKDKKYPTGTRNRATVAGFWKATGRCKIECSC--VRRIG At  (SEQIDNO17)
55  DIQEKCRIGSF=QNDWYFFVSHKDKKYPTGTRNRATTVGFWKATGRCKAIYTN--GURIG Zm  (SEQIDNO18)
55  DIQEKCKIGSF=QNDWYFFSHKDKKYPTGTRNRATAAGFWKATGRCKAIYSA---VRRMG Zm  (SEQIDNO19)
55  DIQEKCRIGSF=QNDWYFFSHKDKKYPTGTRNRATAAGFWKATGRCKAIYASPGARRIG Zm  (SEQIDNO20)
55  DIQEKCKIGSF=QNDWYFFSHKDKKYPTGTRNRATAAGFWKATGRCKAIYNA---VSRIG Bd  (SEQIDNO21)
59  DIQEKCKIGTF=QNDWYFFSHKDKKYPTGTRNRATAAGFWKATGRCKVIYSS---FKRIG Vv  (SEQIDNO22)
59  DIQEKCKIGTF=QNDWYFFSHKDKKYPTGTRNRATAAGFWKATGRCKVIYSN---GKRIG Gm  (SEQIDNO23)
55  DIQEKCRIGSF=QNDWYFFSHKDKKYPTGTRNRATTVGFWKATGRCKIIYSG---FRRIG Gh  (SEQIDNO24)
60  DIQEKCRIGSF=QNDWLFSHKDKKYPTGTRNRATTVGFWKATGRCKIIYSG---FKRIG Pm  (SEQIDNO25)
55  DIQEKCRIGTGF=QNDWYFFSHKDKKYPTGTRNRATTVGFWKATGRCKAIYPAAGYGHIG Hv  (SEQIDNO26)
59  DIQEMCKIGTF=QNDWYFFSHKDKKYPTGTRNRATAAGFWKATGRCKTIYSN---GRRIG At  (SEQIDNO27)
```

FIG. 9C

```
                    130       140       150       160       170       180
                     |         |         |         |         |         |
         .RKTLVFY.GRAPHG.KSDWIMHEYRL..........................PYTADX....... Consensus #1 (SEQIDNO33)
         MRKTLVFYKGRAPHGQKSDWIMHEYRLCDP---------------------PYTADX.......... Majority (SEQIDNO34)

113  MRKTLVFYKGRAPHGQKSDWIMHEYRLDDPAAAAAAGSG------------DAVANDDAAATA  Zm(SEQIDNO3)
113  MRKTLVFYKGRAPHGQKSDWIMHEYRLDDPATDTAAAT-------------PTVTSAAAA    Os(SEQIDNO10)
113  MRKTLVFYKGRAPHGQKSDWIMHEYRLDDP---SSASAS------------VSVNLPSYYSSS Os(SEQIDNO11)
113  MRKTLVFYKGRAPHGQKSDWIMHEYRLDDPAAASGDAAA------------AATAAAAAT    Sb(SEQIDNO12)
114  MRKTLVFYKGRAPHGQKSDWIMHEYRLEPALDVDAAAGSASAHHAAAGAAADHHPYYTSS    Sb(SEQIDNO13)
117  MRKTLVFYKGRAPHGQKSDWIMHEYRLDD-----------------------NNTSDI     Gm(SEQIDNO14)
117  MRKTLVFYKGRAPHGQKSDWIMHEYRLDD-----------------------NNTADT     Gm(SEQIDNO15)
118  MRKTLVFYKGRAPHGQKSDWIMHEYRLDDNIIS-----------------------PEDVTV At(SEQIDNO16)
118  LRKTLVFYKGRAPHGQKSDWIMHEYRLDDT--------------------------PMSNGY At(SEQIDNO17)
118  MRKTLVFYKGRAPHGQKSDWIMHEYRLDESVLI-----------------------SSCGDH At(SEQIDNO18)
113  MRKTLVFYKGRAPHGHKSDWIMHEYRLDDD-----A--------------------AAVAAT Zm(SEQIDNO19)
113  MRKTLVFYKGRAPHGQKSDWIMHEYRLEAP---VDAGAG----AAHHLLL-PAAAEHPYYTSP Zm(SEQIDNO20)
115  MRKTLVFYKGRAPHGQKSDWIMHEYRLLDADDSSSAAT-----------------PYYTSS  Zm(SEQIDNO21)
113  MRKTLVFYKGRAPHGIJKSDWIMHEYRLLDADDSSSAAT----------AAMVRVSVTASS  Bd(SEQIDNO22)
117  MRKTLVFYKGRAPHGQKSDWIMHEYRLEEN--------------------------TPVHD  Vv(SEQIDNO23)
117  MRKTLVFYKGRAPHGQKSDWIMHEYRLDD-----------------------NNTADT     Gm(SEQIDNO24)
113  LRKTLVFYKGRAPHGQKSDWIMHEYRLDDN--------------------------TITHD Gh(SEQIDNO25)
118  LRKTLVFYKGRAPHGQKSDWIMHEYRLEES--------------------------NSTHD Pm(SEQIDNO26)
115  MRKTLVFYQGRAPHGHKSDWIMHEYRLDDA--TTPGNN--PAN----QAIGNAPYYPGS    Hv(SEQIDNO27)
117  MRKTLVFYKGRAPHGQKSDWIMHEYRLDDNIIS-----------------------PEDVTV At(SEQIDNO28)
```

```
         .....1.........................................LP Consensus #1(SEQIDNO33)
         DQILQ-YMGRS----CKQEHELEXX------------RXTSRXNXX-------GG-HRFMKLP Majority(SEQIDNO34)
              310       320        330         340         350       360
244      DQILQ-YMGRS----CKQEHELVSPAPAPPGR-----------AAASRYLRPIETVIGG-HAFMKLP Zm(SEQIDNO3)
219      DQILQ-YMGRS----CKQEHELPSPQASGGGAGAGSHPASRYLRPIDTVIGG-HGFMKLP Os(SEQIDNO10)
246      DHILQ-YMGRSG---CKQETKPAAMSASS-----AAAAAALEQHLSTP-------QYGKFMKLP Os(SEQIDNO11)
238      DQILQ-YMGRS----CKQEHELLSPP--PPG------------RAASRYLRPIETVIGG-HGFMKLP Sb(SEQIDNO12)
272      DHILQ-YMGGG-GKQPDTKPVLLDHHHHHLAAAATT--TACSAGGA--GLYGKFMKLP Sb(SEQIDNO13)
206      EQILQ-QMGRG----CKEFSSYEGNYNSYGRFA-----------MGLNNGGGG--GYNDRFMKLP Gm(SEQIDNO14)
206      EQILE-QMGRS----CKEESSYEGNYRNYGRFTRP-YETTGLNNGG--GYNDRFMKLP Gm(SEQIDNO15)
217      DQFLE-IMGRS----CKEELNIDP-------------------------FMKLP At(SEQIDNO16)
216      DHVLL-YMDRT----GSNICMPES-------------QTTQHQ-------DDVLFMQLP At(SEQIDNO17)
202      EQILE-VMGQS----CKGEIVIDP-------------------------FLKLP At(SEQIDNO18)
222      DHMEG---RRS----CKQEHELLPLP--PPAAA----------RAASRYLRPIETVIGG-HGFMKLP Zm(SEQIDNO19)
287      DHILQQYMGGGRQAPAPDTKPALLEQLDHLHHLAAAPT-RAAAG---FYYGKFMKLP Bd(SEQIDNO20)
227      DQTIH-YMGRSSAACKQEHDSPRPAPAQTQAC-ARPTSRYLRPIETALAGGHGFMKLP Bd(SEQIDNO21)
208      DQIIS-YMGRT----CKQENEAISNVN-FSDSNNT-MRFLNQNTGISE--GLQEREMHLP Vv(SEQIDNO22)
206      EQILE-QMGRS----CKEESSYEGNYRNYGRFTRP-YETTGLNNGG--GYNDRFMKLP Gm(SEQIDNO23)
207      DQILH-YMGRT----CKMESDSLNNINNIPIPDNN-PRMLVGNNGGINDGFHDHERFMHLP Gh(SEQIDNO24)
209      DQIIM-YMGRT----CKLENHDP--------------LFMNN---------ISERFMHLP Pm(SEQIDNO25)
257      DHILNQYMHGRS---STTTSCKKETNAT--NPSSSALDHLINSECHN--VSSTLYEKLP Hv(SEQIDNO26)
216      DQFLE-IMGRS----CKEELNIDP-------------------------FMKLP At(SEQIDNO27)
```

FIG. 9G

```
      370        380        390        400        410        420
.LE...........................................IEXPHXISXDYN-N--------  Consensus #1(SEQIDNO33)
PLESPXSAS-------------------------IEXPHXISXDYN-N--------              Majority(SEQIDNO34)

294 ALESPSAMAS----------------------ASLTQPAQH---------------           Zm(SEQIDNO3)
274 PLESRSAATA----------------------LSSTPSTGEDAASS----------           Os(SEQIDNO10)
294 PLEHVAGGVG----------------------LLAAASGGGEYCS----------            Os(SEQIDNO11)
285 PLESPSAAAAA---------------------MT-TQAVSG-DAGV--------             Sb(SEQIDNO12)
328 PLEHAGGGGG----------------------LLPSPAGACDYG----------             Sb(SEQIDNO13)
253 SLESPKSAS-----------------------MENHHNTNN-----N--------            Gm(SEQIDNO14)
256 SLESPKSAS---------------MESHHNTRNNNMMSNRNNVNGDNNENNNNN              Gm(SEQIDNO15)
241 NLESPNSQA----------------------INNCHVSSFDYINHN---------             At(SEQIDNO16)
251 SLETPKSESP----------------------VDQSFLTPSKLDFS---------            At(SEQIDNO17)
226 NLECHNNTT-----------------------ITSYQWLIDDQVNN---------            At(SEQIDNO18)
269 PLESPAAAEA----------------------LITTPHAVSAGDATA--------            Zm(SEQIDNO19)
342 PLEHAG--LP----------------------PSEPPGAREYG-----------             Zm(SEQIDNO20)
283 PLESPSSAAA----------------------AAPHNTTP--------------             Bd(SEQIDNO21)
260 RLESPTLPSLPNNSSHFDQERCFNTACLQSIDEMLRGSEPSSEN------                  Vv(SEQIDNO22)
256 SLESPKSAS---------------MESHHNTRNNNMMSMAANNGDNNENNNNN               Gm(SEQIDNO23)
262 RLESPTLPSL---------------------CYQSIFDMLTETEHRGGC------             Gh(SEQIDNO24)
242 RLESPTLPNLP-----AFDQDRSF-KACYQAIDDMFIETEPPSTN---------              Pm(SEQIDNO25)
310 PLEHVVP-GE----------------------LLEH--TEYS------------              Hv(SEQIDNO26)
240 NLESPNSQA---------------------INNCHVSSFDINHN----------              At(SEQIDNO27)
```

FIG. 9H

```
                         ..............D Consensus #1(SEQIDNO33)
                         ----ASNG-X-------------SGITDWA-ALD Majority(SEQIDNO34)
          430       440       450       460       470       480
          |         |         |         |         |         |
313   ----------------------------------DELYR-------AAGNGITDWA-MMD Zm(SEQIDNO3)
298   ------------------------------AAAAAADHLL-----LHHHHRTDWA-MMD Os(SEQIDNO_0)
317   ----------------------------------AADA-------SGIADWD-TLD Os(SEQIDNO11)
307   -------------------------------VDDLIQLRRG----GIGNGITDWA-RMD Sb(SEQIDNO12)
350   ----------------------------------AADA-------SGIADWD-ALD Sb(SEQIDNO_3)
272   -------------------------------CNNNMKS-------GGGITDWA-ALD Gm(SEQIDNO14)
295   GYHPMIPVEMGTDNEGSFTTHQVSGGDPNNNNNVHPL-----EVGSGGGITDWA-ALD Gm(SEQIDNO15)
264   ----------------------------------THVSNVVDT--SFVISWA-ALD At(SEQIDNO16)
275   --------------------------------PVQEKIT------ER-PVCSNWA-SLD At(SEQIDNO17)
249   --------------------------------CHVSKVMDP----GFTTSWA-ALD At(SEQIDNO18)
293   --------------------------------AGALDGLHR----AGNGITDWV-MMD Zm(SEQIDNO19)
362   ----------------------------------AAAA-------AGWDDDDALD Zm(SEQIDNO20)
301   ----------------------------------------------VPETTMDWA-MMD Bd(SEQIDNO21)
304   --------------------------QGS--GCN-----------TTPVHDPKAGLNDWV-AHD Vv(SEQIDNO22)
295   GYHPMIPVEMGTDNEGSFTTHQVSGGDPNNNNNVHPL-----EVGSGGGLTDWA-ALD Gm(SEQIDNO23)
290   --------------------------------CGCGNN-------ETKNGVNDWV-TLD Gh(SEQIDNO24)
281   -----------QQSNQCDNNELVDDHEDPKRRVNDWV-TLD Pm(SEQIDNO25)
327   ----------------------------------------------QDWD-ALD Hv(SEQIDNO26)
263   ----------------------------------THVSNVVDT--SFVISWA-ALD At(SEQIDNO27)
```

FIG. 9L

Consensus #1(SEQIDNO33)
Majority (SEQIDNO34)

Zm(SEQIDNO3)
Os(SEQIDNO10)
Os(SEQIDNO11)
Sb(SEQIDNO12)
Sb(SEQIDNO13)
Gm(SEQIDNO14)
Gm(SEQIDNO15)
At(SEQIDNO16)
At(SEQIDNO17)
At(SEQIDNO18)
Zm(SEQIDNO19)
Zm(SEQIDNO20)
Bd(SEQIDNO21)
Vv(SEQIDNO22)
Gm(SEQIDNO23)
Gh(SEQIDNO24)
Pm(SEQIDNO25)
Hv(SEQIDNO26)
At(SEQIDNO27)

418
400
395
419
428
388
419
365
358
334
379
435
408
405
400
389
401
411
395 QISLH

COMPOSITIONS AND METHODS CONFERRING RESISTANCE OF MAIZE TO CORN ROOTWORM 1

CROSS REFERENCE TO RELATED APPLICATIONS

The application is a National Phase Under 35 U.S.C. § 371 of PCT/US2013/061026 filed in the Patent Cooperation Treaty U.S. Receiving Office on Sep. 20, 2013, which claims the benefit of U.S. Provisional Application No. 61/703,396, filed Sep. 20, 2012, and of U.S. Provisional Application No. 61/781,057, filed Mar. 14, 2013, the entire contents of which are herein incorporated by reference.

REFERENCE TO SEQUENCE LISTING

The Sequence Listing submitted Jun. 14, 2017 as a text file named "36446_0195U1_Substitute_Sequence_Listing," created on May 15, 2017, and having a size of 89,893 bytes is hereby incorporated by referenced pursuant to 37 C.F.R. § 1.52(e)(5).

FIELD

The field relates to plant breeding and genetics and, in particular, relates to recombinant DNA constructs useful in maize plants for conferring resistance to corn rootworm.

BACKGROUND

The larval forms of three species of *Diabrotica* beetles, the Western corn rootworm (*Diabrotica virgifera virgifera* LeConte), the Northern corn rootworm (*Diabrotica barberi* Smith and *Diabrotica barberi* Lawrence), and the Southern corn rootworm (*Diabrotica undecimpunctata howardi* Barber), represent serious insect pests of corn in the Midwestern United States. Approximately 30 million acres (120,000 km²) of corn (out of 80 million grown) are infested with corn rootworms, the larvae of which can cause losses estimated by the United States Department of Agriculture on the order of about $1 billion per year.

There are many different management practices aimed at the control of corn rootworms, including corn variety selection, early planting, insecticides, crop rotation, and the use of transgenic corn varieties; however, none on its own has proven to effectively manage the pest. An additional complication exists in that corn rootworm insects have shown a remarkable ability to evolve resistance to several control measures, including insecticides, cultural practices, and resistance genes that have been introduced into plants.

Thus, there is a constant need for new mechanisms of corn rootworm resistance in maize that can be incorporated into an integrated pest management strategy.

SUMMARY

Methods of increasing resistance to herbivory by an insect pest in a maize plant are provided in which polynucleotides encoding CRW1 are expressed in maize plants.

Also provided are methods of identifying variants of ZmCrw1 (or ZmCRW1) that give maize plants increased resistance to herbivory by an insect pest and then further introducing the variants into the maize plants. The variants can be identified through gene shuffling experiments or can be naturally occurring allelic variants identified through linkage mapping or whole genome association analyses. Variants arising from gene shuffling can be transgenically introduced into maize plants to give them the increased resistance, while allelic variants identified using the methods presented herein can be incorporated into maize plants using molecular breeding.

In some embodiments, the insect pest is Coleopteran. In other embodiments, the Coleopteran insect pest is of the genus *Diabrotica*. In still other embodiments, the insect pest is a corn rootworm, including without limitation, the Western corn rootworm (*Diabrotica virgifera virgifera* LeConte), the Northern corn rootworm (*Diabrotica barberi* Smith and *Diabrotica barberi* Lawrence), and/or the Southern corn rootworm (*Diabrotica undecimpunctata howardi* Barber).

In some embodiments, the insect pest is Lepidopteran. In other embodiments, the Lepidopteran insect pest is European corn borer.

Isolated polynucleotides, recombinant constructs containing said polynucleotides, and plants and plant cells containing said recombinant constructs are also provided.

BRIEF DESCRIPTION OF THE DRAWINGS AND SEQUENCE LISTING

The disclosure can be more fully understood from the following detailed description and the accompanying drawings and Sequence Listing which form a part of this application.

Figure 3:
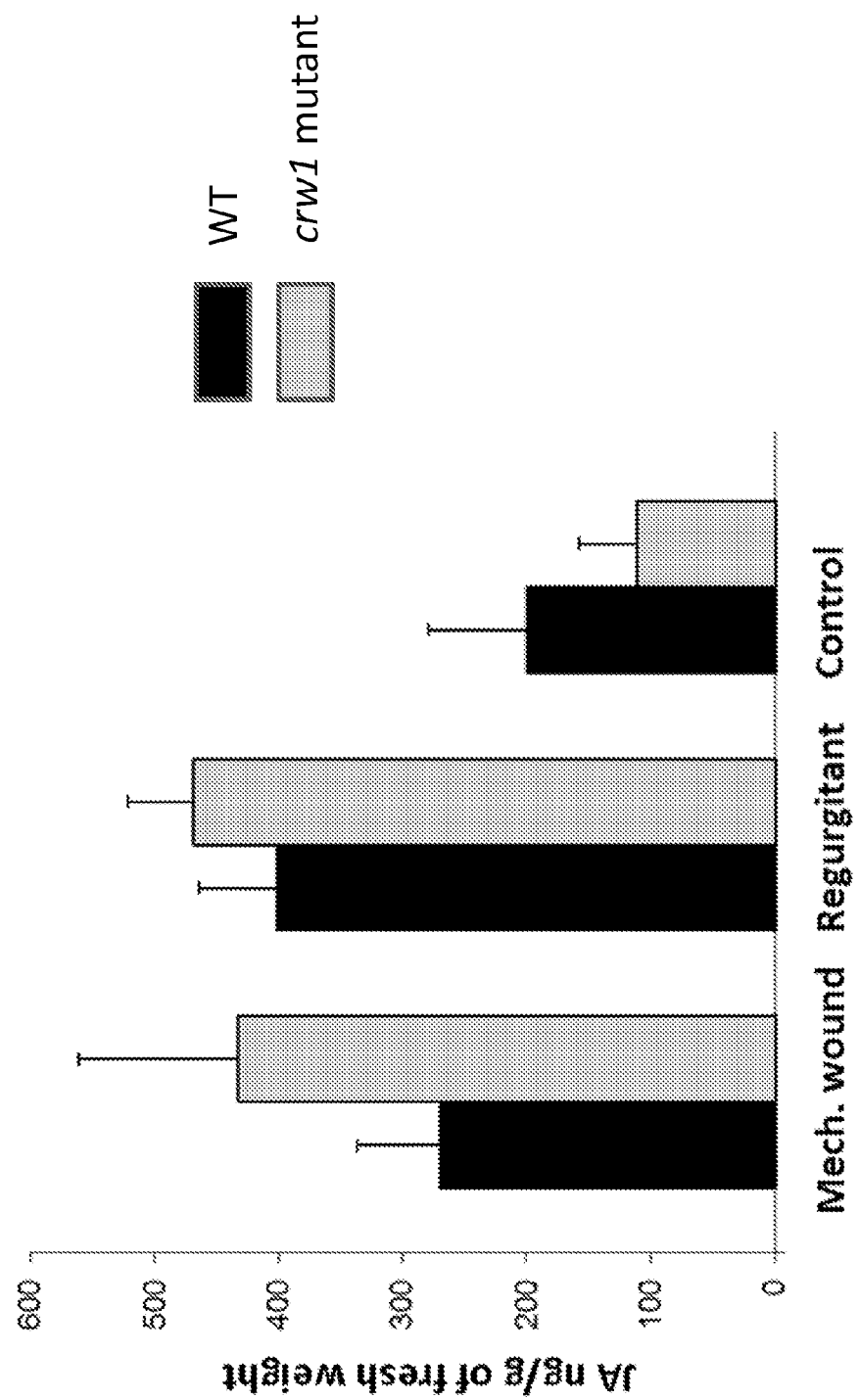

FIG. 3 depicts the quantification of Jasmonic Acid (JA) from the Crw1 mutant (MT) and wild type (WT) plants in response to mechanical wounding ("Mech. Wound") and Fall Armyworm caterpillar regurgitant ("Regurgitant"). Crw1 mutant plants accumulate higher levels of JA as compared to wild-type plants (WT), but only in response to applied stress.

Figure 4:
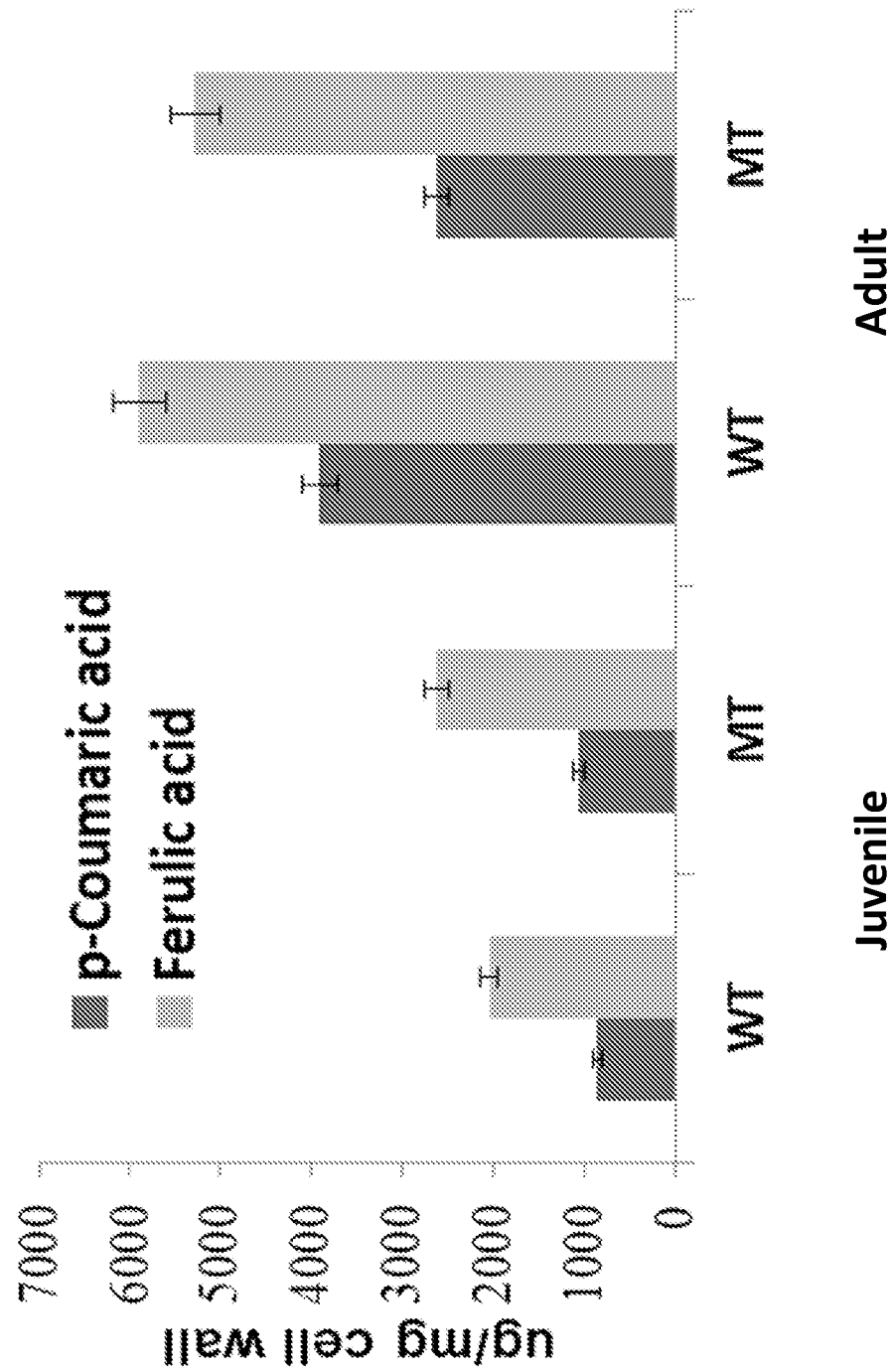

FIG. 4 depicts the differences in p-coumaric and ferulic acid levels from juvenile and adult leaves of Crw1 MT (mutant) and WT (wild-type) plants.

Figure 5:
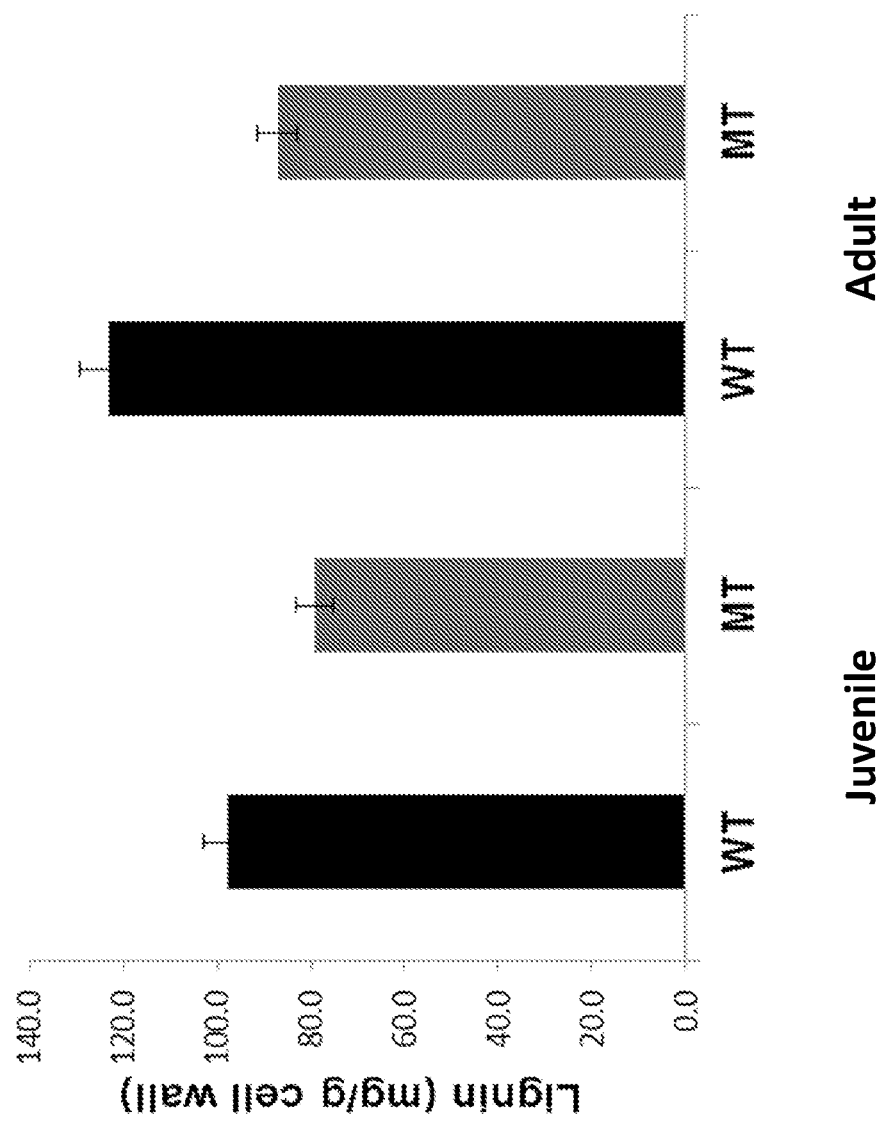
Figure 9A:
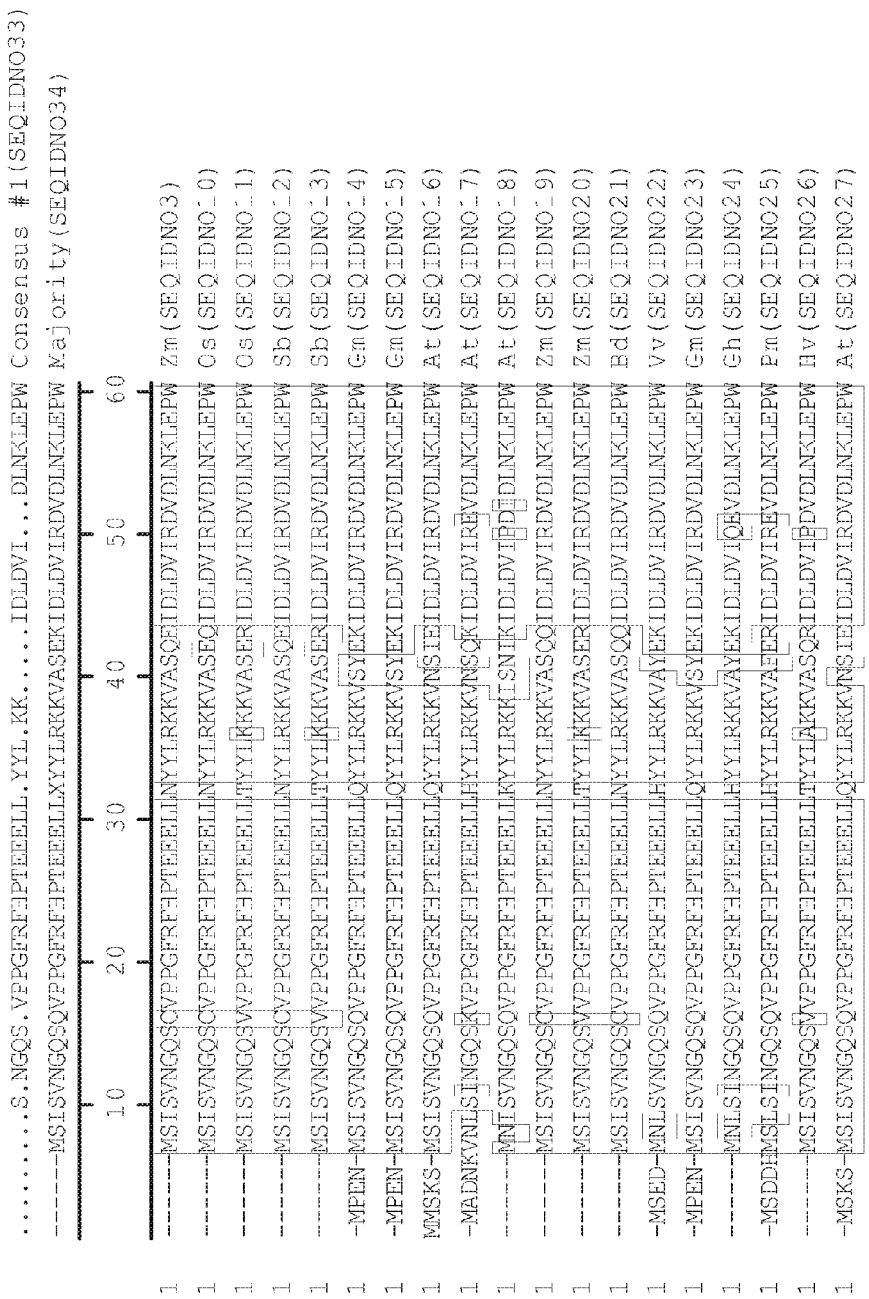
Figure 9E:
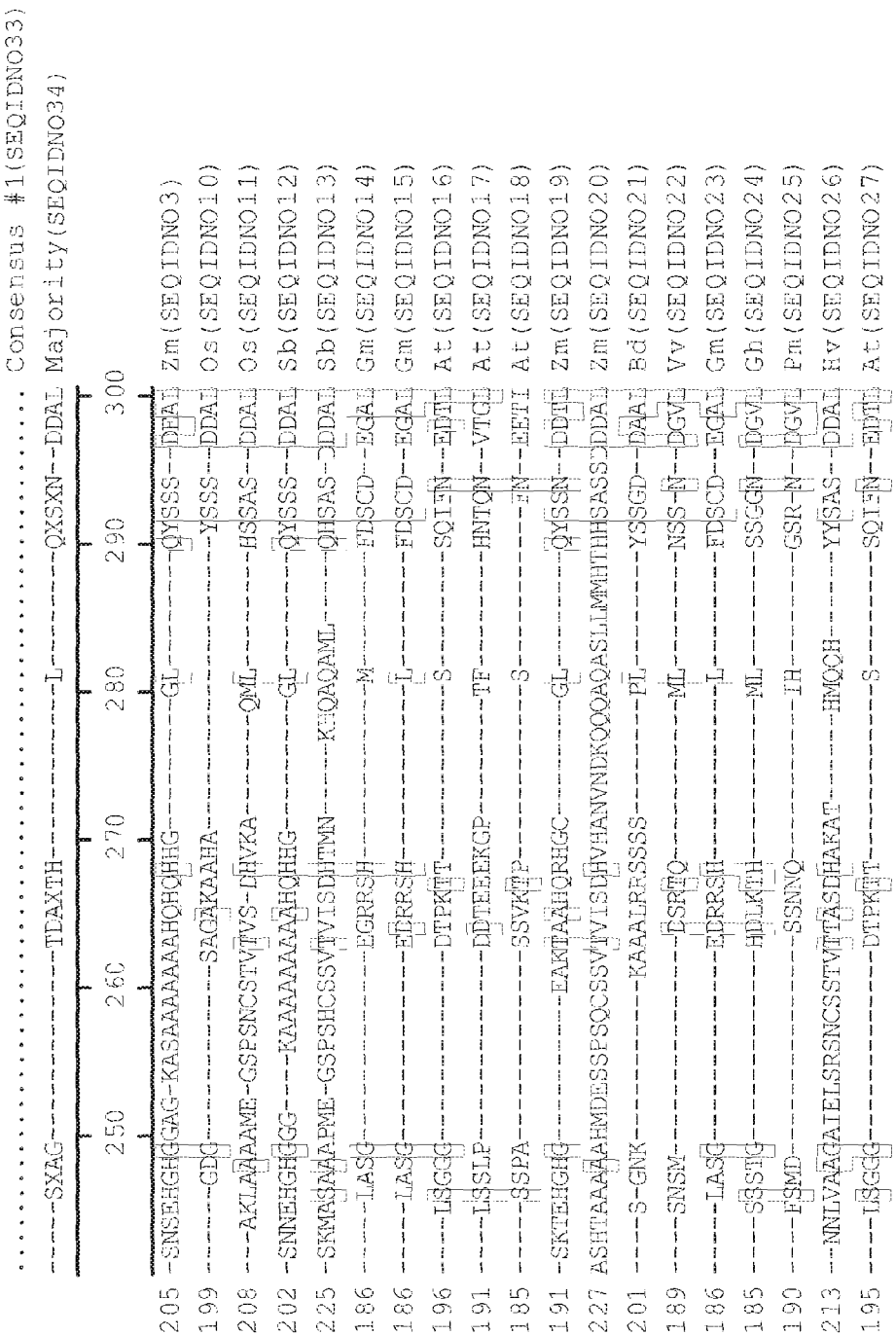
Figure 9I:
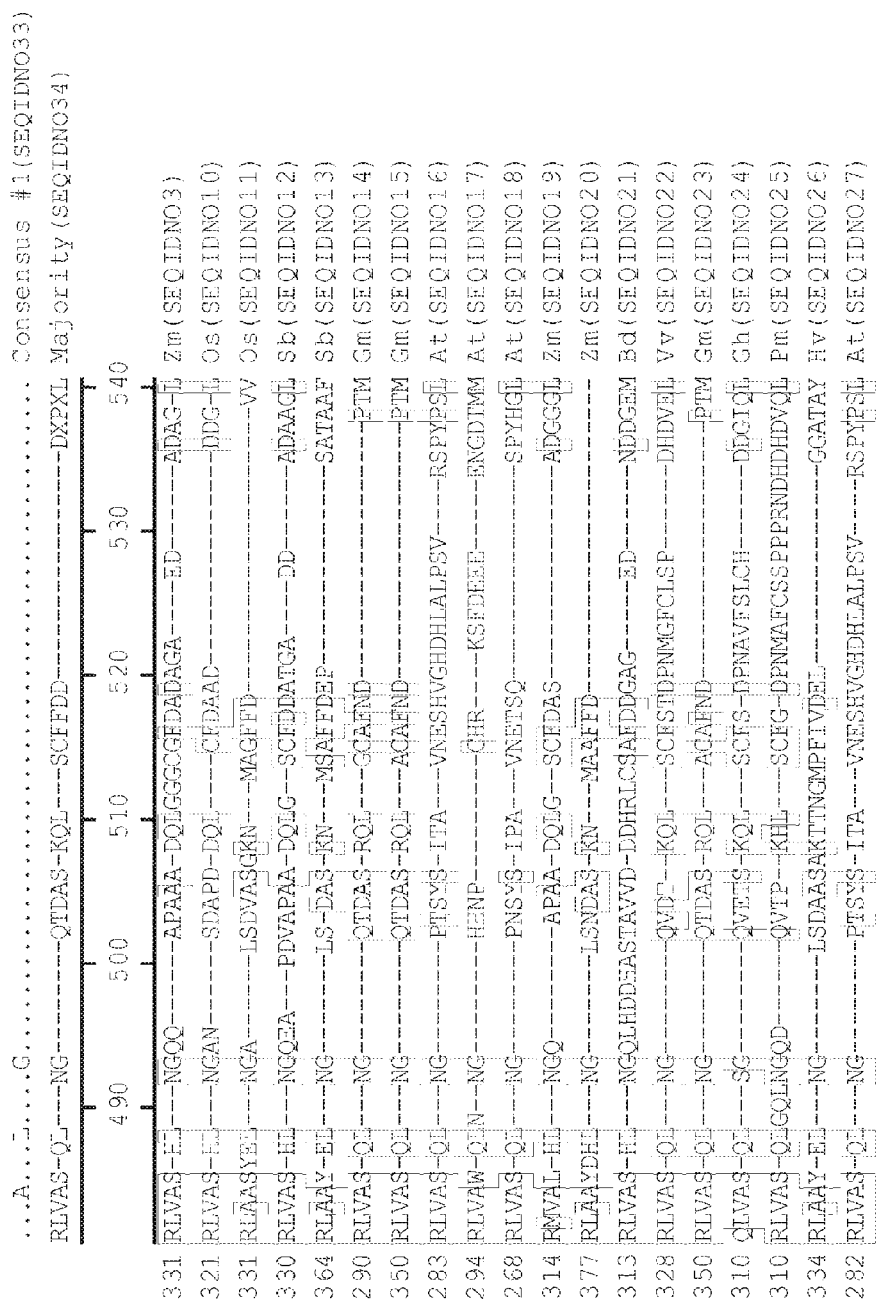
Figure 9J:
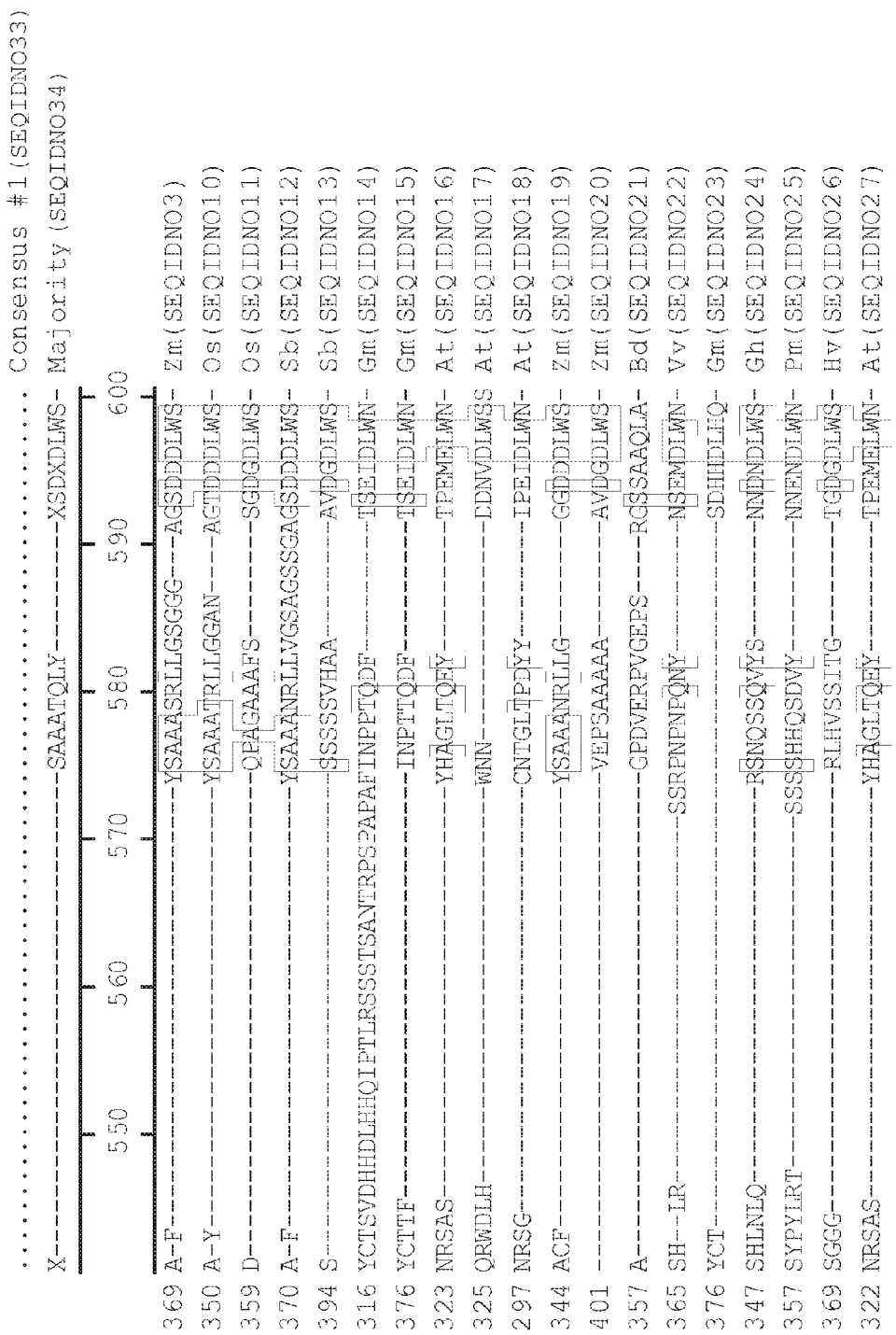
Figure 9K:
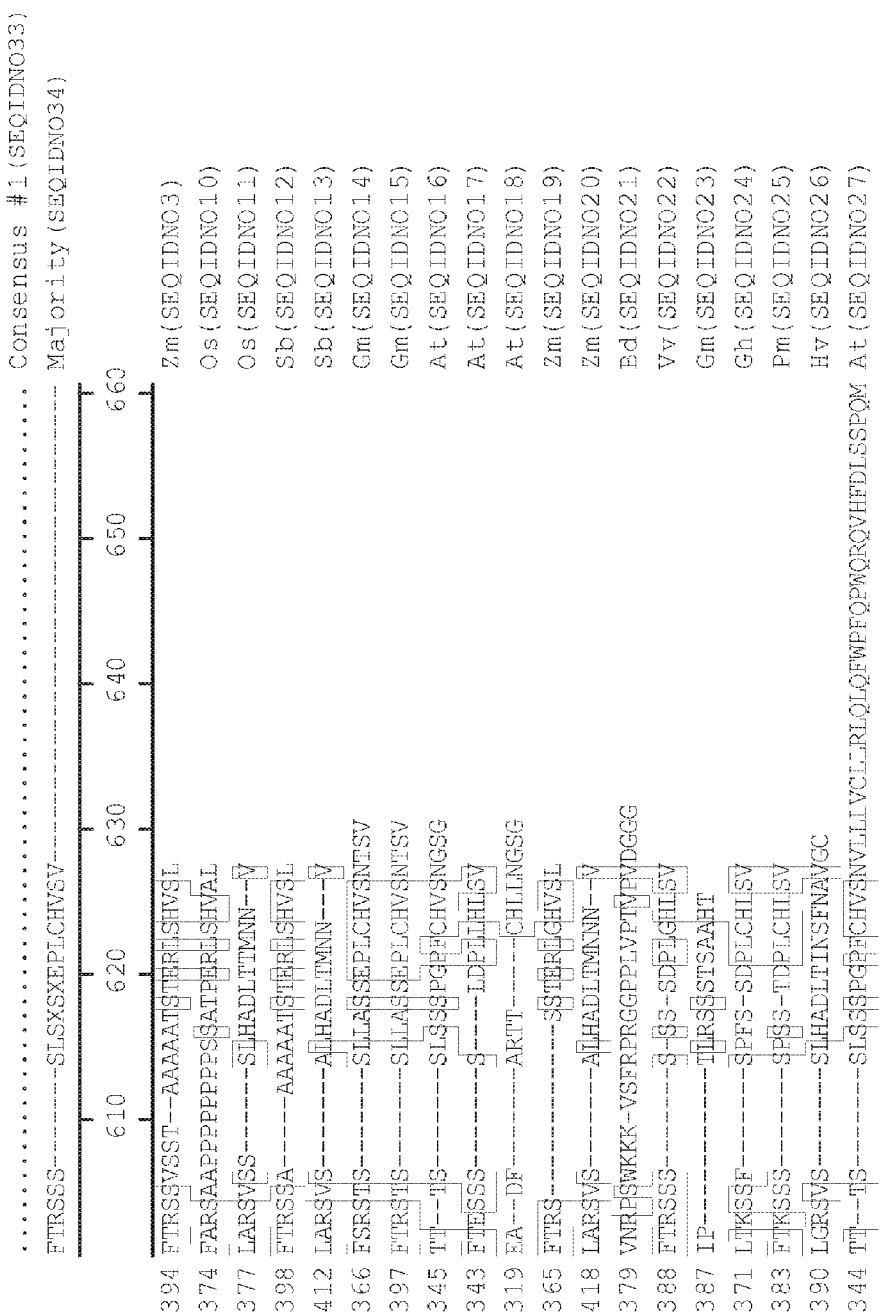

FIG. 5 depicts differences in the foliar lignin contents of Crw1 mutant (MT) and wild-type (WT) plants.

FIGS. 6A-6C show an alignment of the cDNA-sequences of Crw1 from a WT-Sib (SEQ ID NO:2) and the crw1-Ac mutant allele (SEQ ID NO:4), which is the result of excision of the autonomous Ac transposon present in the original allele. The 8 bp insertion (boxed) in exon1 leads to a premature termination in the predicted peptide chain at the site of insertion.

FIGS. 7A-7C show an alignment of cDNA-sequences of Crw1 from a WT-Sib (SEQ ID NO:33) and the crw1-00109 allele (SEQ ID NO:6). The crw1-00109 allele has an addition of 1 bp insertion and two other bp changes in exon2 as compared to its WT-sib (see the arrows in FIG. 7A indicating the positions of the insertion and bp changes). The insertion of 1 bp in exon2 results in premature termination of the CRW1 peptide.

Figure 8A:
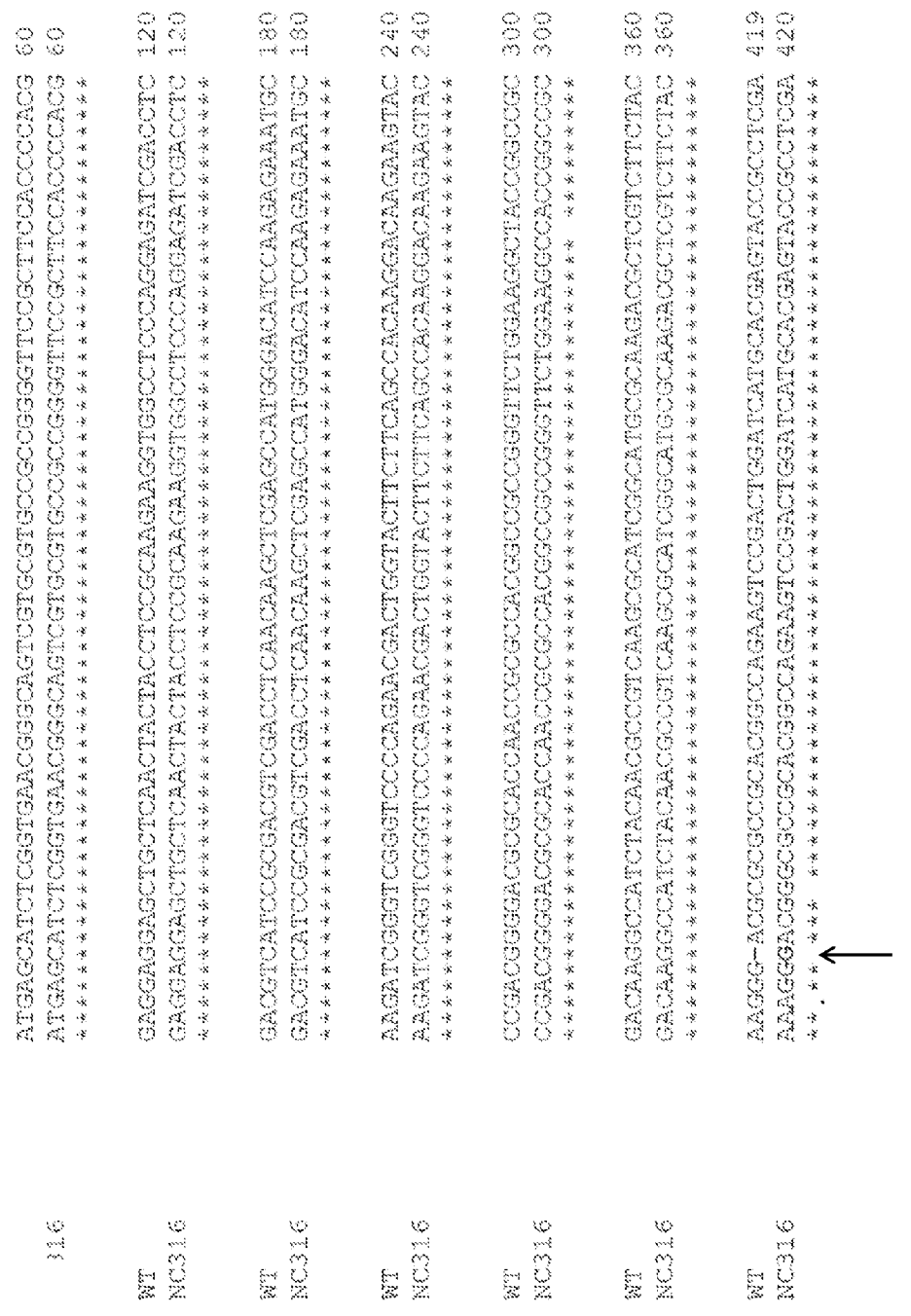
Figure 8B:
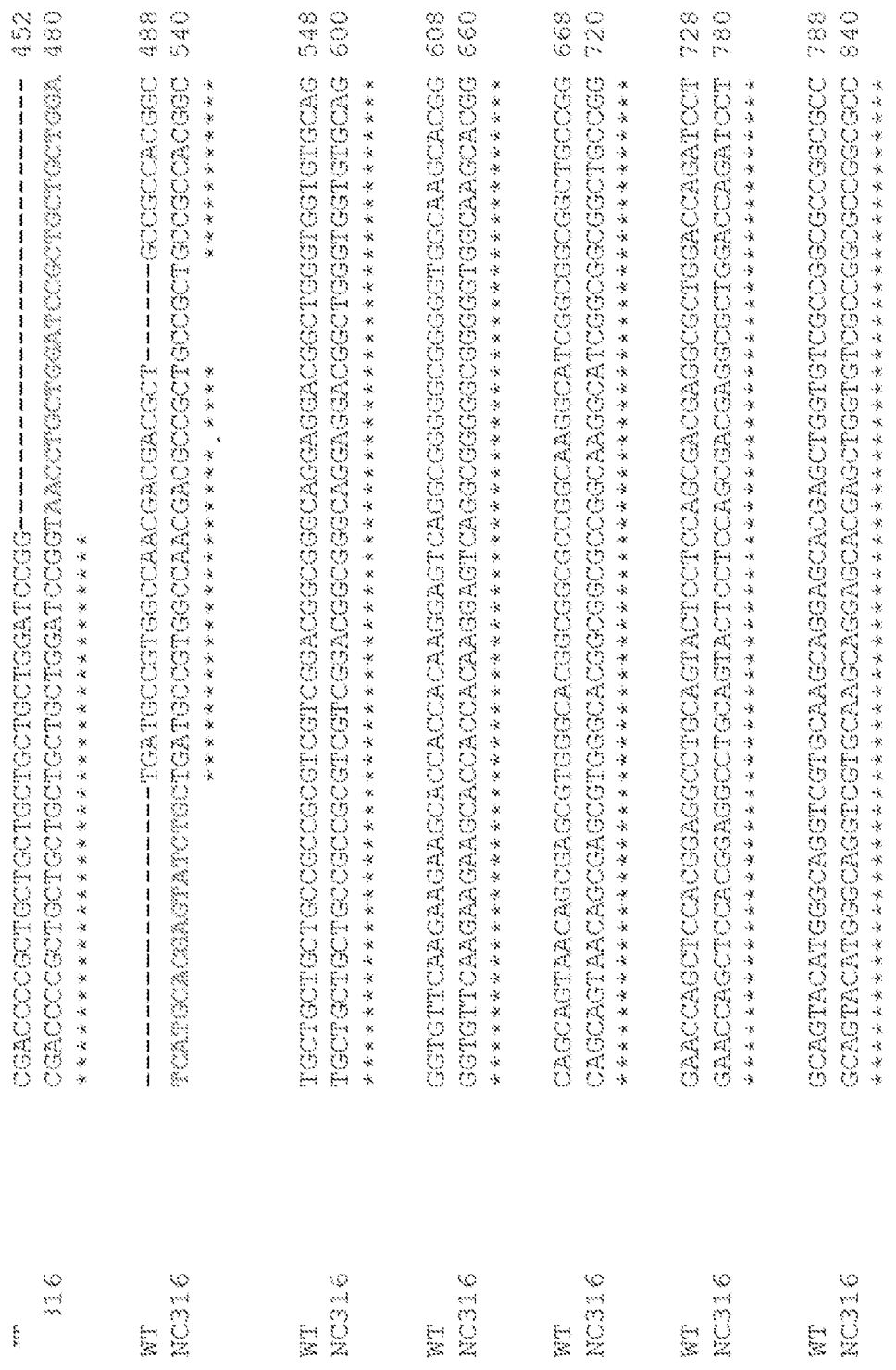

FIGS. 8A-8C show an alignment of the cDNA-sequences of Crw1 from a WT-Sib (SEQ ID NO:34) and the crw1-NC316 allele (SEQ ID NO:8). The crw1-NC316 allele has a 1 bp insertion (see arrow in FIG. 8A) and a 45 bp insertion in the second exon. The presence of the 1 bp insertion results in a premature termination codon at the site of the 45 bp insertion.

Figure 9D:
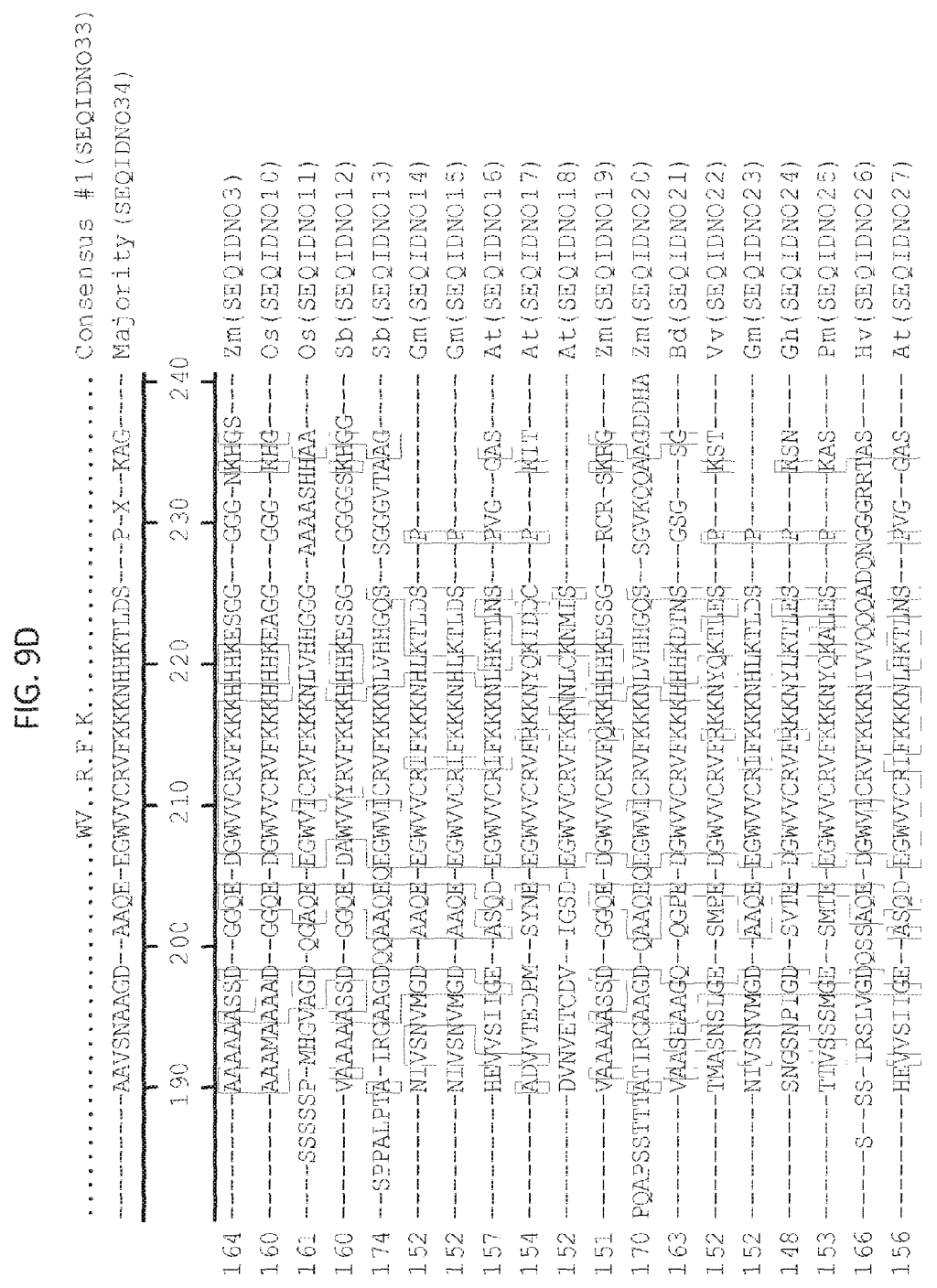

FIGS. 9A-9L show the multiple alignment of the amino acid sequences of the polypeptides of SEQ ID NOs:3, 10, 11, 12, 13, 14, 15, 16, 17, 18, 19, 20, 21, 22, 23, 24, 25, 26, and 27. When all residues at a position match the residue of the consensus sequence, the residue is shown; otherwise a "." is shown. In addition, residues that match the consensus exactly are boxed.

Figure 10:
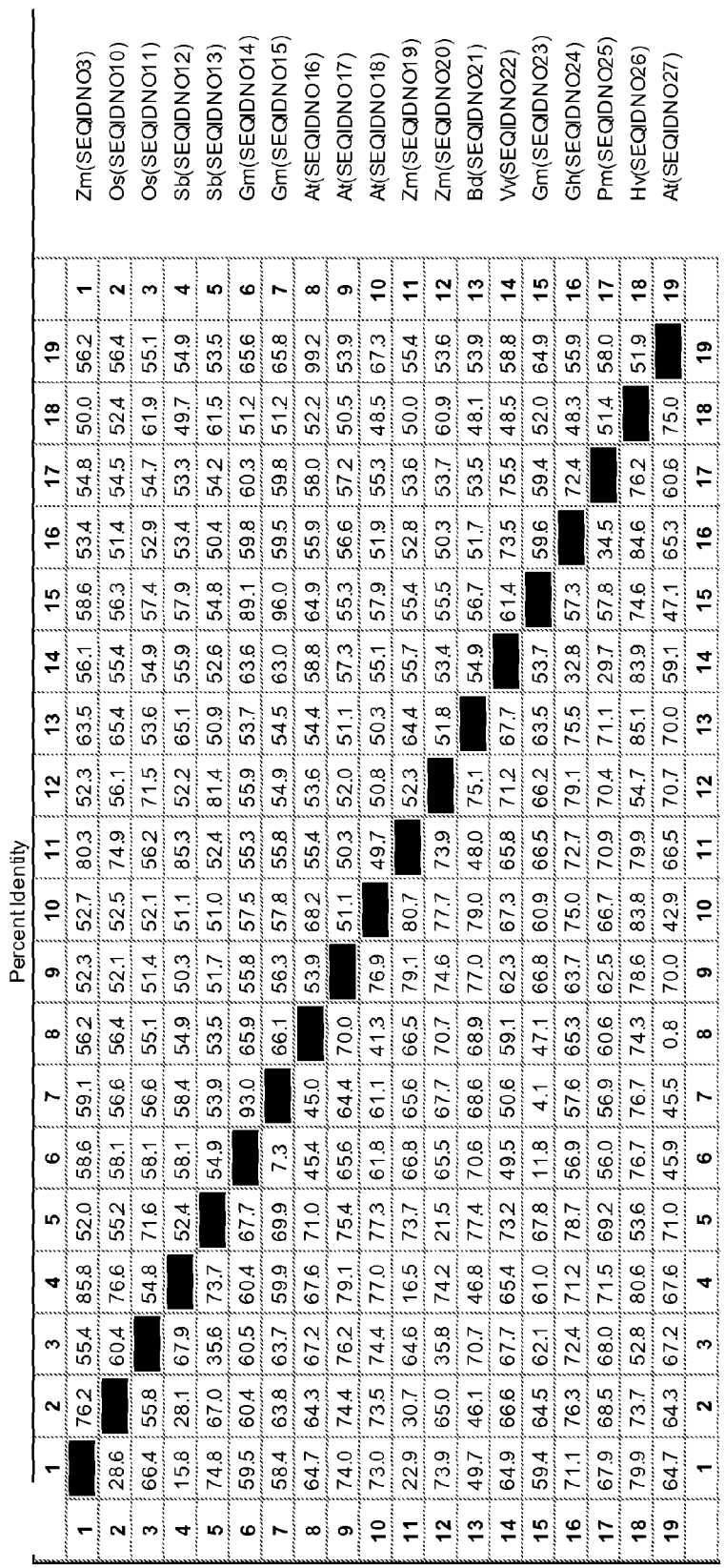

FIG. 10 shows the percent sequence identity and the divergence values for each pair of amino acids sequences of the polypeptides displayed in FIGS. 9A-9L.

Figure 11:
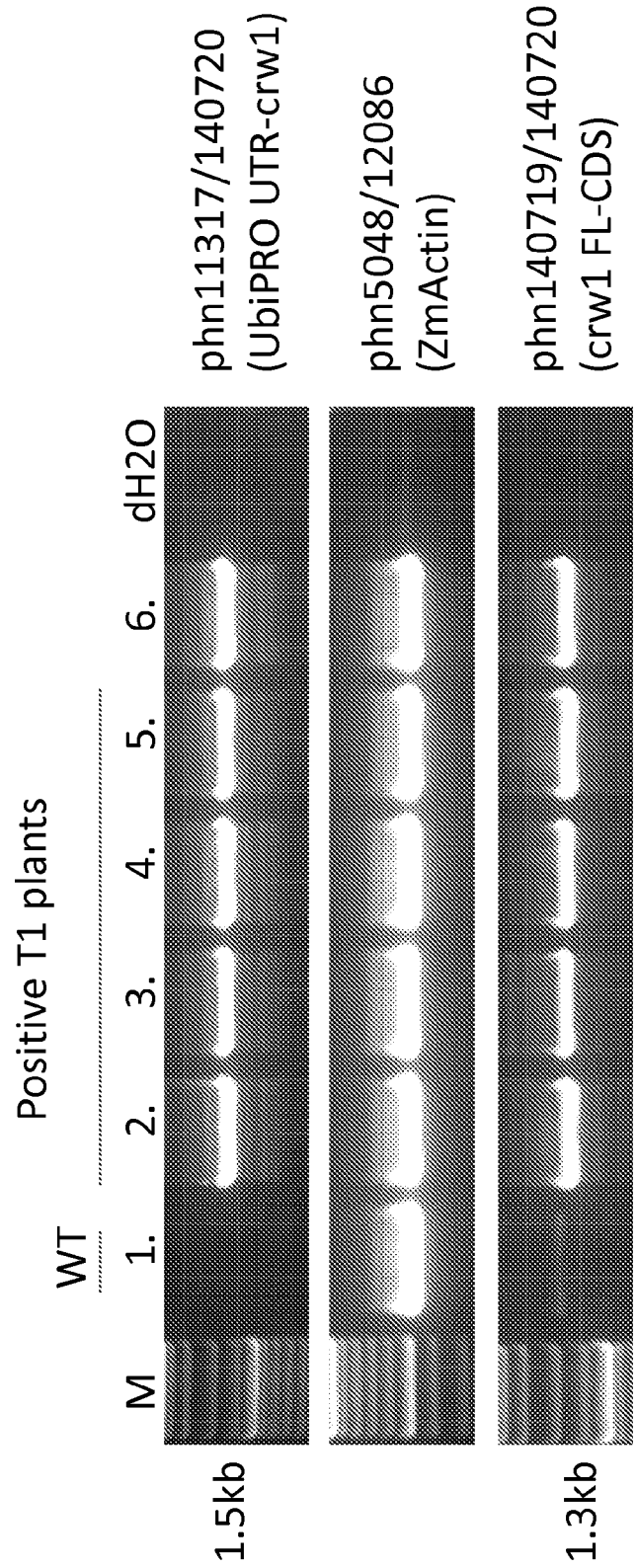

FIG. 11 shows the results of RT-PCR of event #8909.102.1.17.4 in T1 plants.

SEQ ID NO:1 is the nucleotide sequence of the genomic wild-type Zea mays Crw1.

SEQ ID NO:2 is the nucleotide sequence of the coding region of the wild-type Zea mays Crw1 (ZmCrw1) cDNA.

SEQ ID NO:3 is the amino acid sequence of the wild-type Zea mays CRW1 (ZmCRW1) protein.

SEQ ID NO:4 is the nucleotide sequence of the cDNA of the mutant crw1-Ac allele.

SEQ ID NO:5 is the amino acid sequence of the polypeptide encoded by the mutant crw1-Ac allele.

SEQ ID NO:6 is the nucleotide sequence of the Crw1 cDNA from maize inbred line CO109 (crw1-00109).

SEQ ID NO:7 is the amino acid sequence of the polypeptide encoded by SEQ ID NO:6.

SEQ ID NO:8 is the nucleotide sequence of the Crw1 cDNA from maize inbred line NC316 (crw1-NC316).

SEQ ID NO:9 is the amino acid sequence of the polypeptide encoded by SEQ ID NO:8.

SEQ ID NO:10 is the amino acid sequence of a secondary wall NAC transcription factor 2 from *Oryza sativa* (UniProt entry G3M8D2).

SEQ ID NO:11 is the amino acid sequence of a putative NAM protein (OsNAC7) from *Oryza sativa* (Identifier OS06g04090.1; UniProt entry Q9SNM6).

SEQ ID NO:12 is the amino acid sequence of a putative uncharacterized protein from *Sorghum bicolor* (Identifier Sb07g001550.1; UniProt entry C5YM23).

SEQ ID NO:13 is the amino acid sequence of a putative NAM protein from *Sorghum bicolor* (Identifier Sb10g002120.1; UniProt entry Q5NKS7).

SEQ ID NO:14 is the amino acid sequence of an uncharacterized protein from *Glycine max* (Identifier Glyma16g02200.1; UniProt entry I1MKD6).

SEQ ID NO:15 is the amino acid sequence of an uncharacterized protein from *Glycine max* (Identifier Glyma07g05660.1; UniProt entry I1KHQ4).

SEQ ID NO:16 is the amino acid sequence of a NAC domain-containing protein 43 from *Arabidopsis thaliana* (Identifier At2g46770.1; UniProt entry Q84WP6).

SEQ ID NO:17 is the amino acid sequence of a NAC domain-containing protein 12 from *Arabidopsis thaliana* (At1g32770.1; UniProt entry Q9LP17).

SEQ ID NO:18 is the amino acid sequence of a NAC domain-containing protein 66 from *Arabidopsis thaliana* (Identifier At3g61910.1; UniProt entry Q9M274).

SEQ ID NO:19 is the amino acid sequence of a secondary wall NAC transcription factor 2 from *Zea mays* (UniProt entry B4FPS5).

SEQ ID NO:20 is the amino acid sequence of a putative NAM protein from *Zea mays* (UniProt entry Q5NKQ3).

SEQ ID NO:21 is the amino acid sequence of a NAC domain-containing protein 43-like from *Brachypodium distachyon* (NCBI GI No. 357139497 and herein referred to as BdCRW1).

SEQ ID NO:22 is the amino acid sequence of a putative uncharacterized protein from *Vitis vinifera* (UniProt entry F6HU82).

SEQ ID NO:23 is the amino acid sequence of a NAC domain-containing protein 43-like from *Glycine max* (NCBI GI No. 356522480 and herein referred to as GmCRW1).

SEQ ID NO:24 is the amino acid sequence of a NAC domain-containing protein from *Gossypium hirsutum* (UniProt entry G4V2G0).

SEQ ID NO:25 is the amino acid sequence of a NAC domain class transcription factor (NAC12) from *Pyrus malus* (UniProt entry D9ZJ90).

SEQ ID NO:26 is the amino acid sequence of a predicted protein from *Hordeum vulgare* (UniProt entry F2DV83).

SEQ ID NO:27 is the amino acid sequence of a NAM-like protein from *Arabidopsis thaliana* (NCBI GI No. 3510262; UniProt entry Q84WP6).

SEQ ID NO:28 and SEQ ID NO:29 are the sense and antisense primers, respectively, used to amplify the Crw1 fragment from maize genomic DNA.

SEQ ID NO:30 is the nucleotide sequence of primer phn11317, which is a primer in the UBI promoter 5' UTR region of the transgene.

SEQ ID NO:31 is the nucleotide sequence of primer phn140720, which is at the Crw1-3' end and includes the stop codon.

SEQ ID NO:32 is the nucleotide sequence of primer phn140719, which is a primer in the 5' end of Crw1.

The sequence descriptions and Sequence Listing attached hereto comply with the rules governing nucleotide and/or amino acid sequence disclosures in patent applications as set forth in 37 C.F.R. § 1.821 1.825.

The Sequence Listing contains the one letter code for nucleotide sequence characters and the three letter codes for amino acids as defined in conformity with the IUPAC IUBMB standards described in Nucleic Acids Res. 13:3021 3030 (1985) and in the Biochemical J. 219 (No. 2):345 373 (1984) which are herein incorporated by reference. The symbols and format used for nucleotide and amino acid sequence data comply with the rules set forth in 37 C.F.R. § 1.822.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein.

The terms "dicot" and "dicotyledonous plant" are used interchangeably herein.

The terms "full complement" and "full-length complement" are used interchangeably herein, and refer to a complement of a given nucleotide sequence, wherein the complement and the nucleotide sequence consist of the same number of nucleotides and are 100% complementary.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes.

"Transgenic plant" also includes reference to plants which comprise more than one heterologous polynucleotide within their genome. Each heterologous polynucleotide may confer a different trait to the transgenic plant.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single or double-stranded, optionally containing synthetic, non-natural or altered nucleotide bases. Nucleotides (usually found in their 5' monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

Promoters that cause a gene to be expressed in most cell types at most times are commonly referred to as "constitutive promoters."

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

The term "locus" generally refers to a genetically defined region of a chromosome carrying a gene or, possibly, two or more genes so closely linked that genetically they behave as a single locus responsible for a phenotype. When used herein with respect to ZmCrw1, the "ZmCrw1 locus" shall refer to the defined region of the chromosome carrying the ZmCrw1 gene including its associated regulatory sequences.

A "gene" shall refer to a specific genetic coding region within a locus, including its associated regulatory sequences. One of ordinary skill in the art would understand that the associated regulatory sequences will be within a distance of about 4 kb from the ZmCrw1 coding sequence, with the promoter located upstream.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "favorable allele" is the allele at a particular locus that confers, or contributes to, a desirable phenotype, or alternatively, is an allele that allows the identification of plants that do not have the desirable phenotype so that they can be removed from a breeding program or planting. A favorable allele of a marker is a marker allele that segregates with the favorable phenotype, or alternatively, segregates with the unfavorable plant phenotype, therefore providing the benefit of identifying plants.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells, that can be cultured into a whole plant.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal W method of alignment.

The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB.

After alignment of the sequences, using the Clustal W program, it is possible to obtain "percent identity" and "divergence" values by viewing the "sequence distances" table on the same program; unless stated otherwise, percent identities and divergences provided and claimed herein were calculated in this manner. Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Turning now to the embodiments:

Embodiments include isolated polynucleotides, cDNAs and polypeptides, recombinant DNA constructs useful for increasing a plant's resistance to an insect pest, compositions (such as plants or seeds) comprising these recombinant DNA constructs, and methods utilizing these recombinant DNA constructs.

CRW1 crw1 (corn rootworm susceptible) is a maize mutant whose leaves are devoured by the Western corn rootworm (WCR) beetle (Dhillon B, Moose S P; and Johal G S. (2007). crw1—A novel maize mutant exceptionally susceptible to Western Corn Rootworm. *Maize Genetics Conference*. March 22-25, St. Charles, Ill. Abstract and Presentation available online). Thus, it appears that a mechanism that normally renders maize leaves unpalatable to the WCR beetle is compromised in the mutant.

crw1 is inherited in a recessive fashion and is controlled by a single gene. It has also been referred to as ecw1 (epidermal cell wall), as an independent mutant of this gene was identified in a mutant screen for plants that did not undergo a phase change from juvenile to adult phase (Dhillon B, Moose S P; and Johal G S. (2007). crw1—A novel maize mutant exceptionally susceptible to Western Corn Rootworm. *Maize Genetics Conference*. March 22-25, St. Charles, Ill. Abstract and Presentation available online). The polypeptide encoded by wild-type Crw1 (i.e. CRW1; SEQ ID NO:3) is a NAC transcription factor that is induced in response to Western corn rootworm beetle feeding and is developmentally regulated. Its expression is highest in the elogating internode. There also appears to be an upregulation of jasmonic acid biosynthesis and signaling in the Crw1 mutants that results in reduced expression of a few green leaf volatile genes in response to western corn rootworm beetle feeding.

Isolated Polynucleotide, cDNAs and Polypeptides

The present disclosure includes the following isolated polynucleotides, cDNAs, and polypeptides:

An isolated polynucleotide or cDNA comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:3, 10, 11, 12, 13, 14, 15, 16, 17, 18, 19, 20, 21, 22, 23, 24, 25, 26, or 27, and combinations thereof; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. The polypeptide is preferably a CRW1 polypeptide.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO: 3, 10, 11, 12, 13, 14, 15, 16, 17, 18, 19, 20, 21, 22, 23, 24, 25, 26, or 27, and combinations thereof. In an aspect, the polypeptide is a CRW1 polypeptide.

An isolated polynucleotide or cDNA comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:2; or (ii) a full complement of the nucleic acid sequence of (i). Any of the foregoing isolated polynucleotides or cDNAs may be utilized in any recombinant DNA constructs of the present disclosure.

An isolated polynucleotide or cDNA comprising a nucleotide sequence, wherein the nucleotide sequence is hybridizable under stringent conditions with a DNA molecule comprising the full complement of SEQ ID NO:2.

An isolated polynucleotide or cDNA comprising a nucleotide sequence, wherein the nucleotide sequence is derived from SEQ ID NO:2 by alteration of one or more nucleotides by at least one method selected from the group consisting of: deletion, substitution, addition and insertion.

An isolated polynucleotide or cDNA comprising a nucleotide sequence, wherein the nucleotide sequence corresponds to an allele of SEQ ID NO:2.

An isolated polynucleotide or cDNA comprising: (i) a nucleic acid sequence encoding a polypeptide having an amino acid sequence of at least 90% sequence identity, based on the Clustal W method of alignment, when compared to SEQ ID NO:3, 21, 23, or 27; or (ii) a full complement of the nucleic acid sequence of (i).

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N terminal and C terminal portions of the polypeptide molecule would also not be expected to alter the activity of the polypeptide. Each of the proposed modifications is well within the routine skill in the art, as is determination of retention of biological activity of the encoded products.

A protein of the current disclosure may also be a protein which comprises an amino acid sequence comprising deletion, substitution, insertion and/or addition of one or more amino acids in an amino acid sequence presented in SEQ ID NO: 3, 10, 11, 12, 13, 14, 15, 16, 17, 18, 19, 20, 21, 22, 23, 24, 25, 26, or 27. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Proteins derived by amino acid deletion, substitution, insertion and/or addition can be prepared when DNAs encoding their wild-type proteins are subjected to, for example, well-known site-directed mutagenesis (see, e.g., *Nucleic Acid Research*, Vol. 10, No. 20, p. 6487-6500, 1982, which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-directed mutagenesis mentioned above, as well as other techniques such as those for treating a gene with a mutagen, and those in which a gene is selectively cleaved to remove, substitute, insert or add a selected nucleotide or nucleotides, and then ligated.

A protein of the present disclosure may also be a protein which is encoded by a nucleic acid comprising a nucleotide sequence comprising deletion, substitution, insertion and/or addition of one or more nucleotides in the nucleotide sequence of SEQ ID NO:2. Nucleotide deletion, substitution, insertion and/or addition may be accomplished by site-directed mutagenesis or other techniques as mentioned above.

A protein of the present disclosure may also be a protein which is encoded by a nucleic acid comprising a nucleotide sequence hybridizable under stringent conditions with the complementary strand of the nucleotide sequence of SEQ ID NO:2.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., *Molecular Cloning: A Laboratory Manual*, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

Recombinant DNA Constructs

In an aspect, the present disclosure includes recombinant DNA constructs.

In an embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 3, 10, 11, 12, 13, 14, 15, 16, 17, 18, 19, 20, 21, 22, 23, 24, 25, 26, or 27, and combinations thereof; or (ii) a full complement of the nucleic acid sequence of (i).

In an embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:2, and combinations thereof; or (ii) a full complement of the nucleic acid sequence of (i).

In an embodiment, a recombinant DNA construct comprises a polynucleotide operably linked to at least one regulatory sequence (e.g., a promoter functional in a plant), wherein said polynucleotide encodes a CRW1 polypeptide. The CRW1 polypeptide may be from *Arabidopsis thaliana, Zea mays, Glycine max, Glycine tabacina, Glycine soja, Glycine tomentella, Oryza sativa, Brachypodium distachyon, Vitis vinifera, Gossypium mexicanum, Pyrus malus, Hordeum vulgare, Brassica napus, Sorghum bicolor, Saccharum officinarum*, or *Triticum aestivum*.

A recombinant DNA construct comprising an isolated polynucleotide or cDNA comprising (i) a nucleic acid sequence encoding a polypeptide having an amino acid sequence of at least 90% sequence identity, based on the Clustal W method of alignment, when compared to SEQ ID NO:3, 21, 23, or 27; or (ii) a full complement of the nucleic acid sequence of (i), operably linked to at least one regulatory element. In an aspect at least one regulatory element is a promoter. In an aspect, a promoter may be a root-specific promoter or the maize ubiquitin promoter.

Regulatory Sequences

A recombinant DNA construct of the present disclosure may comprise at least one regulatory sequence.

A regulatory sequence may be a promoter.

A number of promoters can be used in recombinant DNA constructs of the present disclosure. The promoters can be selected based on the desired outcome, and may include constitutive, tissue-specific, inducible, or other promoters for expression in the host organism.

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), the constitutive synthetic core promoter SCP1 (International Publication No. 03/033651) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Tissue-specific promoters useful in the current disclosure may include root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790; GI No. 1063664.

Promoters may be derived in their entirety from a native gene, or be composed of different elements derived from different promoters found in nature, or even comprise synthetic DNA segments.

Recombinant DNA constructs of the present disclosure may also include other regulatory sequences, including but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395-4405 (1988); Callis et al., *Genes Dev.* 1:1183-1200 (1987).

Any plant can be selected for the identification of regulatory sequences and genes encoding CRW1 polypeptides to be used in recombinant DNA constructs and other compositions (e.g. transgenic plants, seeds and cells) and methods of the present disclosure. Examples of suitable plants for the isolation of genes and regulatory sequences and for compositions and methods of the present disclosure would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, *sorghum*, Southern pine, soybean, spinach, squash, strawberry, sugarbeet, sugarcane, sunflower, sweet potato, sweetgum, switchgrass, tangerine, tea, tobacco, tomato, triticale, turf, turnip, a vine, watermelon, wheat, yams, and zucchini.

Compositions

A composition of the present disclosure includes a transgenic microorganism, cell, plant, and seed comprising a recombinant DNA construct disclosed herein. The cell may be eukaryotic, e.g., a yeast, insect or plant cell, or prokaryotic, e.g., a bacterial cell.

A composition of the present disclosure is a plant comprising in its genome one or more of the recombinant DNA constructs of the present disclosure. Compositions also include any progeny of the plant, and any seed obtained from the plant or its progeny, wherein the progeny or seed comprises within its genome a recombinant DNA construct disclosed herein. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit increased resistance to herbivory by an insect pest, or used in a breeding program to produce hybrid seed, which can be grown to produce plants that would exhibit increased resistance to herbivory by an insect pest. The seeds may be maize seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley, millet, sugar cane or switchgrass.

The recombinant DNA construct may be stably integrated into the genome of the plant.

Particular embodiments include but are not limited to the following:

1. A plant (for example, a maize plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 3, 10, 11, 12, 13, 14, 15, 16, 17, 18, 19, 20, 21, 22, 23, 24, 25, 26, or 27, and wherein said plant exhibits increased resistance to herbivory by an insect pest when compared to a control plant not comprising said recombinant DNA construct.

2. A plant (for example, a maize plant) comprising in its genome a recombinant DNA construct comprising a polynucleotide operably linked to at least one regulatory sequence, wherein said polynucleotide encodes a CRW1 polypeptide, and wherein said plant exhibits increased resistance to herbivory by an insect pest when compared to a control plant not comprising said recombinant DNA construct.

3. A plant (for example, a maize plant) comprising in its genome a recombinant DNA construct comprising a polynucleotide operably linked to at least one regulatory element, wherein said polynucleotide comprises a nucleotide sequence, wherein the nucleotide sequence is: (a) hybridizable under stringent conditions with a DNA molecule comprising the full complement of SEQ ID NO:2; or (b) derived from SEQ ID NO:2 by alteration of one or more nucleotides by at least one method selected from the group consisting of: deletion, substitution, addition and insertion; and wherein said plant exhibits increased resistance to herbivory by an insect pest, when compared to a control plant not comprising said recombinant DNA construct.

4. Any progeny of the plants in the embodiments described herein, any seeds of the plants in the embodiments described herein, any seeds of progeny of the plants in embodiments described herein, and cells from any of the above plants in embodiments described herein and progeny thereof.

In any of the embodiments described herein, the CRW1 polypeptide may be from *Arabidopsis thaliana, Zea mays, Glycine max, Glycine tabacina, Glycine soja, Glycine tomentella, Oryza sativa, Brachypodium distachyon, Vitis vinifera, Gossypium mexicanum, Pyrus malus, Hordeum vulgare, Brassica napus, Sorghum bicolor, Saccharum officinarum,* or *Triticum aestivum.*

In any of the embodiments described herein, the recombinant DNA construct may comprise at least a promoter functional in a plant as a regulatory sequence.

In any of the embodiments described herein, the plant (for example, the maize plant) may exhibit less yield loss relative to the control plants, for example, at least 25%, at least 20%, at least 15%, at least 10% or at least 5% less yield loss, under similar environmental conditions and pest pressure.

"Insect pest pressure" refers to the level of infestation of an insect.

"Insect" and "insect pest" are used interchangeably herein.

The insect pest may be in the adult or larval stage. The adult stage is of particular insect.

The insect may be in the order Coleoptera, and the Coleopteran insect may be of the genus *Diabrotica*. *Diabrotica* is a widespread genus of beetles that includes several destructive agricultural pest species including, for example, corn rootworms.

The insect may be any species of corn rootworm. Corn rootworms are one of the most economically destructive insects of maize in the United States. The Western corn rootworm, *D. virgifera virgifera*, and the Northern corn rootworm, *D. barberi*, are the most devastating rootworm species in Iowa, a major corn-growing area. A third species, the Southern corn rootworm, *D. undecimpunctata howardi*, causes much economic damage in other regions.

The insect may be in the order Lepidoptera, and the Lepidopteran insect may be of the genus *Ostrinia*. *Ostrinia* is a genus of moths. One such member of the genus is the European Corn Borer, a serious pest of maize. An insect of the disclosure may be but is not limited to the European Corn Borer.

"Herbivory" as used herein is the consumption of living plant tissue by insects. The plant tissue may be tissue from any plant part including but not limited to leaves, stem, roots, reproductive parts, etc. Chronic attack by herbivores can have dramatic cumulative effects on the size, longevity, or reproductive output of individual plants.

"Susceptibility" refers to the inability of a plant variety to restrict the growth and development of a specified pest.

"Resistance" refers to the ability of a plant variety to restrict the growth and development of a specified pest and/or the damage they cause when compared to susceptible plant varieties under similar environmental conditions and pest pressure.

Typically, when a transgenic plant comprising a recombinant DNA construct in its genome exhibits increased resistance to herbivory by an insect pest relative to a reference or control plant, the reference or control plant does not comprise in its genome the recombinant DNA construct.

One of ordinary skill in the art is familiar with protocols for evaluating insect response (i.e. attractiveness or repulsiveness) to plant tissue and for evaluating a plant's level of resistance to an insect pest.

As presented herein, one can perform a feeding choice assay. In this assay, a PVC box containing a detachable lid is used to contain the insects and plant hosts, and equal weights of freshly harvested mature leaves of the plant hosts are affixed to moist filter paper in a randomized manner. Insects are starved overnight and placed in the box with the tissue. Leaf feeding can be scored on a scale from 0 to 5, with 0 indicating no damage and 5 indicating complete decimation.

One can also evaluate a plant's resistance to an insect pest by the plant's ability to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under sufficient pest pressure.

One of ordinary skill in the art would readily recognize a suitable control or reference plant to be utilized when assessing or measuring a phenotype of a transgenic plant in any embodiment of the present disclosure in which a control plant is utilized (e.g., compositions or methods as described herein). For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct (i.e., the progeny not comprising the recombinant DNA construct is the control or reference plant).

2. Introgression of a recombinant DNA construct into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring a phenotype of a transgenic plant would not include a plant that had been previously selected, via mutagenesis or transformation, for the desired phenotype.

Methods

Methods include but are not limited to methods for increasing resistance to herbivory by an insect pest in a plant, methods for evaluating resistance to an insect pest in a plant, methods of identifying variants and/or naturally occurring alleles of Crw1 that give plants increased resistance to herbivory by an insect pest, and methods for producing seed. The plant may be a monocotyledonous or dicotyledonous plant, for example, a maize or soybean plant. The plant may also be sunflower, *sorghum*, canola, wheat, alfalfa, cotton, rice, barley, millet, sugar cane or *sorghum*. The seed may be a maize or soybean seed, for example, a maize hybrid seed or maize inbred seed.

Methods include but are not limited to the following:

A method for transforming a cell (or microorganism) comprising transforming a cell (or microorganism) with any of the isolated polynucleotides or recombinant DNA constructs of the present disclosure. The cell (or microorganism) transformed by this method is also included. In particular embodiments, the cell is eukaryotic cell, e.g., a yeast, insect or plant cell, or prokaryotic, e.g., a bacterial cell. The microorganism may be *Agrobacterium*, e.g. *Agrobacterium tumefaciens* or *Agrobacterium rhizogenes*.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method, and transgenic seed obtained from this transgenic plant. The transgenic plant obtained by this method may be used in other methods of the present disclosure.

A plant cell of the present invention may comprise a recombinant construct comprising a polynucleotide comprising (i) a nucleic acid sequence encoding a polypeptide having an amino acid sequence of at least 90% sequence identity, based on the Clustal W method of alignment, when compared to SEQ ID NO:3, 21, 23, or 27; or (ii) a full complement of the nucleic acid sequence of (i) that is operably linked to at least one regulatory element. For example, a regulatory element may be a promoter. An exemplary promoter may be a root-specific promoter or the maize ubiquitin promoter. A plant of the present invention may comprise such a plant cell comprising a recombinant construct comprising a polynucleotide comprising (i) a nucleic acid sequence encoding a polypeptide having an amino acid sequence of at least 90% sequence identity, based on the Clustal W method of alignment, when compared to SEQ ID NO:3, 21, 23, or 27; or (ii) a full complement of the nucleic acid sequence of (i) that is operably linked to at least one regulatory element. For example, a regulatory element may be a promoter. An exemplary promoter may be a root-specific promoter or the maize ubiquitin promoter Such a plant may display increased resistance to herbivory by an insect pest. The insect pest may be Coleopteran. The insect pest may be of the genus *Diabrotica*. The insect pest may be Lepidopteran. The insect pest may be European corn borer. The plant may be a monocot. The plant may be maize.

A plant of the present invention may comprise in its genome a recombinant DNA construct comprising a polynucleotide operably linked to at least one regulatory element, wherein said polynucleotide encodes a polypeptide having an amino acid sequence of at least 50% sequence identity, based on the Clustal W method of alignment, when compared to SEQ ID NO:3, 10, 11, 12, 13, 14, 15, 16, 17, 18, 19, 20, 21, 22, 23, 24, 25, 26, and 27, and wherein said plant exhibits increased resistance to herbivory by an insect pest when compared to a control plant not comprising said recombinant DNA construct. For example, a regulatory element may be a promoter. An exemplary promoter may be a root-specific promoter or the maize ubiquitin promoter. The insect pest may be Coleopteran. The insect pest may be of the genus *Diabrotica*. The insect pest may be Lepidopteran. The insect pest may be European corn borer. The plant may be a monocot. The plant may be maize.

A method for isolating a polypeptide of the disclosure from a cell or culture medium of the cell, wherein the cell comprises a recombinant DNA construct comprising a polynucleotide of the disclosure operably linked to at least one regulatory sequence, and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure; and (b) growing the transformed host cell under conditions that are suitable for expression of the recombinant DNA construct wherein expression of the recombinant DNA construct results in production of altered levels of the polypeptide of the disclosure in the transformed host cell.

A method of increasing resistance to herbivory by an insect pest in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 3, 10, 11, 12, 13, 14, 15, 16, 17, 18, 19, 20, 21, 22, 23, 24, 25, 26, or 27; and (b) regenerating a transgenic plant from the regenerable plant cell after step (a), wherein the transgenic plant comprises in its genome the recombinant DNA construct and exhibits increased resistance to herbivory by an insect pest when compared to a control plant not comprising the recombinant DNA construct. The method may further comprise (c) obtaining a progeny plant derived from the transgenic plant, wherein said progeny plant comprises in its genome the recombinant DNA construct and exhibits increased resistance to herbivory by an insect pest when compared to a control plant not comprising the recombinant DNA construct.

A method of increasing resistance to herbivory by an insect pest in a plant, the method comprising: (a) introducing into a regenerable plant cell a recombinant DNA construct comprising a polynucleotide operably linked to at least one regulatory element, wherein said polynucleotide comprises a nucleotide sequence, wherein the nucleotide sequence is: (a) hybridizable under stringent conditions with a DNA molecule comprising the full complement of SEQ ID NO:2; or (b) derived from SEQ ID NO:2 by alteration of one or more nucleotides by at least one method selected from the group consisting of: deletion, substitution, addition and insertion; and (b) regenerating a transgenic plant from the regenerable plant cell after step (a), wherein the transgenic plant comprises in its genome the recombinant DNA construct and exhibits increased resistance to herbivory by an insect pest in a plant when compared to a control plant not comprising the recombinant DNA construct. The method may further comprise (c) obtaining a progeny plant derived from the transgenic plant, wherein said progeny plant comprises in its genome the recombinant DNA construct and exhibits increased resistance to herbivory by an insect pest in a plant, when compared to a control plant not comprising the recombinant DNA construct.

A method of evaluating resistance to an insect pest in a plant, comprising (a) obtaining a transgenic plant, wherein the transgenic plant comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 3, 10, 11, 12, 13, 14, 15, 16, 17, 18, 19, 20, 21, 22, 23, 24, 25, 26, or 27; (b) obtaining a progeny plant derived from said transgenic plant, wherein the progeny plant comprises in its genome the recombinant DNA construct; and (c) evaluating the progeny plant for resistance to an insect pest in a plant compared to a control plant not comprising the recombinant DNA construct.

In another embodiment, a method of evaluating resistance to an insect pest in a plant, comprising: (a) obtaining a transgenic plant, wherein the transgenic plant comprises in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 3, 10, 11, 12, 13, 14, 15, 16, 17, 18, 19, 20, 21, 22, 23, 24, 25, 26, or 27; (b) growing the transgenic plant of part (a) under conditions wherein the polynucleotide is expressed; and (c) evaluating the transgenic plant of part (b) for resistance to an insect pest in a plant compared to a control plant not comprising the recombinant DNA construct.

A method of evaluating resistance to an insect pest in a plant, the method comprising: (a) obtaining a transgenic plant, wherein the transgenic plant comprises in its genome a recombinant DNA construct comprising a polynucleotide operably linked to at least one regulatory element, wherein said polynucleotide comprises a nucleotide sequence, wherein the nucleotide sequence is: (a) hybridizable under stringent conditions with a DNA molecule comprising the full complement of SEQ ID NO:2; or (b) derived from SEQ ID NO:2 by alteration of one or more nucleotides by at least one method selected from the group consisting of: deletion, substitution, addition and insertion; (b) obtaining a progeny plant derived from said transgenic plant, wherein the progeny plant comprises in its genome the recombinant DNA construct; and (c) evaluating the progeny plant for increased resistance to herbivory by an insect pest in a plant, when compared to a control plant not comprising the recombinant DNA construct.

In any of the preceding methods or any other embodiments of methods of the present disclosure, in said introducing step said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, said regenerating step may comprise the following: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

The introduction of recombinant DNA constructs of the present disclosure into plants may be carried out by any suitable technique, including but not limited to direct DNA uptake, chemical treatment, electroporation, microinjection, cell fusion, infection, vector-mediated DNA transfer, bombardment, or Agrobacterium-mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

In an embodiment, a method of identifying a variant of Crw1 that gives plants increased resistance to herbivory by an insect pest is provided. Such method comprises: (a) combining through gene shuffling one or more nucleotide sequences encoding one or more fragments of SEQ ID NO: 3, 10, 11, 12, 13, 14, 15, 16, 17, 18, 19, 20, 21, 22, 23, 24, 25, 26, or 27 or a protein that is at least 70% identical to SEQ ID NO: 3, 10, 11, 12, 13, 14, 15, 16, 17, 18, 19, 20, 21, 22, 23, 24, 25, 26, or 27, or a fragment thereof; (b) transforming the shuffled sequences from step (a) into a population of regenerable plant cells; (c) regenerating a population of transformed plants from the population of transformed regenerable plant cells of step (b); (d) screening the population of transformed plants from step (c) for increased resistance to herbivory by said insect pest; and (e) identifying the variant from the transformed plant exhibiting the increased resistance. The method can further comprise: (f) introducing into a regenerable plant cell a recombinant construct comprising a variant of Crw1 that gives plants increased resistance to herbivory by an insect pest; (g) regenerating a transgenic plant from the regenerable plant cell after step (f), wherein the transgenic plant comprises in its genome the recombinant DNA construct; and (h) selecting a transgenic plant of (g), wherein the transgenic plant comprises the recombinant DNA construct and exhibits increased resistance to herbivory by said insect pest, when compared to a control plant not comprising the recombinant DNA construct. For example, a method of identifying a variant of Crw1 that gives plants increased resistance to herbivory by an insect pest, may comprise the steps of a) combining through gene shuffling one or more nucleotide sequences encoding one or more fragments of SEQ ID NO:3 or a protein that is at least 70% identical to SEQ ID NO:3, or a fragment thereof, to generate variants of Crw1; b) identifying a variant that exhibits the increased resistance, transforming the shuffled sequences from step (a) into a population of regenerable plant cells; c) regenerating a population of transformed plants from the population of transformed regenerable plant cells of step (b); d) screening the population of transformed plants from step (c) for increased resistance to said insect pest; and, e) identifying the variant that exhibits the increased resistance. The method may comprise an insect pest that is Coleopteran. The method may comprise an insect pest that is of the genus *Diabrotica*. The method may comprise an insect pest that is Lepidopteran. The method may comprise an insect pest that is European corn borer. The method may comprise screening using a feeding choice assay.

A method of the present invention may comprise a method of identifying an allelic variant of Crw1 in a maize plant that is associated with increased resistance to herbivory by an insect pest, the method comprising the steps of a) crossing two maize plants with differing levels of resistance to said insect pest; b) evaluating allelic variations in the progeny plants with respect to the polynucleotide sequence encoding a protein comprising SEQ ID NO:3 or in the genomic region that regulates the expression of the polynucleotide encoding the protein; c) phenotyping the progeny plants for resistance to said insect pest; d) associating allelic variations with said resistance; and e) identifying the alleles that are associated with increased resistance to said insect pest. The method may comprise an insect pest that is Lepidopteran. The method may comprise an insect pest that is European corn borer. The method may comprise screening using a feeding choice assay. In the method, the level of resistance of a maize plant in the population may be obtained from historical data or by performing a feeding choice assay.

The terms "gene shuffling" and "directed evolution" can be used interchangeably herein. The method of "gene shuffling" consists of iterations of DNA shuffling followed by appropriate screening and/or selection to generate variants of Crw1 nucleic acids or portions thereof having a modified biological activity (Castle et al., (2004) *Science* 304(5674): 1151-4; U.S. Pat. Nos. 5,811,238 and 6,395,547).

Methods of identifying allelic variants of Crw1 in maize that are associated with increased resistance to herbivory by an insect pest by way of traditional linkage mapping are also provided. In some embodiments, the allelic variants are identified by (a) crossing two maize plants with differing levels of resistance to said insect pest; (b) evaluating allelic variations in the progeny plants with respect to the polynucleotide sequence encoding a protein comprising SEQ ID NO:3 or in the genomic region that regulates the expression of the polynucleotide encoding the protein; (c) phenotyping the progeny plants for resistance to said insect pest; (d) associating allelic variations with said resistance; and (e) identifying the alleles that are associated with increased resistance to said insect pest. The phenotyping step (c) could be performed using any method of assessing resistance to an insect pest that is known in the art or could be performed using a feeding choice assay presented herein.

In other embodiments the allelic variants are identified through whole genome association analysis by: (a) obtaining a population of maize plants, wherein said maize plants exhibit differing levels of resistance to said insect pest; (b) evaluating allelic variations with respect to the polynucleotide sequence encoding a protein comprising SEQ ID NO:3, or in the genomic region that regulates the expression of the polynucleotide encoding the protein; (c) associating allelic variations with said resistance; and (d) identifying an allelic variant that is associated with increased resistance to the insect pest. Resistance could be assessed using any method known to one or ordinary skill in the art or the feeding choice assay. Alternatively, historical phenotypic data regarding the resistance could also be used.

Also provided are methods of identifying a maize plant that exhibits increased resistance to herbivory by an insect pest, the method comprising: (a) detecting the presence of at least one allelic variant of Crw1 that is associated with increased resistance to said insect pest, in the genome of the maize plant (wherein the allelic variant can be identified using the methods described above); and (b) identifying a maize plant that comprises said at least one allelic variant. The method can further comprise: (c) crossing said maize plant to a second maize plant; and (d) identifying and selecting progeny plants arising from said cross that have said allelic variant.

In any of the methods presented above, the insect pest may be in the order Coleoptera, and the Coleopteran insect may be of the genus *Diabrotica*. The insect pest may further be any species of corn rootworm.

Alternatively, the insect pest may be in the order Lepidoptera, and the Lepidopteran insect may be of the genus *Ostrinia*. The insect pest may further be the European Corn Borer.

In any of the methods presented above, the evaluation of resistance to an insect pest can comprise any protocol known to one of ordinary skill in the art. The feeding choice assay presented herein could also be used.

In any of the methods presented above, the plant is a monocot plant and can be maize.

EXAMPLES

The present disclosure is further illustrated in the following Examples, in which parts and percentages are by weight and degrees are Celsius, unless otherwise stated. It should be understood that these Examples, while indicating embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

Example 1

Foliar Feeding Choice Assay

A feeding choice assay was performed to assess the level of resistance to corn rootworm beetles in Crw1 mutant and wild-type plants. A PVC box containing a detachable lid was used, and equal weights of freshly harvested mature leaves from both mutant and wild-type plants are affixed to moist filter paper in a randomized manner. Western corn rootworm beetles and southern corn rootworm beetles, which had been starved overnight, were placed into the box. Previous observations showed that the establishment of feeding preference is usually preceded by random scouting within the first 45 minutes, and that preferential feeding usually continues until the leaves of choice are completely devoured. Leaf feeding was scored on a scale from 0 to 5, with 0 indicating no damage and 5 indicating complete decimation.

Example 2

Cloning and Validation of Maize Crw1 Gene

Figure 1:
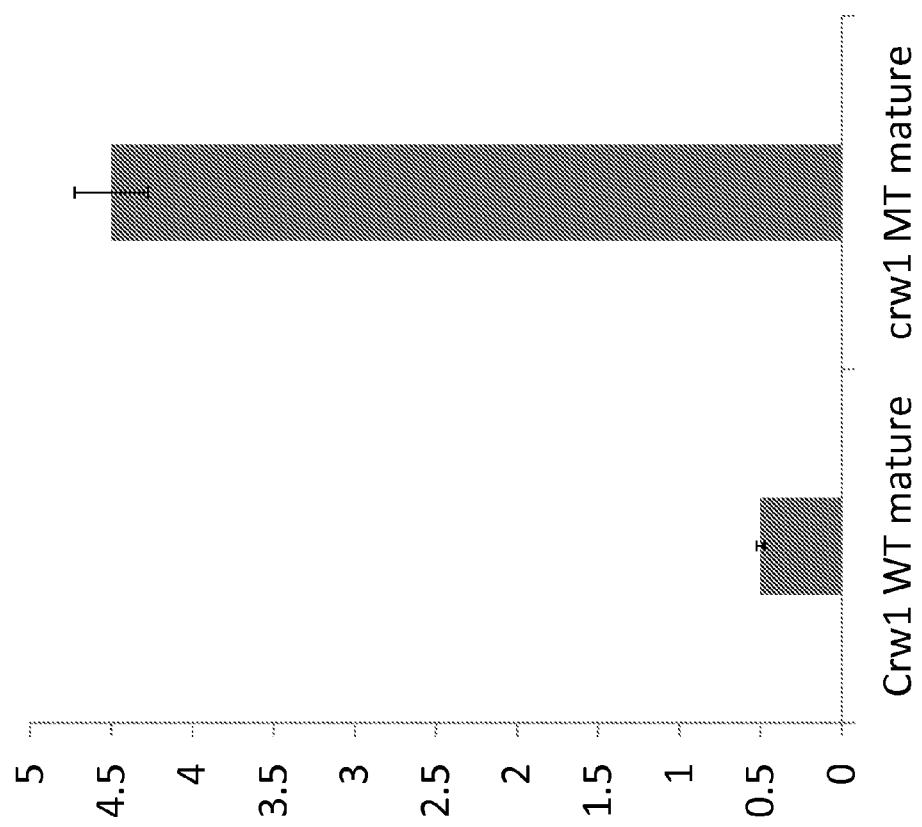
FIG. 1 shows results obtained from a foliar feeding choice assay in which Western corn rootworm (WCR) beetles were placed in a box with leaves from the maize crw1-Ac mutant and leaves from their wild-type SIBs. The results represent the average mean of 9 biological samples.
Figure 2:
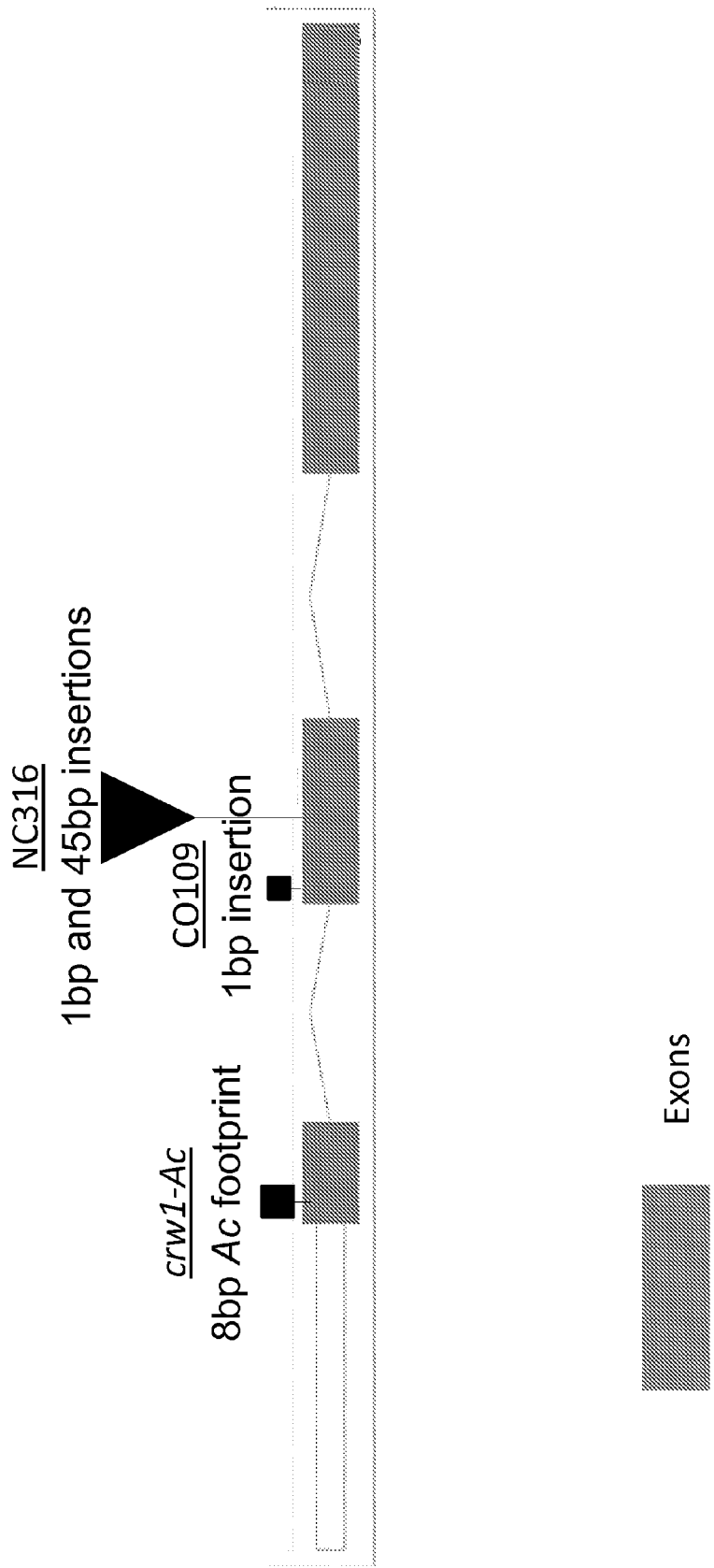
FIG. 2 shows a schematic representation of the maize Crw1 gene; the position of the mutation in the crw1-Ac mutant line; and the positions of the insertions in the public diversity lines CO109 and NC316.

A Crw1 maize mutant, which is highly susceptible to the adult beetle of Western corn rootworm (WCR), was identified in Ac-active material (and is also referred to herein as the crw1-Ac mutant). FIG. 1 shows that WCR beetles have an overwhelming preference for crw1-Ac mutant leaves over wild-type sib (WT-sib) leaves as assessed using the feeding choice assay. The gene was cloned by co-segregation analysis with Ac, and it was determined that the Crw1 gene is on chromosome 6 and that it encodes a polypeptide with high homology to the plant-specific NAC family transcription factors. A stably mutant but revertant allele of Crw1 containing an 8-bp direct duplication at the site of insertion ('footprint' of Ac excision) was identified from the original Ac allele. This 8-bp insertion causes premature termination of CRW1. FIG. 2 shows a schematic representation of the Crw1 gene and the position of the mutation in the crw1-Ac mutant. FIGS. 6A-6C show the alignment between wild-type Crw1 and the crw1-Ac allele. SEQ ID NOs:3 and 4 refer to the crw1-Ac nucleotide coding sequence and CRW1-Ac amino acid sequence, respectively.

To identify additional mutant alleles of Crw1, a public collection of maize diversity lines was first screened for susceptibility to the WCR beetle in the field under natural conditions of infestation before validation by the foliar feeding choice assay described in Example 1. Two public diversity lines, CO109 and NC316, were found to segregate for susceptibility to the WCR beetle. By crossing each of the lines to the crw1-Ac line, it was shown that CO109 and NC316 contained naturally occurring mutant alleles at the Crw1 gene that conferred increased susceptibility to WCR beetles. Sequencing of the Crw1 cDNA in each line showed that CO109 contains a 1 bp insertion (at nucleotide 368) in exon 2 and NC316 contains a 1 bp insertion (at nucleotide 366) and a 45 bp insertion at separate positions in exon 2. Premature termination codons result in both instances. FIG. 2 shows the positions of the mutations in the CO109 and NC316 lines. FIGS. 7A-7C show the alignment between wild-type Crw1 and Crw1 from CO109. SEQ ID NOs:6 and 7 refer to the crw1-00109 nucleotide coding sequence and CRW1-00109 amino acid sequence, respectively. FIGS. 8A-8C show the alignment between wild-type Crw1 and Crw1 from NC316. SEQ ID NOs:8 and 9 refer to the crw1-NC316 nucleotide coding sequence and CRW1-NC316 amino acid sequence, respectively.

Example 3

Transcriptional and Biochemical Characteristics of the Maize Crw1 Gene

The transcriptional profile of the maize Crw1 gene has been difficult to establish fully thus far. Though not wishing to be bound by any particular theory, one possible reason is that the maize Crw1 transcript may lack a polyA tail. This prediction is based on the fact that the maize Crw1 cDNA has not been found in any public EST database. In addition, no reads of the maize Crw1 gene were detected in an RNA seq experiment (transcriptomics) which was conducted on cDNAs generated from RNA samples of adult leaves isolated at different time intervals following beetle damage. Nevertheless, the transcriptomics experiment and subsequent RT-PCR verification of significant hits revealed three important features of the maize Crw1 mutant:

First, there was a significant change in the expression of the lipoxygenase pathway genes that control Jasmonic Acid (JA) and green leaf volatile (GLV, such as diterpenes) production in maize. Both of these compounds play significant, albeit opposing, roles in plants' interaction with insect pests. For instance, JAs are known to mediate host resistance, whereas GLVs aid attraction of pests as well as their predators. While the expression of the JA pathway genes was upregulated in maize Crw1 mutants compared to their WT counterparts (Table 1), the expression of the GLV genes was diminished, suggesting that the overexpression of one or more of the GLV genes may also provide resistance to insects. The results obtained from the expression analysis were consistent with the higher inducible levels of JA in mutant Crw1 plants compared to their WT counterparts (FIG. 3).

Table 1 is a list of the lipoxygenase pathway genes regulated differentially in the Crw1 mutant compared to WT siblings in response to insect feeding. The positive and negative values indicate the fold change of a particular transcript in the mutant vs. WT. There appears to be an up-regulation of the JA biosynthesis and signalling genes and a concomitant reduction of GLV genes in Crw1 mutants in response to WCR feeding.

| Gene name(ID) | Fold Change(log2) | Indicated Function |
|---|---|---|
| LOX2 (EU971362) | +1.8 | JA biosynthesis |
| AOS (NM001111774) | +1.8 | JA biosynthesis |
| OPR12(EU970844) | +2.58 | JA biosynthesis |
| ZIM motif family protein (LOC100284979) | −2.58 | JA signaling |
| Skp1-like protein 1a (NM_001136917) | +2.58 | JA signaling |
| ACO31(NM001111764) | +3.16 | JA/ET signalling |
| ERF1 like (NM001111800) | +2 | ET/JA signaling |
| LOX10 (NM001112510) | −2 | GLV biosynthesis |
| Fps (EU961933) | −2 | GLV biosynthesis |
| Mevalonate kinase (EU974298) | −4.16 | Terpenoid biosynthesis |
| HMG-CoA synthase (EU961019) | −2.58 | Terpenoid biosynthesis |
| TPS7 (EU954571) | −2.2 | Terpenoid biosynthesis |
| TPS11(EU716166) | −1.8 | Terpenoid biosynthesis |
| B6TY42_Glycosyltransferase | −2.8 | Resistance to WCR feeding |

Second, the expression of phenylpropanoid and lignin biosynthetic genes was downregulated in the maize Crw1 mutant (Table 2). Compatible with these results are the findings that the Crw1 mutants accumulated lower levels of p-coumaric and ferulic acids (FIG. 4) and exhibited reduced lignification of adult tissues (FIG. 5). Given that these phenolics carry out cell wall cross-linking, the results presented herein agreed with both the compromised tensile strength of Crw1 mutant leaves and their altered staining with toluidine blue O (TBO), which reacts with free hydroxyl groups in the cell wall.

Table 2 is a list of differentially regulated transcripts involved in lignin biosynthesis. The positive and negative values indicate the fold change of a particular transcript in the Crw1 mutant in comparison to the WT. There appears to be an up-regulation of negative regulators of lignin biosynthesis and down-regulation of few key genes of the lignin biosynthetic pathway in Crw1 mutants in response to WCR beetle feeding.

| Gene name(ID) | Fold Change(log2) | Indicated Function |
|---|---|---|
| MYB39 (GRMZM2G127857) | +2 | −ve regulator of lignin biosynthesis |
| MYB42 (GRMZM2G419239) | +2.16 | −ve regulator of lignin biosynthesis |
| MYB1 (GRMZM2G005066) | −3.8 | +ve regulator of lignin biosynthesis |
| MYB59 (GRMZM2G093789) | −4.6 | +ve regulator of lignin biosynthesis |
| Hydroxycinnamoyl shikimate quinate transferase- like (NM001139418) | −4.45 | Key enzyme in the lignin biosynthesis |
| COMT (EU964048) | −1.8 | Key enzyme in lignin biosynthesis |

Third, the expression of many of the amino acid biosynthetic and modification genes was upregulated in the Crw1 mutants (Table 3), which, in turn, caused higher levels of relevant amino acids (Table 4). Prominent among these free amino acids were alanine, asparagine, glycine, and serine, all of which have shown to act as potent phagostimulants for WCR beetles.

Table 3 is a list of amino acid biosynthesis or modification genes differentially induced in the mutant vs. wild type siblings of Crw1 in response to WCR feeding. The positive and negative values indicate the fold change of a particular transcript in the Crw1 mutant in comparison to the WT. Alanine amino transferase is involved in the formation of alanine, while serine family amino acid biosynthesis like-protein and glycine hydroxymethyltransferase are involved in the formation of alanine and glycine.

| Gene name(ID) | Fold Change(log2) | Indicated Function |
|---|---|---|
| Aspartate aminotransferase (EU965394) | +2.3 | Aspartate metabolism |
| Alanine amino transferase-like protein (EL01N0413D07) | +1.8 | Alanine metabolism |
| Hypothetical protein (NM001149740) Serine family amino acid biosynthesis-like | +7.3 | Serine family amino acid biosynthesis |
| Glycine hydroxymethyl-transferase EU961022 | −2 | Glycine-Serine interconversion |
| Sad1 (NM_001137318) | +1.8 | Shikimic acid biosynthesis |

Table 4 shows growth stage specific leaf metabolite distribution in the Crw1 mutants. The differential metabolite levels are presented as fold change in the mutant in comparison to wild-type. The negative and positive values indicate lower and higher levels respectively, of a particular metabolite in the mutant in comparison to wild-type at a particular growth stage. A zero value in the table indicates no fold change was detected at that particular growth stage.

| | Growth Stage | | |
|---|---|---|---|
| | Juvenile | Transition | Mature |
| Metabolite Class | | Fold Change | |
| Amino acids | | | |
| Alanine | 0 | +3.1 | +2.5 |
| Asparagine | −3.5 | +2.7 | +9.7 |
| Aspartic Acid | −2.1 | +2.2 | +2.1 |
| Glycine | −1.8 | +2.1 | +2.9 |
| Serine | 0 | +2.5 | +4.8 |

-continued

| Metabolite Class | Growth Stage | | |
| --- | --- | --- | --- |
| | Juvenile | Transition Fold Change | Mature |
| Tyramine | −2.6 | 0 | +1.9 |
| Threonine | 0 | +1.9 | +1.9 |
| Glutamic Acid | 0 | 0 | +2.1 |
| Sugars | | | |
| Arabinose | 0 | −1.2 | +1.3 |
| Glucose | −2.2 | +1.8 | +1.6 |
| Ribose | 0 | +1.5 | +1.5 |
| Raffinose | 0 | 0 | +1.2 |
| Inositol | −1.1 | −1.1 | +1.1 |
| Organic acids | | | |
| Aconitic Acid | 0 | 0 | +1.1 |
| Alpha- Ketoglutaric Acid | 0 | 0 | +1.7 |
| Cinnamic Acid | 0 | +2.2 | +2.1 |
| Iso-Citric Acid | 0 | 0 | +1.9 |
| Shikimic Acid | 0 | 0 | +2.5 |

Example 4

Identification of Homologs of the Maize CRW1 Polypeptide

The maize CRW1 polypeptide can be analyzed for similarity to all publicly available amino acid sequences contained in the "nr" database using the BLASTP algorithm provided by the National Center for Biotechnology Information (NCBI) as well as to the DUPONT™ proprietary internal databases.

A BLAST search using the sequence of the maize CRW1 polypeptide revealed similarity of the maize CRW1 polypeptide to NAC transcription factors from various organisms. Shown in Table 5 (non-patent literature) are the BLASTP results for the amino acid sequence of the maize CRW1. Also shown in Tables 5 and 6 are the percent sequence identity values for each pair of amino acid sequences using the Clustal W method of alignment with default parameters:

TABLE 5

BLASTP Results for Maize CRW1 Polypeptide (Non-patent)

| UniProt Identifier | % Seq Identity |
| --- | --- |
| G3M8D2 (SEQ ID NO: 10) | 76.2 |
| Q9SNM6 (SEQ ID NO: 11) | 55.4 |
| C5YM23 (SEQ ID NO: 12) | 85.8 |
| Q5NKS7 (SEQ ID NO: 13) | 52.0 |
| I1MKD6 (SEQ ID NO: 14) | 58.6 |
| I1KHQ4 (SEQ ID NO: 15) | 59.1 |
| Q84WP6 (SEQ ID NO: 16) | 56.2 |
| Q9LPI7 (SEQ ID NO: 17) | 52.3 |
| Q9M274 (SEQ ID NO: 18) | 52.7 |
| B4FPS5 (SEQ ID NO: 19) | 80.3 |
| Q5NKQ3 (SEQ ID NO: 20) | 52.3 |
| *BdCRW1 (SEQ ID NO: 21) | 63.5 |
| F6HU82 (SEQ ID NO: 22) | 56.1 |
| *GmCRW1 (SEQ ID NO: 23) | 58.6 |
| G4V2G0 (SEQ ID NO: 24) | 53.4 |
| D9ZJ90 (SEQ ID NO: 25) | 54.8 |
| F2DV83 (SEQ ID NO: 26) | 50.0 |
| Q84WP6 (SEQ ID NO: 27) | 56.2 |

*Identifiers noted with an asterisk are not UniProt Identifiers

FIGS. 9A-9L present an alignment of the amino acid sequences of the polypeptides set forth in SEQ ID NOs:3, 10, 11, 12, 13, 14, 15, 16, 17, 18, 19, 20, 21, 22, 23, 24, 25, 26, and 27. FIG. 10 presents the percent sequence identities and divergence values for each sequence pair presented in FIGS. 9A-9L.

Sequence alignments and percent identity calculations were performed using the Megalign® program of the LASERGENE® bioinformatics computing suite (DNASTAR® Inc., Madison, Wis.). Multiple alignment of the sequences was performed using the Clustal W method of alignment (Thompson et al. (1994) Nucleic Acids Research. 22:4673-80) with the default parameters (GAP PENALTY=10, GAP LENGTH PENALTY=0.20). Default parameters for pairwise alignments using the Clustal method were GAP PENALTY=10.00 and GAP LENGTH=0.10. The Protein Weight Matrix used was the Gonnet series.

Example 5

Overexpressing Crw1 in Plants

The maize Crw1 gene or any of its homologs can be inserted into a vector, which can further be transformed into plants (including but not limited to maize) using methods known to one of ordinary skill in the art. Phenotypic analysis can then be performed similarly to that in previously described Examples or using any known method of assessment to determine the plant's resistance to an insect pest such as but not limited to the Western corn rootworm.

Example 6

Overexpression of Crw1 in Maize Plants

A 2.05 kb Crw1 fragment was amplified from maize genomic DNA using sense (SEQ ID NO:28) and antisense (SEQ ID NO:29) primers and Phusion DNA polymerase. This DNA fragment, essentially comprising the Crw1 coding region flanked by BgIII (5') and HpaI (3') sites, was subcloned into pCR4-TOPO. The sequence was determined to insure accuracy, and the fragment was then excised and cloned into an entry clone (PHP31847). This entry clone consists of an enhanced maize ubiquitin promoter (plus 5' UTR and intron), the Crw1 coding region, and the PINII terminator. The entire cassette, surrounded by Gateway attL1 and attL2 recombination sites, was mobilized into the appropriate plant expression destination vector via an LR recombination reaction. The resultant Ubi-Crw1construct, PHP41109, was introduced via Agrobacterium-mediated transformation into maize callus. Plants were regenerated from the callus, and one event, 8908.102.1.17 was shown to have the full length transcript. RT-PCR using primer combinations phn11317(SEQ ID NO:30)/phn140720(SEQ ID NO:31) and phn140719(SEQ ID NO:32)/phn140720(SEQ ID NO:31) showed that T1 plants having event #17.4 contained full-length transcripts of Crw1 (FIG. 11). The T1 plants can be tested for susceptibility to an insect pest such as the Western corn rootworm using any known method in the art or the feeding choice assay described in Example 1.

A second construct was generated for root preferred expression of Crw1. For this purpose, a 1.3445 kb fragment from a maize metallothionein gene (Rm2; the maize ROOTMET2 promoter (WO05063998, published Jul. 14, 2005)) was combined with a 538 bp maize ADHI i-intron 1 fragment for enhanced expression of the trait gene in transgenic maize plants. A Crw1 cassette that contained the 1927 bp Rm2/ADHI promoter-intron fragment, a 2020 bp Crw1 genomic fragment, and a 313 bp PinII terminator was ligated into in the Gateway entry vector pENTR2B containing attL1, L2 recombination sites. This intermediate vector was then combined in an LR recombination reaction with a destination vector. This construct was then introduced into maize via *Agrobacterium*-mediated transformation.

What is claimed is:

1. A method of increasing resistance to herbivory by corn rootworm in a plant, said method comprising:
   (a) introducing into a regenerable plant cell a recombinant DNA construct comprising a polynucleotide operably linked to at least one regulatory sequence, wherein the polynucleotide encodes a polypeptide having an amino acid sequence of at least 99% sequence identity when compared to SEQ ID NO: 3; and wherein the at least one regulatory sequence is a root-specific promoter; and
   (b) regenerating a transgenic plant from the regenerable plant cell after step (a), wherein the transgenic plant comprises in its genome the recombinant DNA construct; and
   (c) evaluating the transgenic plant for increased resistance to corn rootworm when compared to a control plant not comprising the recombinant DNA construct.

2. The method of claim 1, further comprising:
   (d) obtaining a progeny plant derived from the transgenic plant, wherein said progeny plant comprises in its genome the recombinant DNA construct and exhibits increased resistance to herbivory by corn rootworm when compared to a control plant not comprising the recombinant DNA construct.

3. The method of claim 1, wherein said plant is a monocot.

4. The method of claim 3, wherein said monocot is maize.

* * * * *

```
                             SEQUENCE LISTING

<160> NUMBER OF SEQ ID NOS: 34

<210> SEQ ID NO 1
<211> LENGTH: 4695
<212> TYPE: DNA
<213> ORGANISM: Zea mays

<400> SEQUENCE: 1
tgtcgatttt gtgatccaaa ttctgaagaa gacggctaaa ttgacgagcg aagcggaggc      60
tcccccgtct tcgggaggct tatcttttt ttcctaataa gatttattta tattattact     120
ttgtgtgtgc atgcatgtgc actgtatata tatgtcattt gtactttgat gcgagtgaca    180
ccaacagctg gtccatccat atgggagaag aagaagaagc tagtgccaca catatgcatt    240
gatcagctct gtaccaggct agctagctgc ttcttatgta tgcaggcaga tagtagccag    300
gggtagtaat tataattatt atatgaagca gccagagaag aggacacaaa taaaataata    360
gagacgagat gggatggata tatatatata tatatatata tataaagaac acgaatatta    420
gaccaccatc ctcaaaagat tccaaggcta ggcgtgtcaa tatctatagt taagttgtgt    480
gtgtgtgtat atatataaat tctactaatt ccttatatat acacagacat atgtatatga    540
tactatgtac gtaggtacgt gtatatatat gggtacgtcc gtacgagagc aatataacgc    600
atggagcaag agaaatggaa aaccgttggc tttgtcctct cccttctct ctcttaattt     660 ctactgctcg tagtacgtac tagcaaggat gcagtgcagc acctttcctc tgtctctctc    720
tctctctctc tctctctctc ctgcgtctct ctcaggagtg ggtggcaaaa ctaacccca     780 ctgctactag cagctaggag ctctgcagca gggctagcta gctgcagtg cactgaccga     840 cgactcttat ctactagaag atgtggtcgt accagtattg tattgtgtag agagagagag    900
aaagagctag cagccagcag cagcagcaga tacgtacagg tacaacaagc agagctatct    960
aggtaggtag caacagagag agagagagag tgaagcaggc agaggcagca gcatggaaat   1020
ggaatggtgg ccatatgatt catggatgat gggtgcatgg tggacgcgat cgaatcgaac   1080
gcgatcccct cccccctcac ccctaatttt cactcggatc catgcctgtg tgtgctagct   1140
gccgtcgtcg gccttgcctc gcaaaagtac ccccaacccc ccactatata taagtgcagc   1200 gccttttcctc ccctgccacc accagcttcc ctcctagctc ttctctttcc tcatcatcgt  1260
cttcctcccc tcacatcctc tggcctctgg tcctccaccg tcctgctagc cagagctgct   1320
cttgtacgcg cagctggcct ctgtgcatat caccagcaca ccgcgcaggg gaaggaaatt   1380
aacaagagaa aaggcaagga gagcaggcag gcaaggaagc tgcagaagcc aaggaaggag   1440
aaggaggatc atcaatgagc atctcggtga acgggcagtc gtgcgtgccg ccggggttcc   1500 gcttccacc cacggaggag gagctgctca actactacct ccgcaagaag gtggcctccc    1560
aggagatcga cctcgacgtc atccgcgacg tcgacctcaa caagctcgag ccatgggaca   1620
tccaaggtac gtacgtacgc acggccggtc cggtccgatc cggtaccact gccttcttca   1680
acttcaagtt caagcacgcg cgcgcgcagt agcagagcag ctcgtggtcg tggatcagat   1740
cggatcggag ctggtgcacg accatgagag cacggacatg aacatgaaca gaccttgttg   1800
tgaatgcaac tgccttagct agctaccaag caagtactct cgttcgtaca gcagcatgta   1860
tagcttatgt tcgttgatcg acaaaactag ctagcaaaca atcaaacgcg atcgaattca   1920
```

```
tcgcgcgcta actactggct aacaactgct actactacta aagccgctag ctccattcca      1980
tgcatggaaa tcgcgcgcag agaaatgcaa gatcgggtcg ggtccccaga acgactggta      2040
cttcttcagc cacaaggaca agaagtaccc gacggggacg cgcaccaacc gcgccacggc      2100
cgccgggttc tggaaggcca ccggccgcga caaggccatc tacaacgccg tcaagcgcat      2160
cggcatgcgc aagacgctcg tcttctacaa gggccgcgcg ccgcacggcc agaagtccga      2220
ctggatcatg cacgagtacc gcctcgacga ccccgctgct gctgctgctg ctggatccgg      2280
tgatgccgtg gccaacgacg acgcagccgc cacggtaagc aaagcaacga ccctgatcgc      2340
cgttaatctc ttctctgcac caccagttca cgtacgccac cattaataat tgcctgccgt      2400
aagataagaa acaattatat ggcggtggtg gtgcaatcat gcgagtacgg cgacccgcct      2460
tgatttgatc cagctccagg ctcaaggctc cggccgtatt tttttccgct ctcttgtttt      2520
gattgattga tgaggaggag agagagagca gtaggcgcta gctactagct agctagggga      2580
aggaggagg gacggacgta gtaataatta ttaaactttg ccatgtgcct catgtgcccc      2640
aaaaggtagc aataattaac actgctgcac tgttttttt taatctgctt cttgtcgact      2700
tgtcgtcggc ggcgatgtcg cggtggacag gctgctgctg ctgccgccgc gtcgtcggac      2760
ggcgggcagg aggacggctg gtggtgtgc agggtgttca agaagaagca ccaccacaag      2820
gagtcaggtg ggggcggggg caacaagcac ggcagcagta acagcgagca tgggcacggc      2880
ggcgccggca aggcatcggc tgcggctgcg gctgcggcgc accagcacca gcaccatgga      2940
ggcctgcagt actcctccag cgacgaggcg ctggaccaga tcctgcagta catgggcagg      3000
tcgtgcaagc aggagcacga gctggtgtcg ccggcgccgg cgccgccggg acgggcggcg      3060
gcgtccaggt acctccggcc catcgagacc gttctgggcg ggcacgcgtt catgaagctt      3120
cccgcgctcg agagcccgtc cgcggccgcg tccgcatcgc tgacacagcc ggcgcagcac      3180
gacgagctct accgcgccgc cgggaacggg atcacggact gggccatgat ggaccggctg      3240
gtggcgtcgc acctgaacgg gcagcaggcg cccgccgcgg cggaccagct cggcggcggc      3300
tgcggcttcg acgcggacgc cggcgccgaa gacgcggacg ccggcctcgc cttctactcc      3360
gccgccgcca gccggctgct cggctccggc ggcggcgccg cagcgacga cgacctgtgg      3420
agcttcacgc ggtcgtcggt ttcgtcaacg gcggcggcgg cggccacgtc cacggagcgg      3480
ctcagccacg tgtcactgta gacgccgttc ttcgtcgccg tcgccgtcgc cttaactatg      3540
tacgtacgta cgtcgtaagc ccctacgtga tgacatggcc agcatgccct ggtggtacac      3600
gtactagtaa agaagagaca aacaccaaca gcaggagcag agagagagaa agaggaaata      3660
aaagaagggt ctctagagag agagagagtg atttcagagg aggtgattag agtgatgaga      3720
gagactgaaa gtagatcgat ggatcgctga ttcgctgata cgattaaagc tggcagtaag      3780
ttggagtggc actgtcactc ggacgccaca tgcatcatct ctcctttcta tagcttcatt      3840
ctctctccat catctcagcc actgtttaat taaccccccgg ccaccgattg ttattactat      3900
aatatataac cacagcattt tactagcaga ttgatactac atctaccact gttactatat      3960
attagattgt tcatttcaat ataattagga gagagaggag gggagtaatt aattgacagc      4020
gagcagcatg gcaaaacag tgtaaggcga ttattattgc tggtttgttt actagtacct      4080
acctacgtac gtgctgtggg cggtgtgtgt gcatggtgtt tgcagtttgc acatgtgcat      4140
cctttatttt taattattcc catgactata tatatagata ttaaatatac atgcaggttg      4200
tatctatcta tctatacata caaattgcat ttctgtctgt ctctccctct gaatatgaat      4260
gataccgtg cattaatttg tccgtggctg ccagctgcat caattccac ctgtgtgaga       4320
```

```
tatatatagt cctaaccaac acttgaccat gcattctttt tttttcttgg acaatagagc   4380
taatgagcta taggtaccag ccagtagcta atttgtagct agctacagat agcctctaga   4440
gcgtccggcg ccctggcta ggtgtgtcct atcatgcatc acccagccat taactttgaa    4500
ttgcctttat ctgcgttgaa tgcatgcatg tatgtatgcc ctctaacaac agatgccatt   4560
aggccgtctc gtttaattag gacactgaca cgcgcgttct tcaacgtgac actttgacat   4620 gcaatttcg ttacctccgc cgcgcgtgtg tgccaaagat gatgccacca taagttatgg    4680
tttaaatgga gctat                                                    4695
```

<210> SEQ ID NO 2
<211> LENGTH: 1257
<212> TYPE: DNA
<213> ORGANISM: Zea mays

<400> SEQUENCE: 2

```
atgagcatct cggtgaacgg gcagtcgtgc gtgccgccgg ggttccgctt ccaccccacg     60
gaggaggagc tgctcaacta ctacctccgc aagaaggtgg cctcccagga gatcgacctc   120
gacgtcatcc gcgacgtcga cctcaacaag ctcgagccat gggacatcca agagaaatgc   180
aagatcgggt cgggtcccca gaacgactgg tacttcttca gccacaagga caagaagtac   240
ccgacgggga cgcgcaccaa ccgcgccacg gcgccgggt tctggaaggc caccggccgc    300
gacaaggcca tctacaacgc cgtcaagcgc atcggcatgc gcaagacgct cgtcttctac   360
aagggccgcg cgccgcacgg ccagaagtcc gactggatca tgcacgagta ccgcctcgac   420
gaccccgctg ctgctgctgc tgctggatcc ggtgatgccg tggccaacga cgacgcagcc   480
gccacggctg ctgctgctgc cgccgcgtcg tcggacggcg ggcaggagga cggctgggtg   540
gtgtgcaggg tgttcaagaa gaagcaccac cacaaggagt caggtggggg cggggcaac    600 aagcacggca gcagtaacag cgagcatggg cacggcggcg ccggcaaggc atcggctgcg   660
gctgcggctg cggcgcacca gcaccagcac catggaggcc tgcagtactc ctccagcgac   720
gaggcgctgg accagatcct gcagtacatg ggcaggtcgt gcaagcagga gcacgagctg   780
gtgtcgccgg cgccggcgcc gccgggacgg gcggcggcgt ccaggtacct ccggcccatc   840
gagaccgttc tgggcgggca cgcgttcatg aagcttcccg cgctcgagag cccgtccgcg   900
gccgcgtccg catcgctgac acagccggcg cagcacgacg agctctaccg cgccgccggg   960
aacgggatca cggactgggc catgatggac cggctggtgg cgtcgcacct gaacgggcag  1020
caggcgcccg ccgcggcgga ccagctcggc ggcggctgcg gcttcgacgc ggacgccggc  1080
gccgaagacg cggacgccgg cctcgccttc tactccgccg ccgccagccg gctgctcggc  1140
tccggcggcg gcgccggcag cgacgacgac ctgtggagct tcacgcggtc gtcggtttcg  1200
tcaacggcgg cggcggcggc cacgtccacg gagcggctca gccacgtgtc actgtag     1257
```

<210> SEQ ID NO 3
<211> LENGTH: 418
<212> TYPE: PRT
<213> ORGANISM: Zea mays

<400> SEQUENCE: 3

```
Met Ser Ile Ser Val Asn Gly Gln Ser Cys Val Pro Pro Gly Phe Arg
1               5                   10                  15

Phe His Pro Thr Glu Glu Glu Leu Leu Asn Tyr Tyr Leu Arg Lys Lys
            20                  25                  30
```

```
Val Ala Ser Gln Glu Ile Asp Leu Asp Val Ile Arg Asp Val Asp Leu
             35                  40                  45

Asn Lys Leu Glu Pro Trp Asp Ile Gln Glu Lys Cys Lys Ile Gly Ser
 50                  55                  60

Gly Pro Gln Asn Asp Trp Tyr Phe Phe Ser His Lys Asp Lys Lys Tyr
 65                  70                  75                  80

Pro Thr Gly Thr Arg Thr Asn Arg Ala Thr Ala Ala Gly Phe Trp Lys
                 85                  90                  95

Ala Thr Gly Arg Asp Lys Ala Ile Tyr Asn Ala Val Lys Arg Ile Gly
            100                 105                 110

Met Arg Lys Thr Leu Val Phe Tyr Lys Gly Arg Ala Pro His Gly Gln
            115                 120                 125

Lys Ser Asp Trp Ile Met His Glu Tyr Arg Leu Asp Asp Pro Ala Ala
130                 135                 140

Ala Ala Ala Ala Gly Ser Gly Asp Ala Val Ala Asn Asp Asp Ala Ala
145                 150                 155                 160

Ala Thr Ala Ala Ala Ala Ala Ser Ser Asp Gly Gly Gln Glu
                165                 170                 175

Asp Gly Trp Val Val Cys Arg Val Phe Lys Lys Lys His His His Lys
            180                 185                 190

Glu Ser Gly Gly Gly Gly Asn Lys His Gly Ser Ser Asn Ser Glu
            195                 200                 205

His Gly His Gly Ala Gly Lys Ala Ser Ala Ala Ala Ala Ala Ala
            210                 215                 220

Ala His Gln His Gln His His Gly Gly Leu Gln Tyr Ser Ser Ser Asp
225                 230                 235                 240

Glu Ala Leu Asp Gln Ile Leu Gln Tyr Met Gly Arg Ser Cys Lys Gln
                245                 250                 255

Glu His Glu Leu Val Ser Pro Ala Pro Ala Pro Gly Arg Ala Ala
            260                 265                 270

Ala Ser Arg Tyr Leu Arg Pro Ile Glu Thr Val Leu Gly Gly His Ala
            275                 280                 285

Phe Met Lys Leu Pro Ala Leu Glu Ser Pro Ser Ala Ala Ala Ser Ala
290                 295                 300

Ser Leu Thr Gln Pro Ala Gln His Asp Glu Leu Tyr Arg Ala Ala Gly
305                 310                 315                 320

Asn Gly Ile Thr Asp Trp Ala Met Met Asp Arg Leu Val Ala Ser His
                325                 330                 335

Leu Asn Gly Gln Gln Ala Pro Ala Ala Ala Asp Gln Leu Gly Gly Gly
            340                 345                 350

Cys Gly Phe Asp Ala Asp Ala Gly Ala Glu Asp Ala Asp Ala Gly Leu
            355                 360                 365

Ala Phe Tyr Ser Ala Ala Ser Arg Leu Leu Gly Ser Gly Gly Gly
            370                 375                 380

Ala Gly Ser Asp Asp Asp Leu Trp Ser Phe Thr Arg Ser Ser Val Ser
385                 390                 395                 400

Ser Thr Ala Ala Ala Ala Ala Thr Ser Thr Glu Arg Leu Ser His Val
                405                 410                 415

Ser Leu

<210> SEQ ID NO 4
<211> LENGTH: 1265
<212> TYPE: DNA
<213> ORGANISM: Zea mays
```

<400> SEQUENCE: 4

```
atgagcatct cggtgaacgg gcagtcgtgc gtgccgccgg ggttccgctt ccaccccacg    60
gaggaggagc tgctcaacta ctagtctact acctccgcaa gaaggtggcc tcccaggaga   120
tcgacctcga cgtcatccgc gacgtcgacc tcaacaagct cgagccatgg acatccaag    180
agaaatgcaa gatcgggtcg ggtccccaga cgactggta cttcttcagc cacaaggaca   240
agaagtaccc gacggggacg cgcaccaacc gcgccacggc cgccgggttc tggaaggcca   300
ccggccgcga caaggccatc tacaacgccg tcaagcgcat cggcatgcgc aagacgctcg   360
tcttctacaa gggacgcgcg ccgcacggcc agaagtccga ctggatcatg cacgagtacc   420
gcctcgacga ccccgctgct gctgctgctg ctggatccgg tgatgccgtg gccaacgacg   480
acgcagccgc cacggctgct gctgctgccg ccgcgtcgtc ggacggcggg caggaggacg   540
gctgggtggt gtgcagggtg ttcaagaaga agcaccacca caaggagtca ggtgggggcg   600
ggggcaacaa gcacggcagc agtaacagcg agcatgggca cggcggcgcc ggcaaggcat   660
cggctgcggc tgcggctgcg gcgcaccagc accagcacca tggaggcctg cagtactcct   720
ccagcgacga ggcgctggac cagatcctgc agtacatggg caggtcgtgc aagcaggagc   780
acgagctggt gtcgccggcg ccggcgccgc cgggacgggc ggcggcgtcc aggtacctcc   840
ggcccatcga ccgttctg gcgggcacg cgttcatgaa gcttcccgcg ctcgagagcc   900
cgtccgcggc cgcgtccgca tcgctgacac agccggcgca gcacgacgag ctctaccgcg   960
ccgccgggaa cggatcacg gactgggcca tgatggaccg gctggtggcg tcgcacctga  1020
acgggcagca ggcgcccgcc gcggcggacc agctcggcgg cggctgcggc ttcgacgcgg  1080
acgccggcgc cgaagacgcg gacgccggcc tcgccttcta ctccgccgcc gccagccggc  1140
tgctcggctc cggcggcggc gccggcagcg acgacgacct gtggagcttc acgcggtcgt  1200
cggtttcgtc aacggcggcg gcggcggcca cgtccacgga gcggctcagc cacgtgtcac  1260
tgtag                                                              1265
```

<210> SEQ ID NO 5
<211> LENGTH: 27
<212> TYPE: PRT
<213> ORGANISM: Zea mays

<400> SEQUENCE: 5

```
Met Ser Ile Ser Val Asn Gly Gln Ser Cys Val Pro Pro Gly Phe Arg
1               5                   10                  15
Phe His Pro Thr Glu Glu Glu Leu Leu Asn Tyr
            20                  25
```

<210> SEQ ID NO 6
<211> LENGTH: 1258
<212> TYPE: DNA
<213> ORGANISM: Zea mays

<400> SEQUENCE: 6

```
atgagcatct cggtgaacgg gcagtcgtgc gtgccgccgg ggttccgctt ccaccccacg    60
gaggaggagc tgctcaacta ctacctccgc aagaaggtgg cctcccagga gatcgacctc   120
gacgtcatcc gcgacgtcga cctcaacaag ctcgagccat gggacatcca agagaaatgc   180
aagatcgggt cgggtcccca gaacgactgg tacttcttca gccacaagga caagaagtac   240
ccgacgggga cgcgcaccaa ccgcgccacg gccgccgggt tctggaaggc caccggccgc   300
```

| | |
|---|---|
| gacaaggcca tctacaacgc cgtcaagcgc atcggcatgc gcaagacgct cgtcttctac | 360 |
| aagggcccgg cgccgcacg gccagaagtc cgactggatc atgcacgagt accgcctcga | 420 |
| cgaccccgct gctgctgctg ctgctggatc cggtgatgcc gtggccaacg acgacgcagc | 480 |
| cgccacggct gctgctgctg ccgccgcgtc gtcggacggc gggcaggagg acggctgggt | 540 |
| ggtgtgcagg gtgttcaaga agaagcacca ccacaaggag tcaggtgggg gcgggggcaa | 600 |
| caagcacggc agcagtaaca gcgagcatgg gcacggcggc gccggcaagg catcggctgc | 660 |
| ggctgcggct gcggcgcacc agcaccagca ccatggaggc ctgcagtact cctccagcga | 720 |
| cgaggcgctg gaccagatcc tgcagtacat gggcaggtcg tgcaagcagg agcacgagct | 780 |
| ggtgtcgccg gcgccggcgc cgccgggacg ggcggcggcg tccaggtacc tccggcccat | 840 |
| cgagaccgtt ctgggcgggc acgcgttcat gaagcttccc gcgctcgaga gcccgtccgc | 900 |
| ggccgcgtcc gcatcgctga cacagccggc gcagcacgac gagctctacc gcgccgccgg | 960 |
| gaacgggatc acggactggg ccatgatgga ccggctggtg gcgtcgcacc tgaacgggca | 1020 |
| gcaggcgccc gccgcggcgg accagctcgg cggcggctgc ggcttcgacg cggacgccgg | 1080 |
| cgccgaagac gcggacgccg gcctcgcctt ctactccgcc gccgccagcc ggctgctcgg | 1140 |
| ctccggcggc ggcgccggca gcgacgacga cctgtgagc ttcacgcggt cgtcggtttc | 1200 |
| gtcaacggcg gcggcggcgg ccacgtccac ggagcggctc agccacgtgt cactgtag | 1258 |

<210> SEQ ID NO 7
<211> LENGTH: 151
<212> TYPE: PRT
<213> ORGANISM: Zea mays

<400> SEQUENCE: 7

Met Ser Ile Ser Val Asn Gly Gln Ser Cys Val Pro Pro Gly Phe Arg
1               5                   10                  15

Phe His Pro Thr Glu Glu Leu Leu Asn Tyr Tyr Leu Arg Lys Lys
            20                  25                  30

Val Ala Ser Gln Glu Ile Asp Leu Asp Val Ile Arg Asp Val Asp Leu
        35                  40                  45

Asn Lys Leu Glu Pro Trp Asp Ile Gln Glu Lys Cys Lys Ile Gly Ser
    50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Asn Ala Val Lys Arg Ile Gly
            100                 105                 110

Met Arg Lys Thr Leu Val Phe Tyr Lys Gly Pro Gly Ala Ala Arg Pro
        115                 120                 125

Glu Val Arg Leu Asp His Ala Arg Val Pro Pro Arg Pro Arg Cys
    130                 135                 140

Cys Cys Cys Cys Trp Ile Arg
145                 150

<210> SEQ ID NO 8
<211> LENGTH: 1297
<212> TYPE: DNA
<213> ORGANISM: Zea mays

<400> SEQUENCE: 8

| | |
|---|---|
| atgagcatct cggtgaacgg gcagtcgtgc gtgccgccgg ggttccgctt ccaccccacg | 60 |

-continued

```
gaggaggagc tgctcaacta ctacctccgc aagaaggtgg cctcccagga gatcgacctc    120
gacgtcatcc gcgacgtcga cctcaacaag ctcgagccat gggacatcca agagaaatgc    180
aagatcgggt cgggtcccca gaacgactgg tacttcttca gccacaagga caagaagtac    240
ccgacgggga cgcgcaccaa ccgcgccacg gccgccgggt tctggaaggc caccggccgc    300
gacaaggcca tctacaacgc cgtcaagcgc atcggcatgc gcaagacgct cgtcttctac    360
aaagggacgg gcgccgcacg gccagaagtc cgactggatc atgcacgagt accgcctcga    420
cgaccccgct gctgctgctg ctgctggatc cggtaacctg ctggatccgc tgctgctgga    480
tcatgcacga gtatctgctg atgccgtggc aacgacgcc gctgccgctg ccgccacggc    540
tgctgctgct gccgccgcgt cgtcggacgg cgggcaggag acggctgggt ggtgtgcag    600 ggtgttcaag aagaagcacc accacaagga gtcaggcggg ggcgggggtg gcaagcacgg    660
cagcagtaac agcgagcgtg ggcacggcgg cgccggcaag gcatcggcgg cggctgccgg    720
gaaccagctc cacggaggcc tgcagtactc ctccagcgac gaggcgctgg accagatcct    780
gcagtacatg ggcaggtcgt gcaagcagga gcacgagctg gtgtcgccgg cgccggcgcc    840
gccgggacgg gcgcggcgt ccaggtacct ccggcccatc gagaccgttc tgggcgggca    900
cgcgttcatg aagctgcccg cgctcgagag cccgtccgcg gccgcggccg catcgctgac    960
acagccggcg cagcacgacg agctctaccg gccgccgggg aacgggatca cggactgggc   1020
catgatggac cggctggtgg cgtcgcacct gaacgggcag caggcgcccg ccgcggcgga   1080
ccagctcggc ggcggctgcg gcttcgacgg ggacgccggc gccgaagacg cggacgccgg   1140
cctcgccttc tactccgccg ccgccagccg gctgctcggc tccggcggcg cgccggcag   1200 cgacgacgac ctgtggagct tcacgcggtc gtcggtttcg tcaacggcgg cggcggcggc   1260
cacgtccacg gagcggctca gccacgtgtc actgtag                            1297
```

<210> SEQ ID NO 9
<211> LENGTH: 151
<212> TYPE: PRT
<213> ORGANISM: Zea mays

<400> SEQUENCE: 9

```
Met Ser Ile Ser Val Asn Gly Gln Ser Cys Val Pro Pro Gly Phe Arg
1               5                   10                  15

Phe His Pro Thr Glu Glu Leu Leu Asn Tyr Tyr Leu Arg Lys Lys
            20                  25                  30

Val Ala Ser Gln Glu Ile Asp Leu Asp Val Ile Arg Asp Val Asp Leu
        35                  40                  45

Asn Lys Leu Glu Pro Trp Asp Ile Gln Glu Lys Cys Lys Ile Gly Ser
    50                  55                  60

Gly Pro Gln Asn Asp Trp Tyr Phe Ser His Lys Asp Lys Lys Tyr
65                  70                  75                  80

Pro Thr Gly Thr Arg Thr Asn Arg Ala Thr Ala Gly Phe Trp Lys
                85                  90                  95

Ala Thr Gly Arg Asp Lys Ala Ile Tyr Asn Ala Val Lys Arg Ile Gly
            100                 105                 110

Met Arg Lys Thr Leu Val Phe Tyr Lys Gly Thr Gly Ala Ala Arg Pro
        115                 120                 125

Glu Val Arg Leu Asp His Ala Arg Val Pro Pro Arg Pro Arg Cys
    130                 135                 140

Cys Cys Cys Cys Trp Ile Arg
```

```
                    145                 150

<210> SEQ ID NO 10
<211> LENGTH: 400
<212> TYPE: PRT
<213> ORGANISM: Oryza sativa

<400> SEQUENCE: 10

Met Ser Ile Ser Val Asn Gly Gln Ser Cys Val Pro Pro Gly Phe Arg
1               5                   10                  15

Phe His Pro Thr Glu Glu Leu Leu Asn Tyr Tyr Leu Arg Lys Lys
            20                  25                  30

Val Ala Ser Glu Gln Ile Asp Leu Asp Val Ile Arg Asp Val Asp Leu
        35                  40                  45

Asn Lys Leu Glu Pro Trp Asp Ile Gln Glu Arg Cys Lys Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Gly Phe Trp Lys
            85                  90                  95

Ala Thr Gly Arg Asp Lys Ala Ile Tyr Asn Ala Val His Arg Ile Gly
            100                 105                 110

Met Arg Lys Thr Leu Val Phe Tyr Lys Gly Arg Ala Pro His Gly Gln
            115                 120                 125

Lys Ser Asp Trp Ile Met His Glu Tyr Arg Leu Asp Asp Pro Ala Thr
130                 135                 140

Asp Thr Ala Ala Ala Thr Pro Thr Val Thr Ser Ala Ala Ala Ala
145                 150                 155                 160

Ala Ala Met Ala Ala Ala Ala Asp Gly Gly Gln Glu Asp Gly Trp Val
                165                 170                 175

Val Cys Arg Val Phe Lys Lys Lys His His Lys Glu Ala Gly Gly
                180                 185                 190

Gly Gly Gly Lys His Gly Gly Asp Gly Ser Ala Gly Ala Lys Ala Ala
            195                 200                 205

His Ala Tyr Ser Ser Ser Asp Asp Ala Leu Asp Gln Ile Leu Gln Tyr
        210                 215                 220

Met Gly Arg Ser Cys Lys Gln Glu His Glu Leu Pro Ser Pro Gln Ala
225                 230                 235                 240

Ser Gly Gly Gly Gly Ala Gly Ala Gly Ser Arg Pro Ala Ser Arg Tyr
                245                 250                 255

Leu Arg Pro Ile Asp Thr Val Leu Gly Gly His Gly Phe Met Lys Leu
            260                 265                 270

Pro Pro Leu Glu Ser Pro Ser Ala Ala Thr Ala Leu Ser Ser Thr Pro
        275                 280                 285

Ser Thr Gly Gly Asp Ala Ala Ser Ser Ala Ala Ala Ala Ala Asp
        290                 295                 300

His Leu Leu Leu His His His Arg Thr Asp Trp Ala Met Met Asp
305                 310                 315                 320

Arg Leu Val Ala Ser His Leu Asn Gly Ala Asn Ser Asp Ala Pro Asp
                325                 330                 335

Asp Gln Leu Cys Phe Asp Ala Asp Asp Asp Gly Leu Ala Tyr Tyr
            340                 345                 350

Ser Ala Ala Ala Thr Arg Leu Leu Gly Gly Ala Asn Ala Gly Thr Asp
        355                 360                 365
```

Asp Asp Leu Trp Ser Phe Ala Arg Ser Ala Ala Pro Pro Pro Pro
370                 375                 380

Pro Pro Pro Ser Ser Ala Thr Pro Glu Arg Leu Ser His Val Ala Leu
385                 390                 395                 400

<210> SEQ ID NO 11
<211> LENGTH: 395
<212> TYPE: PRT
<213> ORGANISM: Oryza sativa

<400> SEQUENCE: 11

Met Ser Ile Ser Val Asn Gly Gln Ser Val Pro Pro Gly Phe Arg
1               5                   10                  15

Phe His Pro Thr Glu Glu Leu Leu Thr Tyr Tyr Leu Lys Lys Lys
            20                  25                  30

Val Ala Ser Glu Arg Ile Asp Leu Asp Val Ile Arg Asp Val Asp Leu
        35                  40                  45

Asn Lys Leu Glu Pro Trp Asp Ile Gln Glu Arg Cys Arg Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Ser Ser Ser Asn Arg Ile Gly
            100                 105                 110

Met Arg Lys Thr Leu Val Phe Tyr Lys Gly Arg Ala Pro His Gly Gln
        115                 120                 125

Lys Ser Asp Trp Ile Met His Glu Tyr Arg Leu Asp Asp Pro Ser Ser
130                 135                 140

Ala Ser Ala Ser Val Ser Val Asn Leu Pro Ser Tyr Tyr Ser Ser Ser
145                 150                 155                 160

Ser Ser Ser Ser Ser Pro Met His Gly Val Ala Gly Asp Gln Gly Ala
                165                 170                 175

Gln Glu Glu Gly Trp Val Ile Cys Arg Val Phe Lys Lys Lys Asn Leu
            180                 185                 190

Val His His Gly Gly Ala Ala Ala Ala Ser His His Ala Ala Ala
        195                 200                 205

Lys Leu Ala Ala Ala Ala Met Glu Gly Ser Pro Ser Asn Cys Ser Thr
210                 215                 220

Val Thr Val Ser Asp His Val Lys Ala Gln Met Leu His Ser Ser Ala
225                 230                 235                 240

Ser Asp Asp Ala Leu Asp His Ile Leu Gln Tyr Met Gly Arg Ser Gly
                245                 250                 255

Cys Lys Gln Glu Thr Lys Pro Ala Ala Met Ser Ala Ser Ala Ala
            260                 265                 270

Ala Ala Ala Ala Leu Glu Gln His Leu Ser Thr Pro Gln Tyr Gly Lys
        275                 280                 285

Phe Met Lys Leu Pro Pro Leu Glu His Val Ala Gly Val Gly Leu
290                 295                 300

Leu Ala Ala Ala Gly Gly Gly Glu Tyr Cys Ser Ala Ala Asp Ala
305                 310                 315                 320

Ser Gly Ile Ala Asp Trp Asp Thr Leu Asp Arg Leu Ala Ala Ser Tyr
                325                 330                 335

Glu Leu Asn Gly Ala Leu Ser Asp Val Ala Ser Gly Lys Asn Met Ala
            340                 345                 350

```
Gly Phe Phe Asp Val Val Asp Gln Pro Ala Gly Ala Ala Ala Phe Ser
            355                 360                 365

Ser Gly Asp Gly Asp Leu Trp Ser Leu Ala Arg Ser Val Ser Ser Ser
370                 375                 380

Leu His Ala Asp Leu Thr Thr Met Asn Asn Val
385                 390                 395

<210> SEQ ID NO 12
<211> LENGTH: 419
<212> TYPE: PRT
<213> ORGANISM: Sorghum bicolor

<400> SEQUENCE: 12

Met Ser Ile Ser Val Asn Gly Gln Ser Cys Val Pro Pro Gly Phe Arg
1               5                   10                  15

Phe His Pro Thr Glu Glu Leu Leu Asn Tyr Tyr Leu Arg Lys Lys
            20                  25                  30

Val Ala Ser Gln Glu Ile Asp Leu Asp Val Ile Arg Asp Val Asp Leu
        35                  40                  45

Asn Lys Leu Glu Pro Trp Asp Ile Gln Glu Lys Cys Lys Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Asn Ala Val Lys Arg Ile Gly
            100                 105                 110

Met Arg Lys Thr Leu Val Phe Tyr Lys Gly Arg Ala Pro His Gly Gln
            115                 120                 125

Lys Ser Asp Trp Ile Met His Glu Tyr Arg Leu Asp Asp Pro Ala Ala
130                 135                 140

Ser Gly Asp Ala Ala Ala Ala Thr Ala Ala Ala Ala Thr Val
145                 150                 155                 160

Ala Ala Ala Ala Ser Ser Asp Gly Gly Gln Glu Asp Ala Trp Val
                165                 170                 175

Val Tyr Arg Val Phe Lys Lys Lys His His His Lys Glu Ser Ser Gly
            180                 185                 190

Gly Gly Gly Gly Ser Lys His Gly Gly Ser Asn Asn Glu His Gly His
            195                 200                 205

Gly Gly Gly Lys Ala Ala Ala Ala Ala Ala Ala His Gln His
            210                 215                 220

His Gly Gly Leu Gln Tyr Ser Ser Ser Asp Asp Ala Leu Asp Gln Ile
225                 230                 235                 240

Leu Gln Tyr Met Gly Arg Ser Cys Lys Gln Glu His Glu Leu Leu Ser
                245                 250                 255

Pro Pro Pro Pro Gly Arg Ala Ala Ser Arg Tyr Leu Arg Pro Ile Glu
            260                 265                 270

Thr Val Leu Gly Gly His Gly Phe Met Lys Leu Pro Pro Leu Glu Ser
            275                 280                 285

Pro Ser Ala Ala Ala Ala Met Thr Pro Gln Ala Val Ser Gly Asp Ala
            290                 295                 300

Gly Val Val Asp Asp Leu Leu Gly Leu His Arg Gly Ile Gly Asn
305                 310                 315                 320

Gly Ile Thr Asp Trp Ala Met Met Asp Arg Leu Val Ala Ser His Leu
```

```
              325                 330                 335
Asn Gly Gln Glu Ala Pro Asp Val Ala Pro Ala Ala Asp Gln Leu Gly
                340                 345                 350

Ser Cys Phe Asp Asp Ala Thr Gly Ala Asp Ala Asp Ala Ala Gly
            355                 360                 365

Leu Ala Phe Tyr Ser Ala Ala Ala Asn Arg Leu Leu Val Gly Ser Ala
        370                 375                 380

Gly Ser Ser Gly Ala Gly Ser Asp Asp Leu Trp Ser Phe Thr Arg
385                 390                 395                 400

Ser Ser Ala Ala Ala Ala Ala Thr Ser Thr Glu Arg Leu Ser His
                405                 410                 415

Val Ser Leu

<210> SEQ ID NO 13
<211> LENGTH: 428
<212> TYPE: PRT
<213> ORGANISM: Sorghum bicolor

<400> SEQUENCE: 13

Met Ser Ile Ser Val Asn Gly Gln Ser Val Pro Pro Gly Phe Arg
1               5                   10                  15

Phe His Pro Thr Glu Glu Leu Leu Thr Tyr Tyr Leu Lys Lys Lys
                20                  25                  30

Val Ala Ser Glu Arg Ile Asp Leu Asp Val Ile Arg Asp Val Asp Leu
            35                  40                  45

Asn Lys Leu Glu Pro Trp Asp Ile Gln Glu Lys Cys Arg Ile Gly Ser
        50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Ala Ser Gly Ala Arg Arg Ile
            100                 105                 110

Gly Met Arg Lys Thr Leu Val Phe Tyr Lys Gly Arg Ala Pro His Gly
        115                 120                 125

Gln Lys Ser Asp Trp Ile Met His Glu Tyr Arg Leu Glu Pro Ala Leu
130                 135                 140

Asp Val Asp Ala Ala Ala Gly Ser Ala Ser Ala His His Ala Ala Ala
145                 150                 155                 160

Gly Ala Ala Ala Asp His His Pro Tyr Tyr Thr Ser Ser Ser Pro Pro
                165                 170                 175

Ala Leu Pro Thr Ala Ile Arg Gly Ala Ala Gly Asp Gln Gln Ala Ala
            180                 185                 190

Gln Glu Gln Glu Gly Trp Val Ile Cys Arg Val Phe Lys Lys Lys Asn
        195                 200                 205

Leu Val His His Gly Gln Ser Ser Gly Gly Val Thr Ala Ala Gly
210                 215                 220

Ser Lys Met Ala Ser Ala Ala Pro Met Glu Gly Ser Pro Ser His
225                 230                 235                 240

Cys Ser Ser Val Thr Val Ile Ser Asp His Thr Met Asn Lys His Gln
                245                 250                 255

Ala Gln Ala Met Leu Gln His Ser Ala Ser Asp Asp Ala Leu Asp
            260                 265                 270

His Ile Leu Gln Tyr Met Gly Gly Gly Gly Gly Lys Gln Pro Asp Thr
```

```
                275                 280                 285
Lys Pro Val Leu Leu Asp His His His His His Leu Ala Ala Ala
290                 295                 300
Ala Thr Thr Thr Thr Thr Ala Cys Ser Ala Gly Gly Ala Gly Leu Tyr
305                 310                 315                 320
Gly Lys Phe Met Lys Leu Pro Pro Leu Glu His Ala Gly Gly Gly
                325                 330                 335
Gly Leu Leu Pro Ser Pro Ala Gly Ala Cys Asp Tyr Gly Ala Ala Asp
                340                 345                 350
Ala Ser Gly Ile Ala Asp Trp Asp Ala Leu Asp Arg Leu Ala Ala Tyr
            355                 360                 365
Glu Leu Asn Gly Leu Ser Asp Ala Ser Lys Asn Met Ser Ala Phe Phe
370                 375                 380
Asp Glu Pro Ser Ala Thr Ala Ala Phe Ser Ser Ser Ser Ser Ser Val
385                 390                 395                 400
His Ala Ala Ala Val Asp Gly Asp Leu Trp Ser Leu Ala Arg Ser Val
                405                 410                 415
Ser Ala Leu His Ala Asp Leu Thr Met Asn Asn Val
            420                 425

<210> SEQ ID NO 14
<211> LENGTH: 388
<212> TYPE: PRT
<213> ORGANISM: Glycine max

<400> SEQUENCE: 14

Met Pro Glu Asn Met Ser Ile Ser Val Asn Gly Gln Ser Gln Val Pro
1               5                   10                  15
Pro Gly Phe Arg Phe His Pro Thr Glu Glu Leu Leu Gln Tyr Tyr
            20                  25                  30
Leu Arg Lys Lys Val Ser Tyr Glu Lys Ile Asp Leu Asp Val Ile Arg
        35                  40                  45
Asp Val Asp Leu Asn Lys Leu Glu Pro Trp Asp Ile Gln Glu Lys Cys
    50                  55                  60
Lys Ile Gly Thr Thr Pro Gln Asn Asp Trp Tyr Phe Phe Ser His Lys
65                  70                  75                  80
Asp Lys Lys Tyr Pro Thr Gly Thr Arg Thr Asn Arg Ala Thr Ala Ala
                85                  90                  95
Gly Phe Trp Lys Ala Thr Gly Arg Asp Lys Val Ile Tyr Ser Asn Gly
            100                 105                 110
Lys Arg Ile Gly Met Arg Lys Thr Leu Val Phe Tyr Lys Gly Arg Ala
        115                 120                 125
Pro His Gly Gln Lys Ser Asp Trp Ile Met His Glu Tyr Arg Leu Asp
    130                 135                 140
Asp Asn Thr Ser Asp Ile Asn Ile Val Ser Asn Val Met Gly Asp
145                 150                 155                 160
Ala Ala Gln Glu Glu Gly Trp Val Val Cys Arg Ile Phe Lys Lys Lys
                165                 170                 175
Asn His Leu Lys Thr Leu Asp Ser Pro Leu Ala Ser Gly Glu Gly Arg
            180                 185                 190
Arg Ser His Met Phe Asp Ser Cys Asp Glu Gly Ala Leu Glu Gln Ile
        195                 200                 205
Leu Gln Gln Met Gly Arg Gly Cys Lys Glu Glu Ser Ser Tyr Glu Gly
    210                 215                 220
```

```
Asn Tyr Asn Ser Tyr Gly Arg Phe Ala Met Gly Leu Asn Asn Gly Gly
225                 230                 235                 240

Gly Gly Gly Tyr Asn Asp Arg Phe Met Lys Leu Pro Ser Leu Glu Ser
            245                 250                 255

Pro Lys Ser Ala Ser Met Glu Asn His His Asn Thr Asn Asn Asn Cys
        260                 265                 270

Asn Asn Asn Met Lys Ser Gly Gly Leu Thr Asn Trp Ala Ala Leu
    275                 280                 285

Asp Arg Leu Val Ala Ser Gln Leu Asn Gly Gln Thr Asp Ala Ser Arg
290                 295                 300

Gln Leu Gly Cys Ala Phe Asn Asp Pro Thr Met Tyr Cys Thr Ser Val
305                 310                 315                 320

Asp His His Asp Leu His His Gln Ile Pro Thr Leu Arg Ser Ser Ser
                325                 330                 335

Thr Ser Ala Asn Thr Arg Pro Ser Pro Ala Pro Ala Phe Ile Asn Pro
                340                 345                 350

Pro Thr Gln Asp Phe Thr Ser Glu Ile Asp Leu Trp Asn Phe Ser Arg
            355                 360                 365

Ser Thr Ser Ser Leu Leu Ala Ser Ser Glu Pro Leu Cys His Val Ser
370                 375                 380

Asn Thr Ser Val
385

<210> SEQ ID NO 15
<211> LENGTH: 419
<212> TYPE: PRT
<213> ORGANISM: Glycine max

<400> SEQUENCE: 15

Met Pro Glu Asn Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
            20                  25                  30

Leu Arg Lys Lys Val Ser Tyr Glu Lys Ile Asp Leu Asp Val Ile Arg
        35                  40                  45

Asp Val Asp Leu Asn Lys Leu Glu Pro Trp Asp Ile Gln Glu Lys Cys
    50                  55                  60

Lys Ile Gly Thr Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Val Ile Tyr Ser Asn Gly
            100                 105                 110

Lys Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Asp
    130                 135                 140

Asp Asn Asn Thr Ala Asp Thr Asn Ile Val Ser Asn Val Met Gly Asp
145                 150                 155                 160

Ala Ala Gln Glu Glu Gly Trp Val Val Cys Arg Ile Phe Lys Lys Lys
                165                 170                 175

Asn His Leu Lys Thr Leu Asp Ser Pro Leu Ala Ser Gly Glu Asp Arg
            180                 185                 190

Arg Ser His Leu Phe Asp Ser Cys Asp Glu Gly Ala Leu Glu Gln Ile
        195                 200                 205
```

Leu Glu Gln Met Gly Arg Ser Cys Lys Glu Ser Ser Tyr Glu Gly
            210                 215                 220

Asn Tyr Arg Asn Tyr Gly Arg Phe Thr Arg Pro Tyr Glu Thr Thr Gly
225                 230                 235                 240

Leu Asn Asn Gly Gly Gly Tyr Asn Asp Arg Phe Met Lys Leu Pro Ser
            245                 250                 255

Leu Glu Ser Pro Lys Ser Ala Ser Met Glu Ser His His Asn Thr Asn
            260                 265                 270

Asn Asn Asn Asn Met Asn Ser Asn Asn Asn Asn Gly Asp Asn Asn
            275                 280                 285

Glu Asn Asn Asn Asn Gly Tyr His Pro Met Ile Pro Val Glu Met
290                 295                 300

Gly Thr Asp Asn Glu Gly Ser Phe Thr Thr His Gln Val Ser Gly Gly
305                 310                 315                 320

Asp Pro Asn Asn Asn Asn Asn Met Val His Pro Leu Glu Val Gly
            325                 330                 335

Ser Gly Gly Gly Gly Leu Thr Asn Trp Ala Ala Leu Asp Arg Leu Val
            340                 345                 350

Ala Ser Gln Leu Asn Gly Gln Thr Asp Ala Ser Arg Gln Leu Ala Cys
            355                 360                 365

Ala Phe Asn Asp Pro Thr Met Tyr Cys Thr Thr Phe Ile Asn Pro Thr
370                 375                 380

Thr Gln Asp Phe Thr Ser Glu Ile Asp Leu Trp Asn Phe Thr Arg Ser
385                 390                 395                 400

Thr Ser Ser Leu Leu Ala Ser Ser Glu Pro Leu Cys His Val Ser Asn
            405                 410                 415

Thr Ser Val

<210> SEQ ID NO 16
<211> LENGTH: 365
<212> TYPE: PRT
<213> ORGANISM: Arabidopsis thaliana

<400> SEQUENCE: 16

Met Met Ser Lys Ser Met Ser Ile Ser Val Asn Gly Gln Ser Gln Val
1               5                   10                  15

Pro Pro Gly Phe Arg Phe His Pro Thr Glu Glu Leu Leu Gln Tyr
            20                  25                  30

Tyr Leu Arg Lys Lys Val Asn Ser Ile Glu Ile Asp Leu Asp Val Ile
            35                  40                  45

Arg Asp Val Asp Leu Asn Lys Leu Glu Pro Trp Asp Ile Gln Glu Met
50                  55                  60

Cys Lys Ile Gly Thr Thr Pro Gln Asn Asp Trp Tyr Phe Phe Ser His
65                  70                  75                  80

Lys Asp Lys Lys Tyr Pro Thr Gly Thr Arg Thr Asn Arg Ala Thr Ala
            85                  90                  95

Ala Gly Phe Trp Lys Ala Thr Gly Arg Asp Lys Ile Ile Tyr Ser Asn
            100                 105                 110

Gly Arg Arg Ile Gly Met Arg Lys Thr Leu Val Phe Tyr Lys Gly Arg
            115                 120                 125

Ala Pro His Gly Gln Lys Ser Asp Trp Ile Met His Glu Tyr Arg Leu
            130                 135                 140

Asp Asp Asn Ile Ile Ser Pro Glu Asp Val Thr Val His Glu Val Val
145                 150                 155                 160

```
Ser Ile Ile Gly Glu Ala Ser Gln Asp Glu Gly Trp Val Val Cys Arg
            165                 170                 175

Ile Phe Lys Lys Lys Asn Leu His Lys Thr Leu Asn Ser Pro Val Gly
            180                 185                 190

Gly Ala Ser Leu Ser Gly Gly Gly Asp Thr Pro Lys Thr Thr Ser Ser
            195                 200                 205

Gln Ile Phe Asn Glu Asp Thr Leu Asp Gln Phe Leu Glu Leu Met Gly
            210                 215                 220

Arg Ser Cys Lys Glu Glu Leu Asn Leu Asp Pro Phe Met Lys Leu Pro
225                 230                 235                 240

Asn Leu Glu Ser Pro Asn Ser Gln Ala Ile Asn Asn Cys His Val Ser
            245                 250                 255

Ser Pro Asp Thr Asn His Asn Ile His Val Ser Asn Val Val Asp Thr
            260                 265                 270

Ser Phe Val Thr Ser Trp Ala Ala Leu Asp Arg Leu Val Ala Ser Gln
            275                 280                 285

Leu Asn Gly Pro Thr Ser Tyr Ser Ile Thr Ala Val Asn Glu Ser His
            290                 295                 300

Val Gly His Asp His Leu Ala Leu Pro Ser Val Arg Ser Pro Tyr Pro
305                 310                 315                 320

Ser Leu Asn Arg Ser Ala Ser Tyr His Ala Gly Leu Thr Gln Glu Tyr
            325                 330                 335

Thr Pro Glu Met Glu Leu Trp Asn Thr Thr Thr Ser Ser Leu Ser Ser
            340                 345                 350

Ser Pro Gly Pro Phe Cys His Val Ser Asn Gly Ser Gly
            355                 360                 365

<210> SEQ ID NO 17
<211> LENGTH: 358
<212> TYPE: PRT
<213> ORGANISM: Arabidopsis thaliana

<400> SEQUENCE: 17

Met Ala Asp Asn Lys Val Asn Leu Ser Ile Asn Gly Gln Ser Lys Val
1               5                   10                  15

Pro Pro Gly Phe Arg Phe His Pro Thr Glu Glu Leu Leu His Tyr
            20                  25                  30

Tyr Leu Arg Lys Lys Val Asn Ser Gln Lys Ile Asp Leu Asp Val Ile
            35                  40                  45

Arg Glu Val Asp Leu Asn Lys Leu Glu Pro Trp Asp Ile Gln Glu Glu
        50                  55                  60

Cys Arg Ile Gly Ser Thr Pro Gln Asn Asp Trp Tyr Phe Phe Ser His
65                  70                  75                  80

Lys Asp Lys Lys Tyr Pro Thr Gly Thr Arg Thr Asn Arg Ala Thr Val
            85                  90                  95

Ala Gly Phe Trp Lys Ala Thr Gly Arg Asp Lys Ile Ile Cys Ser Cys
            100                 105                 110

Val Arg Arg Ile Gly Leu Arg Lys Thr Leu Val Phe Tyr Lys Gly Arg
            115                 120                 125

Ala Pro His Gly Gln Lys Ser Asp Trp Ile Met His Glu Tyr Arg Leu
            130                 135                 140

Asp Asp Thr Pro Met Ser Asn Gly Tyr Ala Asp Val Val Thr Glu Asp
145                 150                 155                 160

Pro Met Ser Tyr Asn Glu Glu Gly Trp Val Val Cys Arg Val Phe Arg
```

```
                    165                 170                 175
Lys Lys Asn Tyr Gln Lys Ile Asp Asp Cys Pro Lys Ile Thr Leu Ser
            180                 185                 190

Ser Leu Pro Asp Asp Thr Glu Glu Lys Gly Pro Thr Phe His Asn
            195                 200                 205

Thr Gln Asn Val Thr Gly Leu Asp His Val Leu Leu Tyr Met Asp Arg
210                 215                 220

Thr Gly Ser Asn Ile Cys Met Pro Ser Gln Thr Thr Thr Gln His
225                 230                 235                 240

Gln Asp Asp Val Leu Phe Met Gln Leu Pro Ser Leu Glu Thr Pro Lys
                245                 250                 255

Ser Glu Ser Pro Val Asp Gln Ser Phe Leu Thr Pro Ser Lys Leu Asp
            260                 265                 270

Phe Ser Pro Val Gln Glu Lys Ile Thr Glu Arg Pro Val Cys Ser Asn
            275                 280                 285

Trp Ala Ser Leu Asp Arg Leu Val Ala Trp Gln Leu Asn Asn Gly His
            290                 295                 300

His Asn Pro Cys His Arg Lys Ser Phe Asp Glu Glu Glu Asn Gly
305                 310                 315                 320

Asp Thr Met Met Gln Arg Trp Asp Leu His Trp Asn Asn Asp Asn
                325                 330                 335

Val Asp Leu Trp Ser Ser Phe Thr Glu Ser Ser Ser Leu Asp Pro
            340                 345                 350

Leu Leu His Leu Ser Val
            355

<210> SEQ ID NO 18
<211> LENGTH: 334
<212> TYPE: PRT
<213> ORGANISM: Arabidopsis thaliana

<400> SEQUENCE: 18

Met Asn Ile Ser Val Asn Gly Gln Ser Gln Val Pro Pro Gly Phe Arg
1               5                   10                  15

Phe His Pro Thr Glu Glu Leu Leu Lys Tyr Tyr Leu Arg Lys Lys
            20                  25                  30

Ile Ser Asn Ile Lys Ile Asp Leu Asp Val Ile Pro Asp Ile Asp Leu
            35                  40                  45

Asn Lys Leu Glu Pro Trp Asp Ile Gln Glu Met Cys Lys Ile Gly Thr
50                  55                  60

Thr Pro Gln Asn Asp Trp Tyr Phe Tyr Ser His Lys Asp Lys Lys Tyr
65                  70                  75                  80

Pro Thr Gly Thr Arg Thr Asn Arg Ala Thr Thr Val Gly Phe Trp Lys
                85                  90                  95

Ala Thr Gly Arg Asp Lys Thr Ile Tyr Thr Asn Gly Asp Arg Ile Gly
            100                 105                 110

Met Arg Lys Thr Leu Val Phe Tyr Lys Gly Arg Ala Pro His Gly Gln
            115                 120                 125

Lys Ser Asp Trp Ile Met His Glu Tyr Arg Leu Asp Glu Ser Val Leu
130                 135                 140

Ile Ser Ser Cys Gly Asp His Asp Val Asn Val Glu Thr Cys Asp Val
145                 150                 155                 160

Ile Gly Ser Asp Glu Gly Trp Val Val Cys Arg Val Phe Lys Lys Asn
                165                 170                 175
```

```
Asn Leu Cys Lys Asn Met Ile Ser Ser Ser Pro Ala Ser Ser Val Lys
            180                 185                 190

Thr Pro Ser Phe Asn Glu Glu Thr Ile Glu Gln Leu Leu Glu Val Met
        195                 200                 205

Gly Gln Ser Cys Lys Gly Glu Ile Val Leu Asp Pro Phe Leu Lys Leu
    210                 215                 220

Pro Asn Leu Glu Cys His Asn Asn Thr Thr Ile Thr Ser Tyr Gln Trp
225                 230                 235                 240

Leu Ile Asp Asp Gln Val Asn Asn Cys His Val Ser Lys Val Met Asp
                245                 250                 255

Pro Ser Phe Ile Thr Ser Trp Ala Ala Leu Asp Arg Leu Val Ala Ser
            260                 265                 270

Gln Leu Asn Gly Pro Asn Ser Tyr Ser Ile Pro Ala Val Asn Glu Thr
        275                 280                 285

Ser Gln Ser Pro Tyr His Gly Leu Asn Arg Ser Gly Cys Asn Thr Gly
    290                 295                 300

Leu Thr Pro Asp Tyr Tyr Ile Pro Glu Ile Asp Leu Trp Asn Glu Ala
305                 310                 315                 320

Asp Phe Ala Arg Thr Thr Cys His Leu Leu Asn Gly Ser Gly
                325                 330

<210> SEQ ID NO 19
<211> LENGTH: 379
<212> TYPE: PRT
<213> ORGANISM: Zea mays

<400> SEQUENCE: 19

Met Ser Ile Ser Val Asn Gly Gln Ser Cys Val Pro Pro Gly Phe Arg
1               5                   10                  15

Phe His Pro Thr Glu Glu Leu Leu Asn Tyr Tyr Leu Arg Lys Lys
            20                  25                  30

Val Ala Ser Gln Gln Ile Asp Leu Asp Val Ile Arg Asp Val Asp Leu
        35                  40                  45

Asn Lys Leu Glu Pro Trp Asp Ile Gln Glu Arg Cys Lys Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Ser Ala Val Arg Arg Met Gly
            100                 105                 110

Met Arg Lys Thr Leu Val Phe Tyr Arg Gly Arg Ala Pro His Gly His
        115                 120                 125

Lys Ser Asp Trp Ile Met His Glu Tyr Arg Leu Asp Asp Pro Asp Ala
    130                 135                 140

Ala Ala Val Ala Ala Thr Val Ala Ala Ala Ala Ser Ser Asp Gly
145                 150                 155                 160

Gly Gln Glu Asp Gly Trp Val Val Cys Arg Val Phe Gln Lys Lys His
                165                 170                 175

His His Lys Glu Ser Ser Gly Arg Cys Arg Ser Lys Arg Gly Ser Lys
            180                 185                 190

Thr Glu His Gly His Gly Glu Ala Lys Thr Ala Ala His Gln Arg His
        195                 200                 205

Gly Cys Gly Leu Gln Tyr Ser Ser Asn Asp Asp Thr Leu Asp His Met
    210                 215                 220
```

-continued

```
Leu Gly Arg Arg Ser Cys Lys Gln Glu His Glu Leu Leu Pro Leu Pro
225                 230                 235                 240

Pro Pro Ala Ala Ala Arg Ala Ala Ser Arg Tyr Ile Arg Pro Ile Glu
            245                 250                 255

Thr Val Leu Gly Gly His Gly Phe Met Lys Leu Pro Pro Leu Glu Ser
        260                 265                 270

Pro Ala Ala Ala Glu Ala Leu Thr Thr Pro His Ala Val Ser Ala Gly
    275                 280                 285

Asp Ala Thr Ala Ala Gly Ala Leu Asp Gly Leu His Arg Ala Gly Asn
290                 295                 300

Gly Ile Thr Asp Trp Val Met Met Asp Arg Met Val Ala Leu His Leu
305                 310                 315                 320

Asn Gly Gln Ala Pro Ala Ala Asp Gln Leu Gly Ser Cys Phe Asp Ala
            325                 330                 335

Ser Ala Asp Gly Gly Leu Ala Cys Phe Tyr Ser Ala Ala Ala Asn
        340                 345                 350

Arg Leu Leu Gly Gly Asp Asp Leu Trp Ser Phe Thr Arg Ser
    355                 360                 365

Ser Ser Thr Glu Arg Leu Gly His Val Ser Leu
370                 375
```

<210> SEQ ID NO 20
<211> LENGTH: 435
<212> TYPE: PRT
<213> ORGANISM: Zea mays

<400> SEQUENCE: 20

```
Met Ser Ile Ser Val Asn Gly Gln Ser Val Pro Pro Gly Phe Arg
1               5                   10                  15

Phe His Pro Thr Glu Glu Leu Leu Thr Tyr Tyr Leu Lys Lys Lys
            20                  25                  30

Val Ala Ser Glu Arg Ile Asp Leu Asp Val Ile Arg Asp Val Asp Leu
        35                  40                  45

Asn Lys Leu Glu Pro Trp Asp Ile Gln Glu Lys Cys Arg Ile Gly Ser
50                  55                  60

Gly Pro Gln Asn Asp Trp Tyr Phe Phe Ser His Lys Asp Lys Tyr
65                  70                  75                  80

Pro Thr Gly Thr Arg Thr Asn Arg Ala Thr Ala Gly Phe Trp Lys
            85                  90                  95

Ala Thr Gly Arg Asp Lys Ala Ile Tyr Ala Ser Pro Gly Ala Arg Arg
        100                 105                 110

Ile Gly Met Arg Lys Thr Leu Val Phe Tyr Lys Gly Arg Ala Pro His
    115                 120                 125

Gly Gln Lys Ser Asp Trp Ile Met His Glu Tyr Arg Leu Glu Ala Pro
130                 135                 140

Val Asp Ala Gly Ala Gly Ala Ala His His Leu Leu Leu Pro Ala Ala
145                 150                 155                 160

Glu His Pro Pro Tyr Tyr Thr Ser Pro Pro Gln Ala Pro Ser Ser Thr
            165                 170                 175

Thr Thr Ala Thr Ile Arg Gly Ala Ala Gly Asp Gln Ala Ala Gln Glu
        180                 185                 190

Gln Glu Gly Trp Val Ile Cys Arg Val Phe Lys Lys Lys Asn Leu Val
    195                 200                 205

His His Gly Gln Ser Ser Gly Val Lys Gln Gln Ala Ala Gly Asp Asp
```

His Ala Ser His Thr Ala Ala Ala His Met Asp Glu Ser
225                 230                 235                 240

Ser Pro Ser Gln Cys Ser Ser Val Thr Val Ile Ser Asp His Val His
            245                 250                 255

Ala Asn Val Asn Asp Lys Gln Gln Ala Gln Ala Ser Leu Leu Met
                260                 265                 270

Met His Thr His His Ser Ala Ser Ser Asp Asp Ala Leu Asp His
            275                 280                 285

Ile Leu Gln Gln Tyr Met Gly Gly Arg Gln Ala Pro Ala Pro Asp
        290                 295                 300

Thr Lys Pro Ala Leu Leu Glu Gln Leu Asp His Leu His His Leu
305                 310                 315                 320

Ala Ala Ala Pro Thr Thr Arg Ala Ala Gly Phe Tyr Tyr Gly Lys
                325                 330                 335

Phe Met Lys Leu Pro Pro Leu Glu His Ala Gly Leu Pro Pro Ser Pro
            340                 345                 350

Pro Pro Pro Gly Ala Arg Glu Tyr Gly Ala Ala Ala Ala Gly Trp
        355                 360                 365

Asp Asp Asp Asp Ala Leu Asp Arg Leu Ala Ala Tyr Asp His Leu
370                 375                 380

Asn Gly Leu Ser Asn Asp Ala Ser Lys Asn Met Ala Ala Phe Asp
385                 390                 395                 400

Val Glu Pro Ser Ala Ala Ala Ala Val Asp Gly Asp Leu Trp
                405                 410                 415

Ser Leu Ala Arg Ser Val Ser Ala Leu His Ala Asp Leu Thr Met Asn
            420                 425                 430

Asn Asn Val
        435

<210> SEQ ID NO 21
<211> LENGTH: 408
<212> TYPE: PRT
<213> ORGANISM: Brachypodium distachyon

<400> SEQUENCE: 21

Met Ser Ile Ser Val Asn Gly Gln Ser Cys Val Pro Pro Gly Phe Arg
1               5                   10                  15

Phe His Pro Thr Glu Glu Leu Leu Asn Tyr Tyr Leu Arg Lys Lys
            20                  25                  30

Val Ala Ser Gln Gln Ile Asp Leu Asp Val Ile Arg Asp Val Asp Leu
            35                  40                  45

Asn Lys Leu Glu Pro Trp Asp Ile Gln Glu Arg Cys Lys Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Gly Phe Trp Lys
            85                  90                  95

Ala Thr Gly Arg Asp Lys Ala Ile Tyr Asn Ala Val Ser Arg Ile Gly
            100                 105                 110

Met Arg Lys Thr Leu Val Phe Tyr Lys Gly Arg Ala Pro His Gly Leu
        115                 120                 125

Lys Ser Asp Trp Ile Met His Glu Tyr Arg Leu Leu Asp Ala Asp Asp
    130                 135                 140

-continued

```
Ser Ser Ser Ala Ala Thr Ala Met Val Arg Val Ser Val Thr Ala
145                 150                 155                 160

Ser Ser Val Ala Ala Ser Glu Ala Ala Gly Gln Gln Gly Pro Glu Asp
            165                 170                 175

Gly Trp Val Val Cys Arg Val Phe Lys Lys His His His Lys Asp
        180                 185                 190

Thr Asn Ser Gly Ser Gly Ser Gly Ser Gly Asn Lys Lys Ala Ala Ala
        195                 200                 205

Leu Arg Arg Ser Ser Ser Pro Leu Tyr Ser Ser Gly Asp Asp Ala
    210                 215                 220

Ala Leu Asp Gln Ile Leu His Tyr Met Gly Arg Ser Ser Ala Ala Cys
225                 230                 235                 240

Lys Gln Glu His Asp Ser Pro Arg Pro Ala Pro Ala Gln Thr Gln Ala
            245                 250                 255

Gln Ala Arg Pro Thr Ser Arg Tyr Leu Arg Pro Ile Glu Thr Ala Leu
        260                 265                 270

Ala Gly Gly His Gly Phe Met Lys Leu Pro Pro Leu Glu Ser Pro Ser
            275                 280                 285

Ser Ala Ala Ala Ala Pro Pro Asn Thr Thr Pro Val Pro Glu Thr
290                 295                 300

Thr Met Asp Trp Ala Met Met Asp Arg Leu Val Ala Ser His Leu Asn
305                 310                 315                 320

Gly Gln Leu His Asp Asp His Ala Ser Thr Ala Val Val Asp Asp Asp
            325                 330                 335

His Arg Leu Cys Ser Ala Phe Asp Asp Gly Ala Gly Glu Asp Asn Asp
        340                 345                 350

Asp Gly Glu Met Ala Gly Pro Asp Val Glu Arg Pro Val Gly Glu Pro
        355                 360                 365

Ser Arg Gly Ser Ser Ala Ala Gln Leu Ala Val Asn Arg Pro Ser Trp
    370                 375                 380

Lys Lys Lys Val Ser Phe Arg Pro Arg Gly Gly Pro Pro Leu Val Pro
385                 390                 395                 400

Thr Val Pro Val Asp Gly Gly Gly
                405
```

<210> SEQ ID NO 22
<211> LENGTH: 405
<212> TYPE: PRT
<213> ORGANISM: Vitis vinifera

<400> SEQUENCE: 22

```
Met Ser Glu Asp Met Asn Leu Ser Val Asn Gly Gln Ser Gln Val Pro
1               5                   10                  15

Pro Gly Phe Arg Phe His Pro Thr Glu Glu Leu Leu His Tyr Tyr
            20                  25                  30

Leu Arg Lys Lys Val Ala Tyr Glu Lys Ile Asp Leu Asp Val Ile Arg
        35                  40                  45

Asp Val Asp Leu Asn Lys Leu Glu Pro Trp Asp Ile Gln Glu Lys Cys
    50                  55                  60

Lys Ile Gly Ser Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
            85                  90                  95

Gly Phe Trp Lys Ala Thr Gly Arg Asp Lys Val Ile Tyr Ser Ser Phe
        100                 105                 110
```

```
Arg Arg Ile Gly Met Arg Lys Thr Leu Val Phe Tyr Lys Gly Arg Ala
            115                 120                 125

Pro His Gly Gln Lys Ser Asp Trp Ile Met His Glu Tyr Arg Leu Glu
    130                 135                 140

Glu Asn Thr Pro Val His Asp Thr Met Ala Ser Asn Ser Leu Gly Glu
145                 150                 155                 160

Ser Met Pro Glu Asp Gly Trp Val Val Cys Arg Val Phe Arg Lys Lys
                165                 170                 175

Asn Tyr Gln Lys Thr Leu Glu Ser Pro Lys Ser Thr Ser Asn Ser Met
            180                 185                 190

Asp Ser Arg Thr Gln Met Leu Asn Ser Ser Asn Asp Gly Val Leu Asp
        195                 200                 205

Gln Ile Leu Ser Tyr Met Gly Arg Thr Cys Lys Gln Glu Asn Glu Ala
    210                 215                 220

Ile Ser Asn Val Asn Phe Ser Asp Ser Asn Asn Thr Met Arg Phe Leu
225                 230                 235                 240

Asn Gln Asn Asn Thr Gly Ile Ser Glu Gly Leu Gln Glu Arg Phe Met
                245                 250                 255

His Leu Pro Arg Leu Glu Ser Pro Thr Leu Pro Ser Leu Pro Asn Asn
            260                 265                 270

Ser Ser His Phe Asp Gln Glu Arg Cys Phe Asn Ile Ala Cys Leu Gln
        275                 280                 285

Ser Ile Asp Glu Met Leu Arg Gly Ser Glu Pro Ser Ser Glu Asn Gln
    290                 295                 300

Gly Ser Gly Cys Asn Thr Thr Pro Val His Asp Pro Lys Ala Gly Leu
305                 310                 315                 320

Asn Asp Trp Val Ala Phe Asp Arg Leu Val Ala Ser Gln Leu Asn Gly
                325                 330                 335

Gln Val Asp Thr Lys Gln Leu Ser Cys Phe Ser Thr Asp Pro Asn Met
            340                 345                 350

Gly Phe Cys Leu Ser Pro Asp His Asp Val Glu Leu Ser His Leu Arg
        355                 360                 365

Ser Ser Arg Pro Asn Pro Asn Pro Gln Asn Tyr Asn Ser Glu Met Asp
    370                 375                 380

Leu Trp Asn Phe Thr Arg Ser Ser Ser Ser Ser Ser Asp Pro Leu
385                 390                 395                 400

Gly His Leu Ser Val
            405

<210> SEQ ID NO 23
<211> LENGTH: 400
<212> TYPE: PRT
<213> ORGANISM: Glycine max

<400> SEQUENCE: 23

Met Pro Glu Asn Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
            20                  25                  30

Leu Arg Lys Lys Val Ser Tyr Glu Lys Ile Asp Leu Asp Val Ile Arg
        35                  40                  45

Asp Val Asp Leu Asn Lys Leu Glu Pro Trp Asp Ile Gln Glu Lys Cys
    50                  55                  60

Lys Ile Gly Thr Thr Pro Gln Asn Asp Trp Tyr Phe Phe Ser His Lys
```

```
                65                  70                  75                  80
Asp Lys Lys Tyr Pro Thr Gly Thr Arg Thr Asn Arg Ala Thr Ala Ala
                    85                  90                  95
Gly Phe Trp Lys Ala Thr Gly Arg Asp Lys Val Ile Tyr Ser Asn Gly
                100                 105                 110
Lys Arg Ile Gly Met Arg Lys Thr Leu Val Phe Tyr Lys Gly Arg Ala
                115                 120                 125
Pro His Gly Gln Lys Ser Asp Trp Ile Met His Glu Tyr Arg Leu Asp
                130                 135                 140
Asp Asn Thr Ala Asp Thr Asn Ile Val Ser Asn Val Met Gly Asp
145                 150                 155                 160
Ala Ala Gln Glu Glu Gly Trp Val Val Cys Arg Ile Phe Lys Lys Lys
                165                 170                 175
Asn His Leu Lys Thr Leu Asp Ser Pro Leu Ala Ser Gly Glu Asp Arg
                180                 185                 190
Arg Ser His Leu Phe Asp Ser Cys Asp Glu Gly Ala Leu Glu Gln Ile
                195                 200                 205
Leu Glu Gln Met Gly Arg Ser Cys Lys Glu Glu Ser Ser Tyr Glu Gly
                210                 215                 220
Asn Tyr Arg Asn Tyr Gly Arg Phe Thr Arg Pro Tyr Glu Thr Thr Gly
225                 230                 235                 240
Leu Asn Asn Gly Gly Gly Tyr Asn Asp Arg Phe Met Lys Leu Pro Ser
                245                 250                 255
Leu Glu Ser Pro Lys Ser Ala Ser Met Glu Ser His His Asn Thr Asn
                260                 265                 270
Asn Asn Asn Asn Met Asn Ser Asn Asn Asn Asn Gly Asp Asn Asn
                275                 280                 285
Glu Asn Asn Asn Asn Gly Tyr His Pro Met Ile Pro Val Glu Met
                290                 295                 300
Gly Thr Asp Asn Glu Gly Ser Phe Thr Thr His Gln Val Ser Gly Gly
305                 310                 315                 320
Asp Pro Asn Asn Asn Asn Asn Met Val His Pro Leu Glu Val Gly
                325                 330                 335
Ser Gly Gly Gly Gly Leu Thr Asn Trp Ala Ala Leu Asp Arg Leu Val
                340                 345                 350
Ala Ser Gln Leu Asn Gly Gln Thr Asp Ala Ser Arg Gln Leu Ala Cys
                355                 360                 365
Ala Phe Asn Asp Pro Thr Met Tyr Cys Thr Ser Asp His His Asp Leu
                370                 375                 380
His Gln Ile Pro Thr Leu Arg Ser Ser Thr Ser Ala Ala His Thr
385                 390                 395                 400

<210> SEQ ID NO 24
<211> LENGTH: 389
<212> TYPE: PRT
<213> ORGANISM: Gossypium hirsutum

<400> SEQUENCE: 24

Met Asn Leu Ser Ile Asn Gly Gln Ser Gln Val Pro Pro Gly Phe Arg
1               5                   10                  15
Phe His Pro Thr Glu Glu Glu Leu Leu His Tyr Tyr Leu Arg Lys Lys
                20                  25                  30
Val Ala Tyr Glu Lys Ile Asp Leu Asp Val Ile Gln Glu Val Asp Leu
                35                  40                  45
```

Asn Lys Leu Glu Pro Trp Asp Ile Gln Glu Lys Cys Arg Ile Gly Ser
 50                  55                  60

Thr Pro Gln Asn Glu Trp Tyr Phe Phe Ser His Lys Asp Lys Lys Tyr
 65                  70                  75                  80

Pro Thr Gly Thr Arg Thr Asn Arg Ala Thr Ala Gly Phe Trp Lys
                 85                  90                  95

Ala Thr Gly Arg Asp Lys Ile Ile Tyr Ser Gly Phe Arg Arg Ile Gly
                100                 105                 110

Leu Arg Lys Thr Leu Val Phe Tyr Lys Gly Arg Ala Pro His Gly Gln
                115                 120                 125

Lys Ser Asp Trp Ile Met His Glu Tyr Arg Leu Asp Asp Asn Thr Thr
130                 135                 140

Thr His Asp Ser Asn Gly Ser Asn Pro Ile Gly Asp Ser Val Thr Glu
145                 150                 155                 160

Asp Gly Trp Val Val Cys Arg Val Phe Arg Lys Lys Asn Tyr Leu Lys
                165                 170                 175

Thr Leu Glu Ser Pro Lys Ser Asn Ser Ser Thr Gly His Asp Leu
                180                 185                 190

Lys Thr His Met Leu Ser Ser Gly Gly Asn Asp Gly Val Leu Asp Gln
                195                 200                 205

Ile Leu His Tyr Met Gly Arg Thr Cys Lys Met Glu Ser Asp Ser Leu
210                 215                 220

Asn Asn Ile Asn Asn Ile Pro Ile Pro Asp Asn Asn Pro Arg Met Leu
225                 230                 235                 240

Val Gly Asn Asn Gly Gly Ile Asn Asp Gly Phe His Asp His Glu Arg
                245                 250                 255

Phe Met His Leu Pro Arg Leu Glu Ser Pro Thr Leu Pro Ser Leu Cys
                260                 265                 270

Tyr Gln Ser Ile Glu Asp Met Leu Thr Glu Thr Glu His Arg Gly Gly
                275                 280                 285

Cys Cys Gly Gly Gly Gly Asn Asn Glu Thr Lys Asn Gly Val Asn Asp
                290                 295                 300

Trp Val Thr Leu Asp Gln Leu Val Ala Ser Gln Leu Ser Gly Gln Val
305                 310                 315                 320

Glu Thr Ser Lys Gln Leu Ser Cys Phe Ser Asp Pro Asn Ala Val Phe
                325                 330                 335

Ser Leu Cys His Asp Asp Gly Ile Gln Leu Ser His Leu Asn Leu Gln
                340                 345                 350

Arg Ser Asn Gln Ser Ser Gln Val Tyr Ser Asn Asp Asn Asp Leu
                355                 360                 365

Trp Ser Leu Thr Lys Ser Ser Phe Ser Pro Phe Ser Ser Asp Pro Leu
370                 375                 380

Cys His Leu Ser Val
385

<210> SEQ ID NO 25
<211> LENGTH: 401
<212> TYPE: PRT
<213> ORGANISM: Pyrus malus

<400> SEQUENCE: 25

Met Ser Asp Asp His Met Ser Leu Ser Ile Asn Gly Gln Ser Gln Val
1               5                   10                  15

Pro Pro Gly Phe Arg Phe His Pro Thr Glu Glu Glu Leu Leu His Tyr
                20                  25                  30

Tyr Leu Arg Lys Lys Val Ala Phe Glu Arg Ile Asp Leu Asp Val Ile
                35                  40                  45

Arg Glu Val Asp Leu Asn Lys Leu Glu Pro Trp Asp Ile Gln Glu Lys
 50                  55                  60

Cys Lys Ile Gly Ser Thr Pro Gln Asn Asp Trp Tyr Phe Phe Ser His
 65                  70                  75                  80

Lys Asp Lys Lys Tyr Pro Thr Gly Thr Arg Thr Asn Arg Ala Thr Thr
                 85                  90                  95

Ala Gly Phe Trp Lys Ala Thr Gly Arg Asp Lys Ile Ile Tyr Ser Gly
                100                 105                 110

Phe Lys Arg Ile Gly Leu Arg Lys Thr Leu Val Phe Tyr Lys Gly Arg
                115                 120                 125

Ala Pro His Gly Gln Lys Ser Asp Trp Ile Met His Glu Tyr Arg Leu
130                 135                 140

Glu Glu Ser Asn Ser Thr His Asp Thr Thr Val Ser Ser Ser Met Gly
145                 150                 155                 160

Glu Ser Met Thr Glu Glu Gly Trp Val Val Cys Arg Val Phe Lys Lys
                165                 170                 175

Lys Asn Tyr Gln Lys Ala Leu Glu Ser Pro Lys Ala Ser Phe Ser Met
                180                 185                 190

Asp Ser Ser Asn Asn Gln Ile His Gly Ser Arg Asn Asp Gly Val Leu
                195                 200                 205

Asp Gln Ile Leu Met Tyr Met Gly Arg Thr Cys Lys Leu Glu Asn His
                210                 215                 220

Asp Glu Pro Leu Thr Met Asn Asn Ile Ser Glu Arg Phe Met His Leu
225                 230                 235                 240

Pro Arg Leu Glu Ser Pro Thr Leu Pro Asn Leu Pro Ala Phe Asp Gln
                245                 250                 255

Asp Arg Ser Phe Lys Ala Cys Tyr Gln Ala Ile Asp Asp Met Phe Ile
                260                 265                 270

Glu Thr Glu Pro Pro Ser Thr Asn Gln Gln Ser Asn Gly Cys Asp Asn
                275                 280                 285

Asn Glu Leu Val Asp Asp His Glu Asp Pro Lys Arg Arg Val Asn Asp
                290                 295                 300

Trp Val Thr Leu Asp Arg Leu Val Ala Ser Gln Leu Gly Gln Leu Asn
305                 310                 315                 320

Gly Gln Asp Gln Val Thr Pro Lys His Leu Ser Cys Phe Gly Asp Pro
                325                 330                 335

Asn Met Ala Phe Cys Ser Pro Pro Arg Asn Asp His Asp His
                340                 345                 350

Asp Val Gln Leu Ser Tyr Pro Tyr Leu Arg Thr Ser Ser Ser Ser His
                355                 360                 365

His Gln Ser Asp Val Tyr Asn Asn Glu Asn Asp Leu Trp Asn Phe Thr
370                 375                 380

Lys Ser Ser Ser Ser Pro Ser Ser Thr Asp Pro Leu Cys His Leu Ser
385                 390                 395                 400

Val

<210> SEQ ID NO 26
<211> LENGTH: 411
<212> TYPE: PRT
<213> ORGANISM: Hordeum vulgare

<400> SEQUENCE: 26

-continued

```
Met Ser Ile Ser Val Asn Gly Gln Ser Val Pro Pro Gly Phe Arg
1               5                   10                  15

Phe His Pro Thr Glu Glu Leu Leu Thr Tyr Tyr Leu Ala Lys Lys
                20                  25                  30

Val Ala Ser Gln Arg Ile Asp Leu Asp Val Ile Pro Asp Val Asp Leu
            35                  40                  45

Asn Lys Leu Glu Pro Trp Asp Ile Gln Glu Cys Cys Arg Ile Gly Thr
    50                  55                  60

Gly Pro Gln Asn Asp Trp Tyr Leu Phe Ser His Lys Asp Lys Lys Tyr
65                  70                  75                  80

Pro Thr Gly Thr Arg Thr Asn Arg Ala Thr Thr Val Gly Phe Trp Lys
                85                  90                  95

Ala Thr Gly Arg Asp Lys Ala Ile Tyr Pro Ala Ala Gly Tyr Gly His
                100                 105                 110

Ile Gly Met Arg Lys Thr Leu Val Phe Tyr Gln Gly Arg Ala Pro His
            115                 120                 125

Gly His Lys Ser Asp Trp Ile Met His Glu Tyr Arg Leu Asp Asp Ala
    130                 135                 140

Thr Thr Pro Gly Asn Asn Pro Ala Asn Gln Ala Ile Gly Asn Ala Pro
145                 150                 155                 160

Tyr Tyr Pro Gly Ser Ser Ser Ile Arg Ser Leu Val Gly Asp Gln
                165                 170                 175

Ser Ser Ala Gln Glu Asp Gly Trp Val Ile Cys Arg Val Phe Lys Lys
            180                 185                 190

Lys Asn Ile Val Val Gln Gln Ala Asp Gln Asn Gly Gly Arg
    195                 200                 205

Arg Thr Ala Ser Asn Asn Leu Val Ala Ala Gly Ala Ile Glu Leu Ser
    210                 215                 220

Arg Ser Asn Cys Ser Ser Thr Val Thr Thr Ala Ser Asp His Ala Lys
225                 230                 235                 240

Ala Thr His Met Gln Gln His Tyr Tyr Ser Ala Ser Asp Asp Ala Leu
                245                 250                 255

Asp His Ile Leu Asn Gln Tyr Met His Gly Arg Ser Ser Thr Thr Thr
                260                 265                 270

Thr Ser Cys Lys Lys Glu Thr Asn Ala Thr Asn Pro Ser Ser Ser Ala
    275                 280                 285

Leu Asp His Leu Ile Asn Ser Glu Cys His Asn Val Ser Ser Thr Leu
    290                 295                 300

Tyr Glu Lys Leu Pro Pro Leu Glu His Val Val Pro Gly Glu Leu Leu
305                 310                 315                 320

Pro Pro Thr Glu Tyr Ser Gly Asp Trp Asp Ala Leu Asp Arg Leu Ala
                325                 330                 335

Ala Tyr Glu Leu Asn Gly Leu Ser Asp Ala Ala Ser Ala Lys Thr Thr
            340                 345                 350

Asn Gly Met Pro Phe Ile Val Asp Glu Leu Gly Gly Ala Thr Ala Tyr
                355                 360                 365

Ser Gly Gly Gly Arg Leu His Val Ser Ser Ile Thr Gly Thr Gly Asp
    370                 375                 380

Gly Asp Leu Trp Ser Leu Gly Arg Ser Val Ser Ser Leu His Ala Asp
385                 390                 395                 400

Leu Thr Ile Asn Ser Phe Asn Ala Val Gly Cys
                405                 410
```

<210> SEQ ID NO 27
<211> LENGTH: 399
<212> TYPE: PRT
<213> ORGANISM: Arabidopsis thaliana

<400> SEQUENCE: 27

Met Ser Lys Ser Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
            20                  25                  30

Leu Arg Lys Lys Val Asn Ser Ile Glu Ile Asp Leu Asp Val Ile Arg
        35                  40                  45

Asp Val Asp Leu Asn Lys Leu Glu Pro Trp Asp Ile Gln Glu Met Cys
50                  55                  60

Lys Ile Gly Thr Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Ile Ile Tyr Ser Asn Gly
            100                 105                 110

Arg Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Asp
130                 135                 140

Asp Asn Ile Ile Ser Pro Glu Asp Val Thr Val His Glu Val Val Ser
145                 150                 155                 160

Ile Ile Gly Glu Ala Ser Gln Asp Glu Gly Trp Val Val Cys Arg Ile
                165                 170                 175

Phe Lys Lys Lys Asn Leu His Lys Thr Leu Asn Ser Pro Val Gly Gly
            180                 185                 190

Ala Ser Leu Ser Gly Gly Gly Asp Thr Pro Lys Thr Thr Ser Ser Gln
        195                 200                 205

Ile Phe Asn Glu Asp Thr Leu Asp Gln Phe Leu Glu Leu Met Gly Arg
210                 215                 220

Ser Cys Lys Glu Glu Leu Asn Leu Asp Pro Phe Met Lys Leu Pro Asn
225                 230                 235                 240

Leu Glu Ser Pro Asn Ser Gln Ala Ile Asn Asn Cys His Val Ser Ser
                245                 250                 255

Pro Asp Thr Asn His Asn Ile His Val Ser Asn Val Val Asp Thr Ser
            260                 265                 270

Phe Val Thr Ser Trp Ala Ala Leu Asp Arg Leu Val Ala Ser Gln Leu
        275                 280                 285

Asn Gly Pro Thr Ser Tyr Ser Ile Thr Ala Val Asn Glu Ser His Val
290                 295                 300

Gly His Asp His Leu Ala Leu Pro Ser Val Arg Ser Pro Tyr Pro Ser
305                 310                 315                 320

Leu Asn Arg Ser Ala Ser Tyr His Ala Gly Leu Thr Gln Glu Tyr Thr
                325                 330                 335

Pro Glu Met Glu Leu Trp Asn Thr Thr Thr Ser Ser Leu Ser Ser Ser
            340                 345                 350

Pro Gly Pro Phe Cys His Val Ser Asn Val Leu Leu Val Cys Leu
        355                 360                 365

Leu Arg Leu Gln Leu Gln Phe Trp Pro Phe Gln Pro Trp Gln Arg Gln
370                 375                 380

```
Val His Phe Asp Leu Ser Ser Pro Gln Met Gln Ile Ser Leu His
385                 390                 395
```

<210> SEQ ID NO 28
<211> LENGTH: 27
<212> TYPE: DNA
<213> ORGANISM: Artificial
<220> FEATURE:
<223> OTHER INFORMATION: Sense primer for crw1

<400> SEQUENCE: 28
agatctatga gcatctcggt gaacggg                                            27

<210> SEQ ID NO 29
<211> LENGTH: 28
<212> TYPE: DNA
<213> ORGANISM: Artificial
<220> FEATURE:
<223> OTHER INFORMATION: Antisense primer for crw1

<400> SEQUENCE: 29
gttaacctac agtgacacgt ggctgagc                                           28

<210> SEQ ID NO 30
<211> LENGTH: 23
<212> TYPE: DNA
<213> ORGANISM: Artificial
<220> FEATURE:
<223> OTHER INFORMATION: Primer PHN11317

<400> SEQUENCE: 30
ccacccgtcg gcacctccgc ttc                                                23

<210> SEQ ID NO 31
<211> LENGTH: 20
<212> TYPE: DNA
<213> ORGANISM: Artificial
<220> FEATURE:
<223> OTHER INFORMATION: Primer PHN140720

<400> SEQUENCE: 31
ctacagtgac acgtggctga                                                    20

<210> SEQ ID NO 32
<211> LENGTH: 22
<212> TYPE: DNA
<213> ORGANISM: Artificial
<220> FEATURE:
<223> OTHER INFORMATION: Primer PHN140719

<400> SEQUENCE: 32
caccatgagc atctcggtga ac                                                 22

<210> SEQ ID NO 33
<211> LENGTH: 118
<212> TYPE: PRT
<213> ORGANISM: Artificial Sequence
<220> FEATURE:
<223> OTHER INFORMATION: Synthetic sequence

<400> SEQUENCE: 33

```
Ser Asn Gly Gln Ser Val Pro Pro Gly Phe Arg Phe His Pro Thr Glu
1               5                   10                  15

Glu Glu Leu Leu Tyr Tyr Leu Lys Lys Ile Asp Leu Asp Val Ile Asp
            20                  25                  30
```

```
Leu Asn Lys Leu Glu Pro Trp Asp Ile Gln Glu Cys Ile Gly Pro Gln
         35                  40                  45

Asn Trp Tyr Ser His Lys Asp Lys Lys Tyr Pro Thr Gly Thr Arg Thr
 50                  55                  60

Asn Arg Ala Thr Gly Phe Trp Lys Ala Thr Gly Arg Asp Lys Ile Gly
 65                  70                  75                  80

Arg Lys Thr Leu Val Phe Tyr Gly Arg Ala Pro His Gly Lys Ser Asp
                 85                  90                  95

Trp Ile Met His Glu Tyr Arg Leu Trp Val Arg Phe Lys Leu Leu Pro
                100                 105                 110

Leu Glu Asp Ala Leu Gly
            115

<210> SEQ ID NO 34
<211> LENGTH: 346
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (107)..(108)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (225)..(226)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (234)..(235)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
```

-continued

<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (259)..(259)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (306)..(306)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (310)..(310)
<223> OTHER INFORMATION: Xaa can be any naturally occurring amino acid
<220> FEATURE:
<221> NAME/KEY: misc_feature
<222> LOCATION: (319)..(319)
<223> OTHER INFORMATION: Xaa can be any naturally occurring amino acid
<220> FEATURE:
<221> NAME/KEY: misc_feature
<222> LOCATION: (322)..(322)
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (338)..(338)
<223> OTHER INFORMATION: Xaa can be any naturally occurring amino acid

<400> SEQUENCE: 34

Met Ser Ile Ser Val Asn Gly Gln Ser Gln Val Pro Pro Gly Phe Arg
1               5                   10                  15

Phe His Pro Thr Glu Glu Leu Leu Xaa Tyr Tyr Leu Arg Lys Lys
            20                  25                  30

Val Ala Ser Glu Lys Ile Asp Leu Asp Val Ile Arg Asp Val Asp Leu
        35                  40                  45

Asn Lys Leu Glu Pro Trp Asp Ile Gln Glu Lys Cys Lys Ile Gly Ser
50                  55                  60

Thr Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Ser Xaa Xaa Arg Arg Ile Gly
            100                 105                 110

Met Arg Lys Thr Leu Val Phe Tyr Lys Gly Arg Ala Pro His Gly Gln
        115                 120                 125

Lys Ser Asp Trp Ile Met His Glu Tyr Arg Leu Asp Asp Pro Pro Tyr
130                 135                 140

Thr Ala Asp Xaa Ala Ala Val Ser Asn Ala Ala Gly Asp Ala Ala Gln
145                 150                 155                 160

Glu Glu Gly Trp Val Val Cys Arg Val Phe Lys Lys Lys Asn His His
                165                 170                 175

-continued

```
Lys Thr Leu Asp Ser Pro Xaa Lys Ala Gly Ser Xaa Ala Gly Thr Asp
            180                 185                 190

Ala Xaa Thr His Leu Gln Xaa Ser Xaa Asn Asp Ala Leu Asp Gln
        195                 200                 205

Ile Leu Gln Tyr Met Gly Arg Ser Cys Lys Gln Glu His Glu Leu Glu
        210                 215                 220

Xaa Xaa Arg Xaa Thr Ser Arg Xaa Asn Xaa Xaa Gly Gly His Arg Phe
225                 230                 235                 240

Met Lys Leu Pro Pro Leu Glu Ser Pro Xaa Ser Ala Ser Ile Glu Xaa
            245                 250                 255

Pro His Xaa Thr Ser Xaa Asp Tyr Asn Asn Ala Ser Asn Gly Xaa Ser
            260                 265                 270

Gly Ile Thr Asp Trp Ala Ala Leu Asp Arg Leu Val Ala Ser Gln Leu
        275                 280                 285

Asn Gly Gln Thr Asp Ala Ser Lys Gln Leu Ser Cys Phe Phe Asp Asp
        290                 295                 300

Asp Xaa Pro Xaa Leu Xaa Ser Ala Ala Ala Thr Gln Leu Tyr Xaa Ser
305                 310                 315                 320

Asp Xaa Asp Leu Trp Ser Phe Thr Arg Ser Ser Ser Ser Leu Ser Xaa
            325                 330                 335

Ser Xaa Glu Pro Leu Cys His Val Ser Val
        340                 345
```